US010980865B2

(12) United States Patent
Chang et al.

(10) Patent No.: US 10,980,865 B2
(45) Date of Patent: Apr. 20, 2021

(54) DIRECT APPLICATION SYSTEM AND METHOD FOR THE DELIVERY OF BIOACTIVE COMPOSITIONS AND FORMULATIONS

(71) Applicant: AQUAVIT PHARMACEUTICALS, INC., New York, NY (US)

(72) Inventors: Sobin Chang, New York, NY (US); David J. Goldberg, New York, NY (US); David Shafer, New York, NY (US)

(73) Assignee: AQUAVIT PHARMACEUTICALS, INC., New York, NY (US)

( * ) Notice: Subject to any disclaimer, the term of this patent is extended or adjusted under 35 U.S.C. 154(b) by 568 days.

(21) Appl. No.: 14/909,954

(22) PCT Filed: Aug. 4, 2014

(86) PCT No.: PCT/US2014/049652
§ 371 (c)(1),
(2) Date: Feb. 3, 2016

(87) PCT Pub. No.: WO2015/020982
PCT Pub. Date: Feb. 12, 2015

(65) Prior Publication Data
US 2016/0175408 A1 Jun. 23, 2016

Related U.S. Application Data

(60) Provisional application No. 61/945,339, filed on Feb. 27, 2014, provisional application No. 61/941,032, (Continued)

(51) Int. Cl.
*A61K 38/48* (2006.01)
*A61K 8/66* (2006.01)
(Continued)

(52) U.S. Cl.
CPC ............ *A61K 38/4893* (2013.01); *A61K 8/19* (2013.01); *A61K 8/23* (2013.01); *A61K 8/27* (2013.01); *A61K 8/355* (2013.01); *A61K 8/361* (2013.01); *A61K 8/498* (2013.01); *A61K 8/553* (2013.01); *A61K 8/65* (2013.01); *A61K 8/66* (2013.01); *A61K 8/675* (2013.01); *A61K 8/678* (2013.01); *A61K 8/735* (2013.01); *A61K 8/98* (2013.01); *A61K 9/0014* (2013.01); *A61K 31/122* (2013.01); *A61K 31/202* (2013.01); *A61K 31/352* (2013.01); *A61K 31/355* (2013.01); *A61K 31/592* (2013.01); *A61K 31/685* (2013.01); *A61K 33/00* (2013.01); *A61K 33/04* (2013.01); *A61K 33/06* (2013.01);
(Continued)

(58) Field of Classification Search
CPC ........ A61M 5/24; A61M 5/30; A61M 5/3298; A61M 2037/0023; A61M 2037/0061; A61M 2205/505; A61M 2205/6054; A61M 2025/0093; A61M 37/0015; A61M 2037/003; A61K 38/4893; A61K 8/19; A61K 8/23; A61K 8/27; A61K 8/355; A61K 8/361; A61K 8/498; A61K 8/553; A61K 8/65; A61K 8/66; A61K 8/675; A61K 8/678; A61K 8/735; A61K 8/98; A61K 9/0014; A61K 31/122; A61K 31/202; A61K 31/352; A61K 31/355; A61K 31/592; A61K 31/685; A61K 33/00; A61K 33/04; A61K 33/06; A61K 33/30; A61K 38/063; A61K 2800/91; A61Q 7/00; A61Q 19/00; A61Q 19/08; C12Y 304/24069
See application file for complete search history.

(56) References Cited

U.S. PATENT DOCUMENTS 4,467,844 A  8/1984 Digianfilippo
4,513,796 A  4/1985 Miller
(Continued)

FOREIGN PATENT DOCUMENTS

CA       2496005 A1   2/2004
WO  WO 2001/026642 A2  4/2001
(Continued)

OTHER PUBLICATIONS

Borrione et al.: "*Platelet-rich plasma in muscle healing*"; Am J Phys Med Rehabil. 89(10):854-61. (2010).
Fagien et al.: "*Reconstituted injectable hyaluronic acid: expanded application in facial aesthetics and additional thoughts on the mechanism of action in cosmetic medicine*"; Plastic and reconstructive surgery, 130: 208-217 (2012).
International Search Report dated Feb. 10, 2015, regarding PCT/US2014/049652.
International Search Report dated Nov. 4, 2013, regarding PCT/US2013/054421.
(Continued)

*Primary Examiner* — Robert A Wax
*Assistant Examiner* — Olga V. Tcherkasskaya
(74) *Attorney, Agent, or Firm* — K&L Gates LLP

(57) ABSTRACT

The embodiments relate to improved skin quality, health and appearance using a new delivery method and certain bioactive compositions and formulations. The system incorporates microneedle delivery technology with unique compositions and formulations. Such development allows for the pursuit of personalized medicine, or treatment delivery that can expand to remote controlled environment, immediate compounding and ultimate personalization with a state of the art longitudinal data predictive analytics. Certain formulations described herein are unique, combinatory and synergistic. Secured by high-tech proprietary system, there are unlimited potentials using AQT technology including but not limited to 3-D printing of a biodegradable micro chips that can be delivered via injection, AQT or any other possible route.

30 Claims, 11 Drawing Sheets

Related U.S. Application Data filed on Feb. 18, 2014, provisional application No. 61/909,977, filed on Nov. 27, 2013, provisional application No. 61/862,024, filed on Aug. 4, 2013, provisional application No. 61/862,026, filed on Aug. 4, 2013, provisional application No. 61/862,027, filed on Aug. 4, 2013.

(51) Int. Cl.

| | | |
|---|---|---|
| A61K 8/73 | (2006.01) | |
| A61K 8/67 | (2006.01) | |
| A61K 33/30 | (2006.01) | |
| A61K 8/27 | (2006.01) | |
| A61K 31/355 | (2006.01) | |
| A61K 33/04 | (2006.01) | |
| A61K 8/23 | (2006.01) | |
| A61K 8/19 | (2006.01) | |
| A61K 8/49 | (2006.01) | |
| A61K 8/36 | (2006.01) | |
| A61K 8/55 | (2006.01) | |
| A61K 8/35 | (2006.01) | |
| A61K 8/65 | (2006.01) | |
| A61K 8/98 | (2006.01) | |
| A61K 9/00 | (2006.01) | |
| A61K 38/06 | (2006.01) | |
| A61K 31/685 | (2006.01) | |
| A61K 31/592 | (2006.01) | |
| A61K 31/352 | (2006.01) | |
| A61K 33/06 | (2006.01) | |
| A61K 33/00 | (2006.01) | |
| A61K 31/202 | (2006.01) | |
| A61K 31/122 | (2006.01) | |
| A61Q 7/00 | (2006.01) | |
| A61Q 19/00 | (2006.01) | |
| A61M 37/00 | (2006.01) | |
| A61Q 19/08 | (2006.01) | |
| A61M 5/32 | (2006.01) | |
| A61M 5/24 | (2006.01) | |
| A61M 5/30 | (2006.01) | |

(52) U.S. Cl.
CPC ............ *A61K 33/30* (2013.01); *A61K 38/063* (2013.01); *A61Q 7/00* (2013.01); *A61Q 19/00* (2013.01); *A61K 2800/91* (2013.01); *A61M 5/24* (2013.01); *A61M 5/30* (2013.01); *A61M 5/3298* (2013.01); *A61M 2037/0023* (2013.01); *A61M 2037/0061* (2013.01); *A61M 2205/505* (2013.01); *A61M 2205/6054* (2013.01); *A61Q 19/08* (2013.01); *C12Y 304/24069* (2013.01)

(56) References Cited

U.S. PATENT DOCUMENTS

| | | | |
|---|---|---|---|
| 4,587,793 A | 5/1986 | Brennan | |
| 4,653,010 A | 3/1987 | Figler | |
| 4,712,460 A | 12/1987 | Allen | |
| 4,789,014 A | 12/1988 | Digianfilippo | |
| 4,922,975 A | 5/1990 | Polaschegg | |
| 5,040,699 A | 8/1991 | Gangemi | |
| 5,085,256 A | 2/1992 | Kircher | |
| 5,274,166 A | 12/1993 | Sintov | |
| 5,431,202 A | 7/1995 | Dikeman | |
| 5,514,150 A | 5/1996 | Rostoker | |
| 5,658,947 A | 8/1997 | Dasgupta | |
| 5,697,407 A | 12/1997 | Lasonde | |
| 5,837,728 A | 11/1998 | Purcell | |
| 5,848,991 A | 12/1998 | Gross | |
| 5,935,096 A * | 8/1999 | Barrett | A61F 9/00745 604/22 |
| 5,942,543 A | 8/1999 | Ernst | |
| 6,048,086 A | 4/2000 | Valerino | |
| 6,090,790 A | 7/2000 | Eriksson | |
| 6,182,712 B1 | 2/2001 | Stout | |
| 6,283,974 B1 | 9/2001 | Alexander | |
| 6,503,231 B1 | 1/2003 | Prausnitz | |
| 6,611,707 B1 | 8/2003 | Prausnitz | |
| 6,743,211 B1 * | 6/2004 | Prausnitz | A61B 5/14514 604/239 |
| 6,881,203 B2 | 4/2005 | Delmore | |
| 6,951,228 B2 | 10/2005 | Steigerwalt | |
| 6,975,924 B2 | 12/2005 | Kircher | |
| 6,991,002 B2 | 1/2006 | Osborne | |
| 7,171,992 B2 | 2/2007 | Digianfilippo | |
| 7,194,336 B2 | 3/2007 | Digianfilippo | |
| 7,226,439 B2 | 6/2007 | Prausnitz | |
| 7,288,259 B2 | 10/2007 | Sanders | |
| 7,422,574 B2 | 9/2008 | Eriksson | |
| 7,473,559 B2 | 1/2009 | Lee | |
| 7,556,615 B2 | 7/2009 | Pettis | |
| 7,556,821 B2 | 7/2009 | Ameri | |
| 7,579,013 B2 | 8/2009 | Ameri | |
| 7,610,115 B2 | 10/2009 | Rob | |
| 7,666,435 B2 | 2/2010 | Sanders | |
| 7,824,693 B2 | 11/2010 | Sanders | |
| 7,879,341 B2 * | 2/2011 | Taylor | A61K 8/64 424/247.1 |
| 7,918,814 B2 | 4/2011 | Prausnitz | |
| 7,950,423 B2 | 5/2011 | Poole | |
| 7,963,935 B2 | 6/2011 | Cormier | |
| 8,034,357 B2 | 10/2011 | Sanders | |
| 8,069,886 B1 | 12/2011 | Yanke | |
| 8,153,139 B1 | 4/2012 | Sanders | |
| 8,202,522 B1 | 6/2012 | Sanders | |
| 8,252,321 B2 | 8/2012 | Dipierro | |
| 8,741,336 B2 | 6/2014 | Dipierro | |
| 9,022,997 B2 | 5/2015 | Chung | |
| 9,622,957 B2 * | 4/2017 | Tezel | C12N 9/6489 |
| 9,675,519 B2 | 6/2017 | Chang | |
| 9,795,774 B2 * | 10/2017 | Takada | A61M 37/0015 |
| 9,993,423 B2 * | 6/2018 | Quan | A61K 9/0021 |
| 10,106,278 B2 | 10/2018 | Chang | |
| 2002/0035412 A1 | 3/2002 | Kircher | |
| 2002/0138049 A1 | 9/2002 | Allen | |
| 2003/0135201 A1 | 7/2003 | Gonnelli | |
| 2005/0008683 A1 | 6/2005 | Mikszta | |
| 2005/0209565 A1 | 9/2005 | Yuzhakov | |
| 2005/0271608 A1 | 12/2005 | Gupta | |
| 2005/0283125 A1 * | 12/2005 | Barkhahn | A61L 31/14 604/272 |
| 2006/0018867 A1 * | 1/2006 | Kawasaki | A61K 8/898 424/70.122 |
| 2006/0047254 A1 * | 3/2006 | Akahoshi | A61F 9/00745 604/272 |
| 2006/0136095 A1 | 6/2006 | Rob | |
| 2006/0138095 A1 | 6/2006 | Stellwag | |
| 2006/0259195 A1 | 11/2006 | Eliuk | |
| 2007/0142885 A1 * | 6/2007 | Hantash | A61B 18/1477 607/102 |
| 2007/0178121 A1 * | 8/2007 | First | A61K 8/64 424/239.1 |
| 2008/0059228 A1 | 3/2008 | Bossi | |
| 2008/0140046 A1 | 6/2008 | Buck | |
| 2008/0161782 A1 | 7/2008 | Chan et al. | |
| 2008/0169043 A1 | 7/2008 | Osborne | |
| 2008/0189043 A1 | 8/2008 | Anno | |
| 2008/0319092 A1 | 12/2008 | Singh | |
| 2009/0155314 A1 | 6/2009 | Tezel | |
| 2009/0281657 A1 | 11/2009 | Gak | |
| 2009/0318833 A1 * | 12/2009 | Lim | A61M 5/329 600/573 |
| 2010/0068232 A1 * | 3/2010 | Key | A61K 8/65 424/239.1 |
| 2010/0100237 A1 | 4/2010 | Ratnakar | |
| 2010/0196445 A1 | 8/2010 | David et al. | |
| 2010/0241270 A1 | 9/2010 | Eliuk | |

(56) References Cited

U.S. PATENT DOCUMENTS

| | | |
|---|---|---|
| 2011/0195124 A1 | 8/2011 | Jin |
| 2012/0296280 A1 | 11/2012 | Eum |
| 2013/0059549 A1 | 3/2013 | Ogata |
| 2013/0078228 A1* | 3/2013 | Abiko ............ A61K 9/0019 424/94.1 |
| 2013/0203850 A1 | 8/2013 | Soto |
| 2014/0014226 A1 | 1/2014 | Green |
| 2014/0186309 A1* | 7/2014 | Klassen ............ C12N 5/0621 424/93.7 |
| 2014/0278510 A1 | 9/2014 | McLean |
| 2015/0034208 A1 | 2/2015 | Chang |
| 2015/0216763 A1 | 8/2015 | Fearnot |
| 2015/0238527 A1 | 8/2015 | Chang |

FOREIGN PATENT DOCUMENTS

| | | | |
|---|---|---|---|
| WO | 2008/072229 A1 | 6/2008 | |
| WO | WO-2008072229 A2 * | 6/2008 | ........ A61M 37/0015 |
| WO | 2008/154705 A1 | 12/2008 | |
| WO | WO 2010/097564 A2 | 9/2010 | |
| WO | WO 2011/138971 A1 | 11/2011 | |
| WO | WO 2011/138973 A1 | 11/2011 | |
| WO | 2012/109032 | 8/2012 | |
| WO | 2013/044314 A1 | 4/2013 | |
| WO | 2013/058879 A2 | 4/2013 | |
| WO | WO 2014/026161 A1 | 2/2014 | |

OTHER PUBLICATIONS

Molnar, J.: "*Nutrition and Wound Healing*"; CRC Press, (2006), Chapter 7, "*B vitamins and wound healing*"; 23 pages.

Molnar, J.: "*Nutrition and Wound Healing*"; CRC Press, (2006), Chapter 8, "*Vitamin C and wound healing*"; 30 pages.

Molnar, J.: "*Nutrition and Wound Healing*"; CRC Press, (2006), Chapter 10, "*Trace elements and wound healing*"; 47 Pages.

Olsen et al.: "*A multicenter, randomized, placebo-controlled, double-blind clinical trial of a novel formulation of 5% minoxidil topical foam versus placebo in the treatment of androgenetic alopecia in men*"; J Am Acad Dermatol, 57(5): 767-74 (2007).

Papakonstantinou et al.: "*Hyaluronic acid: A key molecule in skin aging*"; Dermato-endocrinology, 4: 253-258 (2012).

Varani et al.: "*Decreased Collagen Production in Chronically Aged Skin*"; Am J Pathol., 168(6): 1861-1868 (2006).

Plaintiff's verified complaint, *Aquavit Pharmaceuticals, Inc., V. U-B10 Med, Inc., Global Medi Jroducts, and Nyun Shi Eum aka Nyeon-Sik Eum*, Case No. 1:19-CV-3351 (VEC), United States District Court Southern District of New York, (2019), pp. 1-60.

Defendant U-Bio Med, Inc.'s answer to complaint, *Aquavit Pharmaceuticals, Inc., V. U-Bio Med, Inc., Global Medi Products, and Nyun Shi Eum aka Nyeon-Sik Eum*, Case No. 1:19-CV-3351 (VEC), United States District Court Southern District of New York, (2019), pp. 1-24.

Sculptra Aesthetic (injectable poly-L-lactic Acid), 35 pages (2009), Sanofi-Aventis U.S. LLC., Bridgewater, New Jersey.

Aquavit Pharmaceuticals, Inc., Aquavit Pharmaceuticals, Inc. Secures Preliminary Injunction and Restraining Order Against Counterfeiters on Patent and Trademark Infringement Case, (Apr. 29, 2019), 4 pages, Retrieved from: https://www.pmewswire.com/news-releases/aquavit-pharmaceuticals-inc-secures-preliminary-injunction-and-restraining-order-against-counterfeiters-on-patent-and-trademark-infringement-case-300840296.html.

Olsen et al., A multicenter, randomized, placebo-controlled, double-blind clinical trial of a novel formulation of 5% minoxidil topical foam versus placebo in the treatment of androgenetic alopecia in men, Journal of the American Academy of Dermatology, (2017), 57(5):767-774, University of Minnesota, Minneapolis, Minnesota.

Borrione et al., Platelet-Rich Plasma in Muscle Healing, Americal Journal of Physical medicine & Rehabilitation, (2010), 89(10):854-861, Wolters Kluwer, The Netherlands.

Varani et al., Decreased Collagen Production in Chronologically Aged Skin, American Journal of Pathology, (2006), 168(6)1861-1868, American Society for Investigative Pathology, Rockville, Maryland.

Sculptra Aesthetic (injectable poly-L-lactic Acid), Bradgewater, NJ. Sanofi-Aventis U.S. LLC. (2012), DJA X00033, Bridgewater, New Jersey.

Papakonstantinou et al., Hyaluronic Acid, A Key Molecule in skin Aging, Dermato Endocrinology, (2012), 4(3):253-258, Landes bioscinence, Austin, Texas.

Baumgartner, Chapter 10: Trace Elements and Wound Healing, Nutrition and Wound Healing, CRC Press, Edited by Joseph Molar, (2007) p. 173-216, Taylor & Francis Group, LLC, United Kingdom.

Takana et al., Chapter 8: Vitamin C and Wound Healing, Nutrition and Wound Healing, edited by Joseph Molnar, CRC Press, (2007) p. 121-148, Taylor & Francis Group, LLC, United Kingdom.

Liepa et al., Chapter 7: B Vitamins and Wound Healing, Nutrition and Wound Healing, edited by Joseph Molnar, CRC Press, (2007) p. 99-119, Taylor & Francis Group, LLC, United Kingdom.

International Search Report from Int. Appl. No. PCT/US2013/054421, dated Nov. 4, 2013.

International Search Report from Int. Appl. No. PCT/US2014/49652, dated Feb. 10, 2015.

Fagien, Reconstituted injectable hyaluronic acid: expanded applications in facial aesthetics and additional thoughts on the mechanism of action in cosmetic medicine, Plast Reconstr Surg., (2012) 130:(1):208-217, Wolters Kluwer, The Netherlands.

Office Action from U.S. Appl. No. 14/420,856, dated Jul. 16, 2018.
Office Action from U.S. Appl. No. 14/420,856, dated Jun. 26, 2019.
Office Action from U.S. Appl. No. 14/964,402, dated May 17, 2017.
Office Action from U.S. Appl. No. 14/964,402, dated Dec. 26, 2017.
European Official Communication from European Patent Appl. No. 12703657.2, dated Jan. 29, 2015.
International Search Report from Int. Appl. No. PCT/US2012/022902, dated Apr. 24, 2012.
Office Action from U.S. Appl. No. 13/982,213, dated Aug. 27, 2015.
Office Action from U.S. Appl. No. 13/982,213, dated Dec. 30, 2015.
Office Action from U.S. Appl. No. 13/982,213, dated Nov. 25, 2016.

\* cited by examiner

Image of a screw on microneedle head.

AQT microneedle components: (A) microneedles, (B) housing of the needles and (C) a reservoir.

Modular Smart Label Data Transmission Systems for Applied End-User Optimization

DIRECT APPLICATION SYSTEM AND METHOD FOR THE DELIVERY OF BIOACTIVE COMPOSITIONS AND FORMULATIONS

CROSS-REFERENCE

This application is a 35 USC § 371 National Stage application of International Application No. PCT/US2014/049652 filed Aug. 4, 2014, now pending; which claims the benefit under 35 USC § 119(e) to U.S. Application Ser. No. 61/945,339 filed Feb. 27, 2014, U.S. Application Ser. No. 61/941,032 filed Feb. 18, 2014, U.S. Application Ser. No. 61/909,977 filed Nov. 27, 2013, U.S. Application Ser. No. 61/862,027 filed Aug. 4, 2013, U.S. Application Ser. No. 61/862,026 filed Aug. 4, 2013 and U.S. Application Ser. No. 61/862,024 filed Aug. 4, 2013. The disclosure of each of the prior applications is considered part of and is incorporated by reference in the disclosure of this application.

This application is related to U.S. application Ser. No. 14/212,415, filed Mar. 14, 2014; which claims the benefit of U.S. Provisional Applications Nos. 61/792,624, filed Mar. 15, 2013; 61/792,970, filed Mar. 15, 2013; 61/794,558, filed Mar. 15, 2013; 61/794,274, filed Mar. 15, 2013; 61/793,946, filed Mar. 15, 2013; 61/792,246, filed Mar. 15, 2013; 61/790,912, filed Mar. 15, 2013; and 61/790,469, filed Mar. 15, 2013; each of which is incorporated by reference in its entirety. This application is also related to PCT Application No. PCT/US13/54421, filed Aug. 9, 2013, which claims the benefit of U.S. Provisional Application No. 61/682,056, filed Aug. 10, 2012, to U.S. Provisional Application No. 61/862,024, filed Aug. 4, 2012; U.S. Provisional Application No. 61/862,026, filed Aug. 4, 2012, and U.S. Provisional Application No. 61/862,027, filed Aug. 4, 2012; each of which is incorporated by reference in its entirety.

BACKGROUND OF THE INVENTION

Existing methods of administering treatments into human body are extremely limited. Conventional choices such as topical, patches, injectables (e.g., intramuscular, intravenous, subcutaneous (SubQ)), inhaled, nasal spray, and oral routes of administration usually accompany limitations.

SUMMARY OF THE INVENTION

The compositions and devices of the present application facilitate the delivery method of a broad range of therapeutic, nutraceutical and/or aesthetic compounds and formulations directly into layers of the skin, while painlessly stimulating the native production of collagen. This micro transjection-like method has been termed compounding and delivery technology (e.g. marketed under the name of Aquagold Technology (AQT technology)). By avoiding routes of filtration, absorption and digestive modification that occur in the hepatic, renal or gastrointestinal systems, bioactive agents may reach their target location without extraneous factors diminishing biological activity or amount of dosage. Compared to injectables, AQT technology provides virtually no pain, bruising or bleeding while enabling efficient treatments to be administered to broader areas of the skin. Compared to patches (including those utilizing micro needles), the onset of delivery is significantly faster and associated aesthetic limitations are eliminated. Compared to topicals, efficacy and bioactivity is enhanced significantly. Compared to inhalers and nasal sprays, there are no GI side effects or flavoring issues. Our approach of applying AQT technology, various formulations and compounds, and high-tech device technology and the combinations has the potential to satisfy the expectations of patients that desire an optimal treatment due to its capacity for personalization. The rigorous needs of a medical application for new drug delivery are also satisfied by this invention, with possible applications including, but not limited to, vaccine, hormonal delivery, administration of biologics, and the treatment of arthritis, psoriasis, and other skin conditions.

The compositions and devices of the present application facilitate the delivery method of a broad range of therapeutic, nutraceutical and/or aesthetic compounds and formulations directly into layers of the skin, while painlessly stimulating the native production of collagen. This micro transjection-like method has been termed "AQT technology". By avoiding routes of filtration, absorption and digestive modification that occur in the hepatic, renal or gastrointestinal systems, bioactive agents may reach their target location without extraneous factors diminishing biological activity or amount of dosage. Compared to injectables, AQT provides virtually no pain, bruising or bleeding while enabling efficient treatments to be administered to broader areas of the skin. Compared to patches (including those utilizing micro needles), the onset of delivery is significantly faster and associated aesthetic limitations are eliminated. Compared to topicals, efficacy and bioactivity is enhanced significantly. Compared to inhalers and nasal sprays, there are no GI side effects or flavoring issues. Our approach of applying AQT technology, various formulations and compounds, and high-tech device technology and the combinations has the potential to satisfy the expectations of patients that desire an optimal treatment due to its capacity for personalization. The rigorous needs of a medical application for new drug delivery are also satisfied by this invention, with possible applications including, but not limited to, vaccine, hormonal delivery, administration of biologics, and the treatment of arthritis, psoriasis, and other skin conditions.

There exists a need for formulations for treatment of various conditions. The present inventors have developed compositions formulated for administration as disclosed herein which can be used to treat or ameliorate a disease or one or more symptoms associated with a condition in a human patient. For example, administration of a composition provided herein may improve overall skin quality and health including skin elasticity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; reducing pore size; and making wrinkles appear softer and/or less prominent.

Provided herein is a composition comprising hyaluronic acid, botulinum toxin, collagen, vitamins, minerals, stem cell, platelet-rich plasma (PRP), retinols, antioxidants, growth factors, biamptoprost and/or minoxidil act on the skin, into the skin and/or subcutaneous muscles in order to boost cell rejuvenation and creation, alleviate fine lines and wrinkles, reduce the appearance of scars and blemishes, and improve skin quality, clarity, elasticity, firmness, tone, vitality, and overall skin health.

Active ingredients which may be used in a composition (formulation) described herein include, but are not limited to, vitamins, minerals, hyaluronic acid, collagen, botulinum toxin, platelet-rich plasma, poly-L-lactic acid, lidocaine, epinephrine folic acid, one or more retinols, one or more antioxidants, one or more growth factors, one or more bleaching/whitening agents, one or more stem cell treatments, one or more wound or scar treatments, etc.

In one embodiment, an aqueous solution adapted for human administration, comprises an therapeutically effective amount of one or more of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid (HA), collagen, botulinum toxin, platelet-rich plasma (PRP), poly-L-lactic acid (PLLA), and optionally lidocaine with epinephrine, a chemical stabilizer and optionally a preservative, wherein the aqueous solution is formulated for topical use and/or dermal injection. When referring to a vitamin, it would be understood that all chemical forms of the vitamin are contemplated. The pH of the solution can be adjusted to a pH that is physiologically acceptable for administration to humans. In one embodiment, a composition contains only three of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only four of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only five of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only six of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains all of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and lidocaine with epinephrine.

Provided herein is a product comprising an aqueous solution adapted for human administration, comprising from about 3000 mcg to about 5000 mcg of cyanocobalamin or/and methylcobalamin; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg selenium; from about 30 mg to about 50 mg of glutathione (GSH); from about 100 mg to about 150 mg of anthocyanidin; from about 1 mg to about 500 mg of omega-3; from about 200 mg to about 300 mg of eicosapentaenoic acid (EPA); from about 200 mg to about 300 mg of docosahexaenoic acid (DHA); from about 1 mg to about 500 mg of lecithin; from about 30 mg to about 50 mg of coenzyme Q10 (CoQ10); from about 100 mcg to about 150 mcg of chrome; from about 150 mg to about 200 mg of magnesium; optionally a chemical stabilizer; and optionally a preservative, wherein the aqueous solution is formulated for injection as disclosed herein.

In one embodiment, the product comprises 5000 mcg of cyanocobalamin and/or of methylcobalamin; 1000 mg of ascorbic acid (vitamin C); 15 mg of zinc; 6 mg of ahseutasanchin; 200 IU of vitamin E; 300 IU of vitamin D; 150 mcg of selenium; 50 mg of glutathione (GSH); 150 mg of anthocyanidin; 500 mg of omega-3; 300 mg of EPA; 300 mg of DHA; 500 mg of lecithin; 50 mg of coenzyme Q10 (CoQ10); 150 mcg of chrome; and 200 mg of magnesium.

In one embodiment, a chemical stabilizer for use in the aqueous solution is gentisic acid.

In one embodiment, a preservative is benzyl alcohol.

In one embodiment, the product has a pH from about 7.2 and 7.6, for example, a pH of 7.4.

In one embodiment, the cobalamin is selected from cyanocobalamin or methylcobalamin.

Also provided herein is an aqueous solution formulated for injection as disclosed herein comprising from about 3000 mcg to about 5000 mcg of cyanocobalamin or/and of methylcobalamin; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg of selenium; from about 30 mg to about 50 mg of glutathione (GSH); from about 100 mg to about 150 mg of anthocyanidin; from about 1 mg to about 500 mg of omega-3; from about 200 mg to about 300 mg of EPA; from about 200 mg to about 300 mg of DHA; from about 1 mg to about 500 mg of lecithin; from about 30 mg to about 50 mg of coenzyme Q10 (CoQ10); from about 100 mcg to about 150 mcg of chrome; and from about 150 mg to about 200 mg of magnesium;

The aqueous solution may further comprise a chemical stabilizer.

The aqueous solution may further comprise a preservative.

The aqueous solution may have a pH of about 7.2 to about 7.6 such as, for example, a pH of 7.4.

The aqueous solution of claim 8, wherein the cobalamin is selected from cyanocobalamin, methylcobalamin, or a combination thereof. In one embodiment, the chemical stabilizer is gentisic acid. In another embodiment, the preservative is benzyl alcohol. In another embodiment, the additional bioactive agent is hyaluronic acid, botulinum toxin, platelet-rich plasma, or polylatic acid. The solution may have a pH from about 7.2 and 7.6. In one instance, the solution has a pH of 7.4. Cobalamin to be used in the solutions may be, for example, cyanocobalamin or methylcobalamin.

Preservatives, chemical stabilizers, and/or additional bioactive agents may be added to the compositions in an amount of from about 0.01% and about 2% of the total volume. In one instance, a preservative may be added to the compositions in an amount of from about 0.01% and about 2% of the total volume. In another instance, a chemical stabilizer may be added to the compositions in an amount of from about 0.01% and about 2% of the total volume. In yet another instance, an additional bioactive agent may be added to the compositions in an amount of from about 0.01% and about 2% of the total volume. In yet another instance, two or a preservative, chemical stabilizer and an additional bioactive agent may be added to the compositions in an amount of from about 0.01% and about 2% of the total volume.

In one non-limiting example, a solution may comprise: 5000 mcg of cobalamin (vitamin B12); 200 mg of ascorbic acid (vitamin C); 40 mg of nicotinamide (vitamin B3); 6 mg of thiamine hydrochloride (vitamin B1); 0.1 mg of pyridoxine hydrochloride (vitamin B6); 3.6 mg of riboflavin 5-phosphate sodium (vitamin B2); 10 mg of pantothenic acid (vitamin B5); and 0.1 mg of Zinc sulfate heptahydrate.

Preservatives, chemical stabilizers, and/or additional bioactive agents may be added to the compositions in an amount of from about 0.01% and about 2% of the total volume. In one instance, a preservative may be added to the compositions in an amount of from about 0.01% and about 2% of the total volume. In another instance, a chemical stabilizer may be added to the compositions in an amount of from about 0.01% and about 2% of the total volume. In yet another instance, an additional bioactive agent may be added to the compositions in an amount of from about 0.01% and about 2% of the total volume. In yet another instance, two or a preservative, chemical stabilizer and an additional bioactive agent may be added to the compositions in an amount of from about 0.01% and about 2% of the total volume. In one embodiment, the chemical stabilizer is gentisic acid. In another embodiment, the preservative is benzyl alcohol. In another embodiment, the additional bioactive agent is hyaluronic acid, botulinum toxin, platelet-rich plasma, or polylatic acid. Cobalamin to be used in the solutions may be, for example, cyanocobalamin or methylcobalamin.

The solution may have a pH from about 7.2 and 7.6. In one instance, the solution has a pH of 7.4.

In one aspect, provided herein is a needleless injection device, Aquagold (AQT)-device or a prefilled syringe comprising any of the aqueous solutions described herein. A needleless injection device or pre-filled syringe may, in some instances, comprise: from about 1500 to about 6250 mcg of cobalamin (vitamin B12); from about 150 to about 250 mg of ascorbic acid (vitamin C); from about 30 to about 50 mg of nicotinamide (vitamin B3); from about 4.5 to about 7.5 mg of thiamine (vitamin B1); from about 0.1 to about 0.3 mg of pyridoxine HCl (vitamin B6); from about 2.7 to about 4.5 mg of riboflavin 5-phosphate sodium (vitamin B2); from about 7.5 to about 15 mg of pantothenic acid (vitamin B5); and from about 0.08 to about 0.125 mg of Zinc sulfate heptahydrate.

In one aspect, provided herein is a method of treating or ameliorating a disease or one or more symptoms of a condition in a patient in need thereof, comprising administering to the patient an aqueous solution comprising: from about 1500 to about 6250 mcg of cobalamin (vitamin B12); from about 150 to about 250 mg of ascorbic acid (vitamin C); from about 30 to about 50 mg of nicotinamide (vitamin B3); from about 4.5 to about 7.5 mg of thiamine (vitamin B1); from about 0.1 to about 0.3 mg of pyridoxine HCl (vitamin B6); from about 2.7 to about 4.5 mg of riboflavin 5-phosphate sodium (vitamin B2); from about 7.5 to about 15 mg of pantothenic acid (vitamin B5); and from about 0.08 to about 0.125 mg of Zinc sulfate heptahydrate; wherein the composition is administered to the patient at the surface of the skin without administering to the intramuscular region, for example, through intradermal and/or topical administration. In another embodiment, the composition is administered to the patient by percutaneous delivery. The compositions disclosed herein are preferably administered via an Aquagold (AQT) microneedle system, which delivers the bioactive compositions disclosed herein at or near the skin surface of the subject without penetrating through the dermal layer of the patient or subject.

One or more symptoms may be selected from depression, dementia, fibrobromyalgia, gastrointestinal disorder, headaches, chronic fatigue syndrome, high stress levels, hyperthyroidism, low energy, impaired memory, hair loss, wound healing, scarring, aging, longevity, wellness purpose, and a combination thereof.

A disease to be treated includes, but is not limited to, beriberi, Wernicke's encephalophay, ariboflavinosis, pellagra, acne, paresthesia, microcyrtic anemia, and macrocytic anemia.

In some instances, administration of said composition improves skin elasticity, skin regeneration, metabolism, or a combination.

A aqueous solution may, in some instances, consist essentially of: 5 mg of cobalamin (vitamin B12); 200 mg of ascorbic acid (vitamin C); 40 mg of nicotinamide (vitamin B3); 6 mg of thiamine (vitamin B1); 0.1 mg of pyridoxine HCl (vitamin B6); 3.6 mg of riboflavin 5-phosphate sodium (vitamin B2); and 10 mg of pantothenic acid (vitamin B5); and 0.1 mg of Zinc sulfate heptahydrate.

In one embodiment, an aqueous solution may further comprise a chemical stabilizer. In another embodiment, an aqueous solution may further comprise a preservative. In another embodiment, an aqueous solution may further comprise a chemical stabilizer and a preservative.

In one aspect, provided herein is an aqueous solution adapted for human administration, the aqueous solution comprising from about 1500 mcg to about 6250 mcg of cobalamin (vitamin B12); from about 150 mg to about 250 mg of ascorbic acid (vitamin C); from about 30 mg to about 50 mg of nicotinamide (vitamin B3); from about 4.5 mg to about 7.5 mg of thiamine (vitamin B1); from about 0.1 mg to about 0.3 mg of pyridoxine HCl (vitamin B6); from about 2.7 mg to about 4.5 mg of riboflavin 5-phosphate sodium (vitamin B2); from about 7.5 mg to 15 mg of pantothenic acid (vitamin B5); from about 0.08 mg to about 0.125 mg of Zinc sulfate heptahydrate; optionally a chemical stabilizer; optionally a preservative; and optionally an additional bioactive agent such as hyaluronic acid, botulinum toxin, platelet rich plasma (PRP), or polylactic acid wherein the aqueous solution is formulated for injection as disclosed herein. Preservatives, chemical stabilizers, and/or additional bioactive agents may be added to the compositions in an amount of from about 0.01% and about 2% of the total volume. In one instance, a preservative may be added to the compositions in an amount of from about 0.01% and about 2% of the total volume. In another instance, a chemical stabilizer may be added to the compositions in an amount of from about 0.01% and about 2% of the total volume. In yet another instance, an additional bioactive agent may be added to the compositions in an amount of from about 0.01% and about 2% of the total volume. In yet another instance, two or a preservative, chemical stabilizer and an additional bioactive agent may be added to the compositions in an amount of from about 0.01% and about 2% of the total volume.

The term "formulated for intradermal injection" refers to composition prepared for direct injection of a substance into dermis, wherein the composition is an aqueous solution consisting of water-soluble components and is prepared in a volume not to exceed 1 ml. The dermis includes the layer of the skin beneath the epidermis. The methods disclosed herein Volumes formulated for dermal injection include, but are not limited to, about 0.1 ml, about 0.2 ml, about 0.3 ml, about 0.4 ml, about 0.5 ml, about 0.6 ml, about 0.7 ml, about 0.8 ml, about 0.9 ml, or about 1.0 ml. Dermal injection may occur via, e.g., micro-needles, syringe, pre-filled syringe, needleless injector, etc.

The term "cobalamin" or "vitamin B12" encompass multiple forms of vitamin B12 suitable for human administration, including cyanocobalamin or methylcobalamin.

Also provided herein is a composition comprising vitamins combined with hyaluronic acid, collagen, botulinum toxin, platelet-rich plasma and/or poly-L-lactic acid. The present inventors have developed formulations for intradermal injection and also topical use that serve aesthetic enhancement purposes. The present inventors have also developed formulations for percutaneous delivery that serve aesthetic enhancement purposes. Included in the formulations described herein are formulations that are designed to improve skin condition, enhance skin texture, and appearance. For example, administration of a composition provided herein may improve skin quality, elasticity, luminosity, skin regeneration, metabolism, smoothness and/or softness of skin (i.e., making the skin feel smoother and softer following treatment); the overall appearance and health of skin; evening out skin tone and texture; clarity and/or radiance of skin; making the skin look younger; and reducing pore size and fine lines and making wrinkles and facial fine lines appear softer and/or less prominent.

In one aspect, provided herein is an aqueous solution adapted for human administration, the aqueous solution comprising from about 1500 mcg to about 5000 mcg of cobalamin (vitamin B12); from about 100 mg to about 200 mg of ascorbic acid (vitamin C); from about 10 mg to about 60 mg of nicotinamide (vitamin B3); from about 2 mg to about 10 mg of thiamine hydrochloride (vitamin B1); from about 0.1 mg to about 0.25 mg of pyridoxine HCl (vitamin B6); from about 2 mg to about 10 mg of riboflavin 5-phosphate sodium (vitamin B2); from about 0.1 mg to about 0.5 mg of zinc sulfate heptahydrate; 2.4-12 mg/ml of HA; optionally lidocaine with epinephrine; a chemical stabilizer; and optionally a preservative. Preservatives and chemical stabilizers may be added to the compositions in an amount of from about 0.01% and about 2% of the total volume.

In another aspect, provided herein is a formulation or composition comprising an aqueous solution comprising about 5000 mcg of cobalamin (vitamin B12); about 200 mg of ascorbic acid (vitamin C); about 40 mg of nicotinamide (vitamin B3); about 6 mg of thiamine (vitamin B1); about 0.1 mg of pyridoxine HCl (vitamin B6); about 3.6 mg of riboflavin 5-phosphate sodium (vitamin B2); about 0.1 mg of zinc sulfate heptahydrate; about 12 mg/ml HA, and any concentration of collagen, botulinum toxin, platelet-rich plasma (PRP), and/or poly-L-lactic acid (PLLA) as determined necessary to achieve aesthetic goals set by the doctor and patient. A formulation or composition provided herein may, in some instances, contain three, four, five, six, or all of the following: cobalamin (vitamin B12); ascorbic acid (vitamin C); nicotinamide (vitamin B3); thiamine (vitamin B1); pyridoxine HCl (vitamin B6); riboflavin 5-phosphate sodium (vitamin B2); zinc sulfate heptahydrate; and hyaluronic acid (HA), collagen, botulinum toxin, platelet-rich plasma (PRP), and/or poly-L-lactic acid (PLLA).

In another aspect, provided herein is a formulation or composition comprising an aqueous solution comprising about 5000 mcg cobalamin (vitamin B12); about 200 mg ascorbic acid (vitamin C); about 40 mg nicotinamide (vitamin B3); about 6 mg thiamine (vitamin B1); about 0.1 mg pyridoxine HCl (vitamin B6); about 3.6 mg riboflavin 5-phosphate sodium (vitamin B2); about 0.1 mg zinc sulfate heptahydrate; about 12 mg/ml HA, and any concentration of, collagen, botulinum toxin, platelet-rich plasma (PRP), and/or poly-L-lactic acid (PLLA) as determined necessary to achieve aesthetic goals set by the doctor and patient. A formulation or composition provided herein may, in some instances, contain three, four, five, six, or all of the following: cobalamin (vitamin B12); ascorbic acid (vitamin C); nicotinamide (vitamin B3); thiamine (vitamin B1); pyridoxine HCl (vitamin B6); riboflavin 5-phosphate sodium (vitamin B2); zinc sulfate heptahydrate; and hyaluronic acid (HA), collagen, botulinum toxin, platelet-rich plasma (PRP), and/or poly-L-lactic acid (PLLA).

The term "formulated for intradermal injection" refers to composition prepared for direct injection of a substance into dermis, wherein the composition is an aqueous solution consisting of water-soluble components and is prepared in a volume not to exceed 1 ml. Volumes formulated for dermal injection include, but are not limited to, about 0.1 ml, about 0.2 ml, about 0.3 ml, about 0.4 ml, about 0.5 ml, about 0.6 ml, about 0.7 ml, about 0.8 ml, about 0.9 ml, or about 1.0 ml. Dermal injection may occur via, e.g., micro-needles, syringe, pre-filled syringe, needleless injector, etc.

Also provided herein is a container, which contains a composition prepared for direct injection of a substance into a muscle, wherein the composition is an aqueous solution consisting of water-soluble components. Also provided herein is a container, which contains a composition prepared for direct injection, wherein the composition is an aqueous solution consisting of water-soluble components. Volumes to be considered for packaging in the containers include, but are not limited to, about 0.1 ml, about 0.2 ml, about 0.3 ml, about 0.4 ml, about 0.5 ml, about 0.6 ml, about 0.7 ml, about 0.8 ml, about 0.9 ml, about 1.0 ml, about 1.1 ml, about 1.2 ml, about 1.3 ml, about 1.4 ml, about 1.5 ml, about 1.6 ml, about 1.7 ml, about 1.8 ml, about 1.9 ml, about 2.0 ml, about 2.1 ml, about 2.2 ml, about 2.3 ml, about 2.4 ml, about 2.5 ml, about 2.6 ml, about 2.7 ml, about 2.8 ml, about 2.9 ml, about 3.0 ml, about 3.1 ml, about 3.2 ml, about 3.3 ml, about 3.4 ml, about 3.5 ml, about 3.6 ml, about 3.7 ml, about 3.8 ml, about 3.9 ml, about 4.0 ml, about 4.1 ml, about 4.2 ml, about 4.3 ml, about 4.4 ml, about 4.5 ml, about 4.6 ml, about 4.7 ml, about 4.8 ml, about 4.9 ml, and about 5.0 ml.

In one aspect, the container comprises a composition comprising an aqueous solution formulated for injection, the aqueous solution formulated for injection comprising about 5000 mcg of cobalamin (vitamin B12); about 200 mg of ascorbic acid (vitamin C); about 40 mg of nicotinamide (vitamin B3); about 6 mg of thiamine (vitamin B1); about 0.1 mg of pyridoxine HCl (vitamin B6); about 3.6 mg of riboflavin 5-phosphate sodium (vitamin B2); about 0.1 mg of zinc sulfate heptahydrate; about 12 mg/ml HA, and any concentration of collagen, botulinum toxin, platelet-rich plasma (PRP), and/or poly-L-lactic acid (PLLA). In one aspect, the container is an ampoule, vial, a needleless injection device or pre-filled syringe. Containers described herein may, in some instances, contain a UV-blocking agent which helps prevent degradation of components of the compositions. In one embodiment, a container comprises an aqueous solution which comprises about 5000 mcg of cobalamin (vitamin B12); about 200 mg of ascorbic acid (vitamin C); about 40 mg of nicotinamide (vitamin B3); about 6 mg of thiamine (vitamin B1); about 0.1 mg of pyridoxine HCl (vitamin B6); about 3.6 mg of riboflavin 5-phosphate sodium (vitamin B2); about 0.1 mg of zinc sulfate heptahydrate; about 12 mg/ml HA, and any concentration of collagen, botulinum toxin, platelet-rich plasma (PRP), and/or poly-L-lactic acid (PLLA), where the pH has been adjusted to about 7.4.

Provided herein is a method of promoting vitality and well-being in a human patient, the method comprising administering a vitamin B supplement composition as disclosed herein to the human patient.

Also provided herein is a method of treating or ameliorating disease or symptoms associated with a vitamin B deficiency in a human patient in need thereof, comprising administering to the patient an aqueous solution comprising from about 5000 mcg of cobalamin (vitamin B12); about 200 mg of ascorbic acid (vitamin C); about 40 mg of nicotinamide (vitamin B3); about 6 mg of thiamine (vitamin B1); about 0.1 mg of pyridoxine HCl (vitamin B6); about 3.6 mg of riboflavin 5-phosphate sodium (vitamin B2); about 0.1 mg of zinc sulfate heptahydrate; about 12 mg/ml HA, and any concentration of, collagen, botulinum toxin, platelet-rich plasma (PRP), and/or poly-L-lactic acid (PLLA); wherein the composition is administered to the patient through application to the surface of the skin, for example topically, intradermal, or both. In another embodiment, the composition is percutaneously administered to the patient through application to the surface of the skin. In one embodiment, the pH has been adjusted to about 7.4.

In one aspect, the disease or symptom to be treated includes those associated with a vitamin B deficiency, such as, for example, depression, dementia, fibrobromyalgia, gastrointestinal disorder, headaches, chronic fatigue syndrome, high stress levels, hyperthyroidism, low energy, impaired memory, beriberi, Wernicke's encephalopathy, ariboflavinosis, pellagra, acne, paresthesia, microcyrtic anemia, macrocytic anemia, or a combination thereof.

Also provided herein is a method of improving wound healing in a human patient in need thereof, comprising administering to the patient a composition as disclosed herein. In one embodiment, a composition may be administered prior to surgery, after surgery, or both. Surgery may be, for example, plastic surgery or reconstructive surgery. In one embodiment, the pH has been adjusted to about 7.4.

Also provided herein is a method of improving wound healing in a human patient in need thereof, comprising administering to the patient an aqueous solution comprising about 5000 mcg of cobalamin (vitamin B12); about 200 mg of ascorbic acid (vitamin C); about 40 mg of nicotinamide (vitamin B3); about 6 mg of thiamine (vitamin B1); about 0.1 mg of pyridoxine HCl (vitamin B6); about 3.6 mg of riboflavin 5-phosphate sodium (vitamin B2); about 0.1 mg of zinc sulfate heptahydrate; about 12 mg/ml HA, and any concentration of, collagen, botulinum toxin, platelet-rich plasma (PRP), and/or poly-L-lactic acid (PLLA); wherein the composition is administered to the patient through a microneedle device. In one embodiment, a composition may be administered prior to surgery, after surgery, or both. Surgery may be, for example, plastic surgery or reconstructive surgery. In one embodiment, the pH has been adjusted to about 7.4.

Also provided herein is a method of improving skin elasticity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and making wrinkles appear softer and/or less prominent in human patient in need thereof, comprising administering to the patient a composition as disclosed herein. In some embodiments, the composition may comprise an aqueous solution comprising about 5000 mcg of cobalamin (vitamin B12); about 200 mg of ascorbic acid (vitamin C); about 40 mg of nicotinamide (vitamin B3); about 6 mg of thiamine (vitamin B1); about 0.1 mg of pyridoxine HCl (vitamin B6); about 3.6 mg of riboflavin 5-phosphate sodium (vitamin B2); about 0.1 mg of zinc sulfate heptahydrate; about 12 mg/ml HA, and any concentration of, collagen, botulinum toxin, platelet-rich plasma (PRP), and/or poly-L-lactic acid (PLLA). In one embodiment, the pH has been adjusted to about 7.4.

Also provided herein is a method of improving skin elasticity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and making wrinkles appear softer and/or less prominent in human patient in need thereof, comprising administering to the patient an aqueous solution comprising about 5000 mcg of cobalamin (vitamin B12); about 200 mg of ascorbic acid (vitamin C); about 40 mg of nicotinamide (vitamin B3); about 6 mg of thiamine (vitamin B1); about 0.1 mg of pyridoxine HCl (vitamin B6); about 3.6 mg of riboflavin 5-phosphate sodium (vitamin B2); about 0.1 mg of zinc sulfate heptahydrate; about 12 mg/ml HA, and any concentration of, collagen, botulinum toxin, platelet-rich plasma (PRP), and/or poly-L-lactic acid (PLLA), where the pH has been adjusted to about 7.4.

Embodiments described herein relate to vitamin supplement compositions and injectable hyaluronic acid (HA) formulated for intradermal and tropical use.

There exists a need for vitamin combined with injectable HA formulations. The present inventors have developed new compositions formulated for intradermal and also topical use that serve for aesthetic enhancement purpose. The present inventors have also developed new compositions formulated for percutaneous delivery that serve for aesthetic enhancement purpose. Included in the formulations described herein are new formulations that are designed to improve skin condition, enhance skin texture, and appearance. For example, administration of a composition provided herein may improve skin elasticity, luminosity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and reducing fine lines and making wrinkles and facial fine lines appear softer and/or less prominent.

There exists a need for vitamins combined with hyaluronic acid, collagen, botulinum toxin, platelet-rich plasma and/or poly-L-lactic acid. The present inventors have developed formulations for percutaneous administration, for example, intradermal and also topical use that serve aesthetic enhancement purposes. The present inventors have also developed new compositions formulated for percutaneous delivery that serve for aesthetic enhancement purpose. Included in the formulations described herein are new formulations that are designed to improve skin condition, enhance skin texture, and appearance. For example, administration of a composition provided herein may improve skin elasticity, luminosity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and reducing fine lines and making wrinkles and facial fine lines appear softer and/or less prominent.

In one embodiment, the product comprises an aqueous solution comprising about 5000 mcg of cobalamin (vitamin B12); about 200 mg of ascorbic acid (vitamin C); about 40 mg of nicotinamide (vitamin B3); about 6 mg of thiamine (vitamin B1); about 0.1 mg of pyridoxine HCl (vitamin B6); about 3.6 mg of riboflavin 5-phosphate sodium (vitamin B2); about 0.1 mg of zinc sulfate heptahydrate; about 12 mg/ml HA, and any concentration of, collagen, botulinum toxin, platelet-rich plasma (PRP), and/or poly-L-lactic acid (PLLA) as determined necessary to achieve aesthetic goals set by the doctor and patient. A product provided herein may, in some instances, contain three, four, five, six, or all of the following: cobalamin (vitamin B12); ascorbic acid (vitamin C); nicotinamide (vitamin B3); thiamine (vitamin B1); pyridoxine HCl (vitamin B6); riboflavin 5-phosphate sodium (vitamin B2); zinc sulfate heptahydrate; and hyaluronic acid (HA), collagen, botulinum toxin, platelet-rich plasma (PRP), and/or poly-L-lactic acid (PLLA).

Presented herein are microneedle devices for transdermal drug delivery of drug compositions.

Microneedle injections are used today for the delivery of substances, such as medicines or cosmetics, through the skin to the body. There are certain advantages of this delivery method over others: it increases absorption of the substance as compared to an oral delivery method by allowing the substance to be introduced to the body without first exposing it to a hostile digestive environment; it decreases the pain associated with delivery of the substance as compared to intramuscular or subcutaneous injections by minimizing trauma to the skin and underlying tissues; and it allows for more rapid diffusion of the delivered substance through the dermis as compared to traditional topical delivery methods, as the microneedles physically penetrate the epidermis.

A microneedle array may be used to deliver a drug directly to the dermis, the second layer of skin. The microneedles in the array puncture the epidermal barrier and deliver the drug directly to the dermis to maximize diffusion to the bloodstream and absorption by the body's active tissues. This delivery method has an advantage over oral delivery because it allows the drug to be absorbed into the body without coming into contact with powerful digestive enzymes of the stomach, over injectable delivery because it is comparatively painless, and over topical delivery because it allows for much greater absorption of the delivered drug (Sullivan S P, Murthy N, Prausnitz M R: Minimally invasive protein delivery with rapidly dissolving polymer microneedles. *Adv Mat.* 2008 March; 20(5):933-938. PubMed PMCID: PMC3519393). The microneedle array will be attached a reservoir that will contain the drugs to be delivered, and this reservoir will itself be attached to contain an apparatus to encourage flow of the drug solution contained in the reservoir through the microneedles and into the skin. Other devices are described, for example, in U.S. Pat. No. 8,257,324.

This reservoir will itself be attached to or contain a means to encourage flow of the drug solutions contained in the reservoir into the skin. Two non-limiting examples of such means are 1) a plate and spring that allows the contained solutions to flow only when the device is tapped into the skin, and 2) a syringe that contains the drug solutions to be delivered and includes a plunger that can be depressed to mechanically drive the solution into the skin.

Microneedle injections are used for percutaneous delivery of bioactive agents, such as medicines or cosmetics, to the body. The advantages of these methods of delivery over others are as follows: it allows the delivered substances to be absorbed by the body without being altered by digestive enzymes, as would occur if an oral delivery method were used; it is relatively painless, as opposed to intramuscular or subcutaneous injections; and it facilitates rapid diffusion of the delivered substance through the dermis, as the microneedles physically penetrate the barrier of the epidermis, which traditional topical delivery methods do not (US Publication Number: US 2012-0296280 A1, entitled "Microneedle and Microneedle Device").

Presented is the method of improving therapeutic outcomes using microneedle delivery of certain bioactive formulations composed of hyaluronic acid, botulinum toxin, collagen, vitamins, minerals, biamtoprost, minoxidil and/or other drugs or solutions such that the therapeutic outcome will be enhanced by using micro needle delivery instead of traditional topical application treatment methods.

Presented herein is a method of improving skin health using microneedle delivery of certain bioactive formulations composed of hyaluronic acid, botulinum toxin, collagen, vitamins, minerals, minoxidil, platelet-rich plasma (PRP), and/or poly-L-lactic acid (PLLA). Improving skin health in a subject comprises, for example, reduction of pore size indicating that skin cells are healthy, increase in moisture content/hydration of the skin resulting in radiance of the skin, easy breakdown of dark spots showing high metabolism and vitamin C, elasticity, natural glow, less sagging, wrinkles, smaller pore sizes, high elasticity, smoothness, high content of moisture, etc.

A microneedle array may be used to deliver hyaluronic acid, botulinum toxin, collagen, vitamins, minerals, minoxidil, platelet-rich plasma (PRP), and/or poly-L-lactic acid (PLLA) or any combination thereof, directly to the dermis, the second layer of skin. The microneedles puncture the epidermal barrier and deliver the desired substances directly to the dermis for faster, more efficient and more effective absorption by the skin. As stated above, this delivery method has an advantage over oral delivery because it allows the desired substances to be absorbed without coming into contact with and risking modification by digestive enzymes, over injectable delivery because it is much less painful, and over topical delivery because it delivers the active substances directly to the dermis and thus prevents them from having to pass through the mostly impermeable epidermis. The formulations composed of hyaluronic acid, botulinum toxin, collagen, vitamins, minerals, minoxidil, platelet-rich plasma (PRP), and/or poly-L-lactic acid (PLLA) act on the skin and/or subcutaneous muscles in order to boost cell rejuvenation and creation, alleviate fine lines and wrinkles, reduce the appearance of scars and blemishes, and improve skin clarity, elasticity, firmness, tone, vitality, and overall health.

Provided herein is a method of aesthetically enhancing a subject in need thereof, comprising administering to the subject an aqueous solution described herein. In one aspect, the solutions for aesthetically enhancing a subject improve skin condition, enhance skin texture, appearance, or a combination thereof. The solutions may improves skin elasticity, luminosity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and reducing fine lines and making wrinkles and facial fine lines appear softer and/or less prominent.

In one aspect, provided herein is a method for improving the cosmetic appearance of a subject, the method comprising: (a) preparing a bioactive formulation, the bioactive formulation comprising at least one cosmetically-bioactive agent, and a pharmaceutically acceptable excipient; (b) loading a reservoir attached to a microneedle delivery system with the bioactive formulation, wherein the microneedle delivery system is capable of delivering sufficient quantities of the bioactive formulation for improving the cosmetic appearance of the subject; (c) applying the bioactive formulation in the microneedle delivery system to the skin surface of the subject where needed, the bioactive formulation only penetrating within the dermal layer, or at a dermal and epidermal junction of the skin; and (d) optionally repeating application of the bioactive formulation in the microneedle delivery system to the skin surface of the subject on a daily basis for up to 30 days. The bioactive agent can be a neurotoxin, hyaluronic acid, or a combination thereof. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method for improving skin quality of a subject, the method comprising: (a) preparing a bioactive formulation, the bioactive formulation comprising at least one cosmetically-bioactive agent, and a pharmaceutically acceptable excipient; (b) loading a reservoir attached to a microneedle delivery system with the bioactive formulation, wherein the microneedle delivery system is capable of delivering sufficient quantities of the bioactive formulation for improving the skin quality of the subject; (c) applying the bioactive formulation in the microneedle delivery system to the skin surface of the subject where needed, the bioactive formulation only penetrating within the dermal layer, or at a dermal and epidermal junction of the skin; and (d) optionally repeating application of the bioactive formulation in the microneedle delivery system to the skin surface of the subject daily basis for up to 30 days. The bioactive agent can be a neurotoxin, hyaluronic acid, or a combination thereof. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method for treating a skin disorder in a subject, the method comprising: (a) preparing a bioactive formulation, the bioactive formulation comprising at least one cosmetically-bioactive agent, and a pharmaceutically acceptable excipient; (b) loading a reservoir attached to a microneedle delivery system with the bioactive formulation, wherein the microneedle delivery system is capable of delivering sufficient quantities of the bioactive formulation for improving skin disorder in the subject; (c) applying the bioactive formulation in the microneedle delivery system to the skin surface of the subject where needed, the bioactive formulation only penetrating within the dermal layer, or at a dermal and epidermal junction of the skin; and (d) optionally repeating application of the bioactive formulation in the microneedle delivery system to the skin surface of the subject on a daily basis for up to 30 days. The bioactive agent can be a neurotoxin, hyaluronic acid, or a combination thereof. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method for reducing surface pores of a subject, the method comprising: (a) preparing a bioactive formulation, the bioactive formulation comprising at least one cosmetically-bioactive agent, and a pharmaceutically acceptable excipient; (b) loading a reservoir attached to a microneedle delivery system with the bioactive formulation, wherein the microneedle delivery system is capable of delivering sufficient quantities of the bioactive formulation for reducing surface pores of the subject; (c) applying the bioactive formulation in the microneedle delivery system to the skin surface of the subject where needed, the bioactive formulation only penetrating within the dermal layer, or at a dermal and epidermal junction of the skin; and (d) optionally repeating application of the bioactive formulation in the microneedle delivery system to the skin surface of the subject on a daily basis for up to 30 days. The bioactive agent can be a neurotoxin, hyaluronic acid, or a combination thereof. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method for reducing surface pores of a subject, the method comprising: (a) preparing a bioactive formulation, the bioactive formulation comprising at least one cosmetically-bioactive agent, and a pharmaceutically acceptable excipient; (b) loading a reservoir attached to a microneedle delivery system with the bioactive formulation, wherein the microneedle delivery system is capable of delivering sufficient quantities of the bioactive formulation for reducing surface pores of the subject; (c) applying the bioactive formulation in the microneedle delivery system to the skin surface of the subject where needed, the bioactive formulation only penetrating within the dermal layer, or at a dermal and epidermal junction of the skin; and (d) optionally repeating application of the bioactive formulation in the microneedle delivery system to the skin surface of the subject on a daily basis for up to 30 days. The bioactive agent can be a neurotoxin, hyaluronic acid, or a combination thereof. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method for improving skin health in a subject, the method comprising: (a) preparing a bioactive formulation, the bioactive formulation comprising at least one cosmetically-bioactive agent, and a pharmaceutically acceptable excipient; (b) loading a reservoir attached to a microneedle delivery system with the bioactive formulation, wherein the microneedle delivery system is capable of delivering sufficient quantities of the bioactive formulation for improving the skin health of the subject; (c) applying the bioactive formulation in the microneedle delivery system to the skin surface of the subject where needed, the bioactive formulation only penetrating within the dermal layer, or at a dermal and epidermal junction of the skin; and (d) optionally repeating application of the bioactive formulation in the microneedle delivery system to the skin surface of the subject on a daily basis for up to 30 days. The bioactive agent can be a neurotoxin, hyaluronic acid, or a combination thereof. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method of treating or ameliorating a disease or one or more symptoms of a condition in a subject in need thereof, the method comprising (a) preparing a bioactive formulation, the bioactive formulation comprising at least one cosmetically-bioactive agent, and a pharmaceutically acceptable excipient; (b) loading a reservoir attached to a microneedle delivery system with the bioactive formulation, wherein the microneedle delivery system is capable of delivering sufficient quantities of the bioactive formulation for treating or ameliorating a disease or one or more symptoms of a condition in the subject; (c) applying the bioactive formulation in the microneedle delivery system to the skin surface of the subject where needed, the bioactive formulation only penetrating within the dermal layer, or at a dermal and epidermal junction of the skin; and (d) optionally repeating application of the bioactive formulation in the microneedle delivery system to the skin surface of the subject on a daily basis for up to 30 days.

The bioactive agent can be a neurotoxin, hyaluronic acid, or a combination thereof. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method for improving the cosmetic appearance of a subject, the method comprising: (a) preparing a bioactive formulation, the bioactive formulation comprising a botulinum toxin, and a hyaluronic acid and a pharmaceutically acceptable excipient; (b) loading a reservoir attached to a microneedle delivery system with the bioactive formulation, wherein the microneedle delivery system is capable of delivering sufficient quantities of the bioactive formulation for improving the cosmetic appearance of the subject; (c) applying the bioactive formulation in the microneedle delivery system to the skin surface of the subject where needed, the bioactive formulation only penetrating within the dermal layer, or at a dermal and epidermal junction of the skin of the skin; and (d) optionally repeating application of the bioactive formulation in the microneedle delivery system to the skin surface of the subject on a daily basis for up to 30 days. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method for improving skin quality of a subject, the method comprising: (a) preparing a bioactive formulation, the bioactive formulation comprising a botulinum toxin, and a hyaluronic acid and a pharmaceutically acceptable excipient; (b) loading a reservoir attached to a microneedle delivery system with the bioactive formulation, wherein the microneedle delivery system is capable of delivering sufficient quantities of the bioactive formulation for improving the cosmetic appearance of the subject; (c) applying the bioactive formulation in the microneedle delivery system to the skin surface of the subject where needed, the bioactive formulation only penetrating within the dermal layer, or at a dermal and epidermal junction of the skin of the skin; and (d) optionally repeating application of the bioactive formulation in the microneedle delivery system to the skin surface of the subject on a daily basis for up to 30 days. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method for treating a skin disorder in a subject, the method comprising: (a) preparing a bioactive formulation, the bioactive formulation comprising a botulinum toxin, and a hyaluronic acid and a pharmaceutically acceptable excipient; (b) loading a reservoir attached to a microneedle delivery system with the bioactive formulation, wherein the microneedle delivery system is capable of delivering sufficient quantities of the bioactive formulation for improving the cosmetic appearance of the subject; (c) applying the bioactive formulation in the microneedle delivery system to the skin surface of the subject where needed, the bioactive formulation only penetrating within the dermal layer, or at a dermal and epidermal junction of the skin of the skin; and (d) optionally repeating application of the bioactive formulation in the microneedle delivery system to the skin surface of the subject on a daily basis for up to 30 days. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method for reducing surface pores of in a subject, the method comprising: (a) preparing a bioactive formulation, the bioactive formulation comprising a botulinum toxin, and a hyaluronic acid and a pharmaceutically acceptable excipient; (b) loading a reservoir attached to a microneedle delivery system with the bioactive formulation, wherein the microneedle delivery system is capable of delivering sufficient quantities of the bioactive formulation for reducing surface pores of the subject; (c) applying the bioactive formulation in the microneedle delivery system to the skin surface of the subject where needed, the bioactive formulation only penetrating within the dermal layer, or at a dermal and epidermal junction of the skin of the skin; and (d) optionally repeating application of the bioactive formulation in the microneedle delivery system to the skin surface of the subject on a daily basis for up to 30 days. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method for reducing surface pores of in a subject, the method comprising: (a) preparing a bioactive formulation, the bioactive formulation comprising a botulinum toxin, and a hyaluronic acid and a pharmaceutically acceptable excipient; (b) loading a reservoir attached to a microneedle delivery system with the bioactive formulation, wherein the microneedle delivery system is capable of delivering sufficient quantities of the bioactive formulation for reducing surface pores the subject; (c) applying the bioactive formulation in the microneedle delivery system to the skin surface of the subject where needed, the bioactive formulation only penetrating within the dermal layer, or at a dermal and epidermal junction of the skin of the skin; and (d) optionally repeating application of the bioactive formulation in the microneedle delivery system to the skin surface of the subject on a daily basis for up to 30 days. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method for improving skin health in a subject, the method comprising: (a) preparing a bioactive formulation, the bioactive formulation comprising a botulinum toxin, and a hyaluronic acid and a pharmaceutically acceptable excipient; (b) loading a reservoir attached to a microneedle delivery system with the bioactive formulation, wherein the microneedle delivery system is capable of delivering sufficient quantities of the bioactive formulation for improving the skin health of the subject; (c) applying the bioactive formulation in the microneedle delivery system to the skin surface of the subject where needed, the bioactive formulation only penetrating within the dermal layer, or at a dermal and epidermal junction of the skin of the skin; and (d) optionally repeating application of the bioactive formulation in the microneedle delivery system to the skin surface of the subject on a daily basis for to 30 days. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method of treating or ameliorating a disease or one or more symptoms of a condition in a subject in need thereof, the method comprising (a) preparing a bioactive formulation, the bioactive formulation comprising a botulinum toxin, and a hyaluronic acid and a pharmaceutically acceptable excipient; (b) loading a reservoir attached to a microneedle delivery system with the bioactive formulation, wherein the microneedle delivery system is capable of delivering sufficient quantities of the bioactive formulation for treating or ameliorating a disease or one or more symptoms of a condition in the subject; (c) applying the bioactive formulation in the microneedle delivery system to the skin surface of the subject where needed, the bioactive formulation only penetrating within the dermal layer, or at a dermal and epidermal junction of the skin of the skin; and (d) optionally repeating application of the bioactive formulation in the microneedle delivery system to the skin surface of the subject on a daily basis for up to 30 days. A botulinum toxin can be botulinum toxin type A, botulinum toxin type B, micro botulinum toxin type A, or micro botulinum toxin type B. In one embodiment, the hyaluronic acid is cross-linked hyaluronic acid, non-cross-linked hyaluronic acid, micro cross-linked hyaluronic acid, micro non-cross-linked hyaluronic acid or a combination thereof. In another embodiment, applying the bioactive formulation comprises only penetrating within the dermal layer, or at a dermal and epidermal junction of the skin with repeated motions on the skin.

In another aspect, provided herein is a method for improving the cosmetic appearance of a subject, the method comprising: (a) preparing a bioactive formulation, the bioactive formulation comprising a neurotoxin, one or more vitamins, one or more minerals, or a combination thereof; (b) loading a reservoir attached to a microneedle delivery system with the bioactive formulation, wherein the microneedle delivery system is capable of delivering sufficient quantities of the bioactive formulation for improving the cosmetic appearance of the subject; (c) applying the bioactive formulation in the microneedle delivery system to the skin surface of the subject with repeated motions on the skin; and (d) optionally repeating application of the bioactive formulation in the microneedle delivery system to the skin surface of the subject on a periodic basis. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In another embodiment, applying the bioactive formulation comprises only penetrating within the dermal layer, or at a dermal and epidermal junction of the skin with repeated motions on the skin.

In another aspect, provided herein is a method for improving skin quality of a subject, the method comprising: (a) preparing a bioactive formulation, the bioactive formulation comprising a neurotoxin, one or more vitamins, one or more minerals, or a combination thereof; (b) loading a reservoir attached to a microneedle delivery system with the bioactive formulation, wherein the microneedle delivery system is capable of delivering sufficient quantities of the bioactive formulation for improving the skin quality of the subject; (c) applying the bioactive formulation in the microneedle delivery system to the skin surface of the subject where needed, the bioactive formulation only penetrating within the dermal layer, or at a dermal and epidermal junction of the skin of the skin; and (d) optionally repeating application of the bioactive formulation in the microneedle delivery system to the skin surface of the subject on a daily basis for up to 30 days. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In another embodiment, applying the bioactive formulation comprises only penetrating within the dermal layer, or at a dermal and epidermal junction of the skin with repeated motions on the skin.

In another aspect, provided herein is a method for treating a skin disorder in a subject, the method comprising: (a) preparing a bioactive formulation, the bioactive formulation comprising a neurotoxin, one or more vitamins, one or more minerals, or a combination thereof; (b) loading a reservoir attached to a microneedle delivery system with the bioactive formulation, wherein the microneedle delivery system is capable of delivering sufficient quantities of the bioactive formulation for improving the skin disorder of the subject; (c) applying the bioactive formulation in the microneedle delivery system to the skin surface of the subject where needed, the bioactive formulation only penetrating within the dermal layer, or at a dermal and epidermal junction of the skin of the skin; and (d) optionally repeating application of the bioactive formulation in the microneedle delivery system to the skin surface of the subject on a daily basis for up to 30 days. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In another embodiment, applying the bioactive formulation comprises only penetrating within the dermal layer, or at a dermal and epidermal junction of the skin with repeated motions on the skin.

In another aspect, provided herein is a method for reducing surface pores of a subject, the method comprising: (a) preparing a bioactive formulation, the bioactive formulation comprising a neurotoxin, one or more vitamins, one or more minerals, or a combination thereof; (b) loading a reservoir attached to a microneedle delivery system with the bioactive formulation, wherein the microneedle delivery system is capable of delivering sufficient quantities of the bioactive formulation for reducing surface pores of the subject; (c) applying the bioactive formulation in the microneedle delivery system to the skin surface of the subject where needed, the bioactive formulation only penetrating within the dermal layer, or at a dermal and epidermal junction of the skin of the skin; and (d) optionally repeating application of the bioactive formulation in the microneedle delivery system to the skin surface of the subject on a daily basis for up to 30 days. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In another embodiment, applying the bioactive formulation comprises only penetrating within the dermal layer, or at a dermal and epidermal junction of the skin with repeated motions on the skin.

In another aspect, provided herein is a method for reducing surface pores of a subject, the method comprising: (a) preparing a bioactive formulation, the bioactive formulation comprising a neurotoxin, one or more vitamins, one or more minerals, or a combination thereof; (b) loading a reservoir attached to a microneedle delivery system with the bioactive formulation, wherein the microneedle delivery system is capable of delivering sufficient quantities of the bioactive formulation for reducing surface pores of the subject; (c) applying the bioactive formulation in the microneedle delivery system to the skin surface of the subject where needed, the bio active formulation only penetrating within the dermal layer, or at a dermal and epidermal junction of the skin of the skin; and (d) optionally repeating application of the bioactive formulation in the microneedle delivery system to the skin surface of the subject on a daily basis for up to 30 days. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In another embodiment, applying the bioactive formulation comprises only penetrating within the dermal layer, or at a dermal and epidermal junction of the skin with repeated motions on the skin.

In another aspect, provided herein is a method for improving skin health in a subject, the method comprising: (a) preparing a bioactive formulation, the bioactive formulation comprising a neurotoxin, one or more vitamins, one or more minerals, or a combination thereof; (b) loading a reservoir attached to a microneedle delivery system with the bioactive formulation, wherein the microneedle delivery system is capable of delivering sufficient quantities of the bioactive formulation for improving the skin health of the subject; (c) applying the bioactive formulation in the microneedle delivery system to the skin surface of the subject where needed, the bioactive formulation only penetrating within the dermal layer, or at a dermal and epidermal junction of the skin of the skin; and (d) optionally repeating application of the bioactive formulation in the microneedle delivery system to the skin surface of the subject on a daily basis for up to 30 days. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In another embodiment, applying the bioactive formulation comprises only penetrating within the dermal layer, or at a dermal and epidermal junction of the skin with repeated motions on the skin.

In another aspect, provided herein is a method of treating or ameliorating a disease or one or more symptoms of a condition in a subject in need thereof, the method comprising (a) preparing a bioactive formulation, the bioactive formulation comprising a neurotoxin, one or more vitamins, one or more minerals, or a combination thereof; (b) loading a reservoir attached to a microneedle delivery system with the bioactive formulation, wherein the microneedle delivery system is capable of delivering sufficient quantities of the bioactive formulation for treating or ameliorating a disease or one or more symptoms of a condition in the subject; (c) applying the bioactive formulation in the microneedle delivery system to the skin surface of the subject where needed, the bioactive formulation only penetrating within the dermal layer, or at a dermal and epidermal junction of the skin of the skin; and (d) optionally repeating application of the bioactive formulation in the microneedle delivery system to the skin surface of the subject on a daily basis for up to 30 days. In one embodiment, the neurotoxin is botulinum toxin or micro botulinum toxin. A botulinum toxin can be botulinum toxin type A, botulinum toxin type B, micro botulinum toxin type A, or micro botulinum toxin type B. In another embodiment, applying the bioactive formulation comprises only penetrating within the dermal layer, or at a dermal and epidermal junction of the skin with repeated motions on the skin.

A bioactive formulation provided herein may comprise botulinum toxin or micro botulinum toxin in an amount of from about 0.01 to about 60 units.

Any of the bioactive formulations provided herein may further comprise one or more vitamins, one or more minerals, one or more retinols, one or more antioxidants, one or more growth factors, a pain reliever, a stabilizer, a preservative, or a combination thereof.

In one embodiment, a bioactive formulation further comprises cyanocobalamin and/or methylcobalamin; ascorbic acid (vitamin C); nicotinamide (vitamin B3); thiamine (vitamin B1); pyridoxine HCl (vitamin B6); riboflavin 5-phosphate sodium (vitamin B2); Zinc sulfate heptahydrate; a pain reliever, a stabilizer, a preservative, or a combination thereof.

In another embodiment, a bioactive formulation further comprises cyanocobalamin and/or methylcobalamin; ascorbic acid (vitamin C); nicotinamide (vitamin B3); thiamine (vitamin B1); pyridoxine HCl (vitamin B6); riboflavin 5-phosphate sodium (vitamin B2); and Zinc sulfate heptahydrate.

In another embodiment, a bioactive formulation comprises: about 5000 mcg cyanocobalamin, about 5000 mcg of methylcobalamin, or a combination thereof; about 1000 mg of ascorbic acid (vitamin C); about 15 mg of zinc; about 6 mg of ahseutasanchin; about 200 IU of vitamin E; about 300 IU of vitamin D; about 150 mcg of selenium; about 50 mg of glutathione (GSH); about 150 mg of anthocyanidin; about 500 mg of omega-3; about 300 mg of EPA; about 300 mg of DHA; about 500 mg of lecithin; about 50 mg of coenzyme Q10 (CoQ10); about 150 mcg of chrome; about 200 mg of magnesium; and about 1 ml q.s., sterile water for injection.

In another embodiment, a bioactive formulation comprises three bioactive agents selected from the group consisting of cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and lidocaine with epinephrine.

In another embodiment, a bioactive formulation comprises four bioactive agents selected from the group consisting of cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and lidocaine with epinephrine.

In another embodiment, a bioactive formulation comprises five bioactive agents selected from the group consisting of cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and lidocaine with epinephrine.

In another embodiment, a bioactive formulation comprises six bioactive agents selected from the group consisting of cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and lidocaine with epinephrine.

In another embodiment, a bioactive formulation comprises cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and lidocaine with epinephrine.

In another embodiment, a bioactive formulation comprises hyaluronic acid, botulinum toxin, collagen, one or more vitamins, one or more minerals biamptoprost, and minoxidil.

In another embodiment, a bioactive formulation comprises vitamin B1 (thiamine), vitamin B2 (riboflavin), vitamin B3 (niacin), vitamin B5 (pantothenic acid), vitamin B6 (pyridoxine), vitamin B7 (biotin), vitamin B12 (cobalamin), hyaluronic acid, collagen, botulinum toxin, platelet-rich plasma, poly-L-lactic acid, lidocaine, epinephrine and folic acid.

In another embodiment, a bioactive formulation comprises: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid (HA), collagen, botulinum toxin, platelet-rich plasma (PRP), poly-L-lactic acid (PLLA), and optionally lidocaine with epinephrine, a chemical stabilizer and optionally a preservative, In another embodiment, a bioactive formulation comprises: from about 1500 mcg to about 5000 mcg of cobalamin (vitamin B12); from about 100 mg to about 200 mg of ascorbic acid (vitamin C); from about 10 mg to about 60 mg of nicotinamide (vitamin B3); from about 2 mg to about 10 mg of thiamine hydrochloride (vitamin B1); from about 0.1 mg to about 0.25 mg of pyridoxine HCl (vitamin B6); from about 2 mg to about 10 mg of riboflavin 5-phosphate sodium (vitamin B2); from about 0.1 mg to about 0.5 mg of zinc sulfate heptahydrate; from about 2.4 mg/ml to about 12 mg/ml hyaluronic acid; a chemical stabilizer; optionally lidocaine with epinephrine; and optionally a preservative.

In another embodiment, a bioactive formulation comprises: from about 4000 to about 5000 mcg of cobalamin (vitamin B12); from about 100 to about 200 mg of ascorbic acid (vitamin C); from about 10 to about 60 mg of nicotinamide (vitamin B3); from about 2 to about 10 mg of thiamine (vitamin B1); from about 0.1 to about 0.2 mg of pyridoxine HCl (vitamin B6); from about 2 to about 10 mg of riboflavin 5-phosphate sodium (vitamin B2); from about 0.1 to about 0.2 mg of zinc sulfate heptahydrate; from about 2.4 to 2.4 mg/ml hyaluronic acid.

In another embodiment, a bioactive formulation comprises: from about 4000 to about 5000 mcg cobalamin (vitamin B12); from about 100 to about 200 mg ascorbic acid (vitamin C); from about 10 to about 60 mg nicotinamide (vitamin B3); from about 2 to about 10 mg thiamine (vitamin B1); from about 0.1 to about 0.2 mg pyridoxine HCl (vitamin B6); from about 2 to about 10 mg riboflavin 5-phosphate sodium (vitamin B2); from about 0.1 to about 0.2 mg zinc sulfate heptahydrate; from about 2.4 to 2.4 mg/ml hyaluronic acid.

In any of the methods described herein, a bioactive formulation may further comprise collagen, platelet-rich plasma, poly-L-lactic acid, or a combination thereof.

In one embodiment, a bioactive formulation is formulated for topical use.

In any of the methods described herein, a bioactive formulation may further comprise a chemical stabilizer such as, for example, gentisic acid.

In any of the methods described herein, a bioactive formulation may further comprise a preservative such as, for example, benzyl alcohol.

In any of the methods described herein, a bioactive formulation may a pH in the range of about from 6.5 to about 7.5, such as, for example, a pH of 7.4.

In any of the methods described herein, a subject being treated may exhibit improvement in one or more symptoms are selected from depression, dementia, fibromyalgia, gastrointestinal disorder, headaches, chronic fatigue syndrome, high stress levels, hyperthyroidism, low energy, impaired memory, hair loss, wound healing, scarring, aging, longevity, wellness purpose, and a combination thereof.

In any of the methods described herein, a subject being treated suffers from a disease selected from beriberi, Wernicke's encephalopathy, ariboflavinosis, pellagra, acne, paresthesia, microcyrtic anemia, or macrocytic anemia.

In any of the methods described herein, a subject being treated may exhibit improvement in skin elasticity, skin regeneration, metabolism, or a combination.

In any of the methods described herein, a bioactive formulation may be delivered painlessly directly tapped into the skin using a repeated motion. The repeated motion can be a circular motion, a patterned motion, a linear motion, a free-style motion, or a cross-hatched motion.

In any of the methods described herein, a bioactive formulation may exhibit characteristics of enhanced or micro delivery through an automated compounding technology.

In any of the methods described herein, collagen may be generated as the bioactive formulation is administered into skin through microneedles with a repeated motion.

In any of the methods described herein, a predetermined dosage of the bioactive formulation is administered into the skin in a manner substantially without absorption of said compounds or formulations via the gastrointestinal tract.

In one aspect, provided herein is a needleless injection device or a prefilled syringe for administration of a bioactive formulation described herein.

In one aspect, provided herein is a system comprising a bioactive formation and a microneedle delivery system, wherein the bioactive formulation comprises at least one cosmetically-bioactive agent, and a pharmaceutically acceptable excipient.

In one aspect, provided herein is a system comprising a bioactive formation and a microneedle delivery system, wherein the bioactive formulation comprises a botulinum toxin, and a hyaluronic acid and a pharmaceutically acceptable excipient.

In one aspect, provided herein is a system comprising a bioactive formation and a microneedle delivery system, wherein the bioactive formulation comprises a neurotoxin, one or more vitamins, one or more minerals, or a combination thereof.

A microneedle delivery system comprises a plurality of microneedles with a channel for liquid form to pass through. The microneedle delivery system can comprise a reservoir chamber with a bioactive formulation. The microneedle delivery system can comprise a plunger that releases the said compounds or formulations. The microneedle delivery system can comprise an optional security material to anti-reverse lock the microneedles and the chamber. The microneedle delivery system can comprise an optional adapter to fit any reservoir chamber. The microneedle delivery system can comprise an optional radio-frequency identification (RFID) smart label connecting to artificial intelligence portal. The microneedle delivery system can comprise an optional cloud-based informatics platform connected to system (big data predictive analytics). The microneedle delivery system can comprise an optional UV blocking agent.

Provided herein is an aqueous solution formulated for delivery using an automated compounding system comprising from about 3000 to 5000 mcg of cyanocobalamin, from about 3000 to 5000 mcg of methylcobalamin, or a combination thereof; from about 700 to about 1000 mg of ascorbic acid (vitamin C); from about 11 to about 15 mg of zinc; from about 4 to about 6 mg of ahseutasanchin; from about 100 to about 200 IU of vitamin E; from about 150 to about 300 IU of vitamin D; from about 100 to about 150 mcg of selenium; from about 30 to about 50 mg of glutathione (GSH); from about 100 to about 150 mg of anthocyanidin; from about 1 to about 500 mg of omega-3; from about 200 to about 300 mg of EPA; from about 200 to about 300 mg of DHA; from about 1 to about 500 mg of lecithin; from about 30 to about 50 mg of coenzyme Q10 (CoQ10); from about 100 to about 150 mcg of chrome; and from about 150 to about 200 mg of magnesium. The aqueous solution may further comprise a chemical stabilizer. The aqueous solution may further comprise a preservative. In one embodiment, the aqueous solution has a pH of about 7.2 to about 7.6, such as, for example, a pH of 7.4.

Provided herein is an automated compounding system comprising a container and a bioactive formation comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg of selenium; from about 30 mg to about 50 mg of glutathione (GSH); from about 100 mg to about 150 mg of anthocyanidin; from about 1 mg to about 500 mg of omega-3; from about 200 mg to about 300 mg of EPA; from about 200 mg to about 300 mg of DHA; from about 1 mg to about 500 mg of lecithin; from about 30 mg to about 50 mg of coenzyme Q10 (CoQ10); from about 100 mcg to about 150 mcg of chrome; and from about 150 mg to about 200 mg of magnesium. The aqueous solution may further comprise a chemical stabilizer. The aqueous solution may further comprise a preservative. In one embodiment, the aqueous solution has a pH of about 7.2 to about 7.6, such as, for example, a pH of 7.4.

Provided herein is a needleless injection device, a pre-filled syringe or AQT combined with an automated compounding system comprising a bioactive formulation comprising from about 3000 to 5000 mcg of cyanocobalamin, from about 3000 to 5000 mcg of methylcobalamin, or a combination thereof; from about 700 to about 1000 mg of ascorbic acid (vitamin C); from about 11 to about 15 mg of zinc; from about 4 to about 6 mg of ahseutasanchin; from about 100 to about 200 IU of vitamin E; from about 150 to about 300 IU of vitamin D; from about 100 to about 150 mcg of selenium; from about 30 to about 50 mg glutathione (GSH); from about 100 to about 150 mg anthocyanidin; from about 1 to about 500 mg of omega-3; from about 200 to about 300 mg of EPA; from about 200 to about 300 mg of DHA; from about 1 to about 500 mg of lecithin; from about 30 to about 50 mg of coenzyme Q10 CoQ10; from about 100 to about 150 mcg of chrome; and from about 150 to about 200 mg of magnesium.

Provided herein is a container comprising a bioactive formulation for delivery using an automated system for compounding pharmaceutical agents for injection treatment of a patient, the bioactive formulation comprising: Cyanocobalamin or methylcobalamin; ascorbic acid (vitamin C); ahseutasanchin; Vitamin E; Vitamin D; selenium; zinc; glutathione (GSH); anthocyanidin; Omega-3; EPA; DHA; lecithin; coenzyme Q10 (CoQ10); chrome; and magnesium, wherein the container optionally comprises a UV-blocking agent which help prevent degradation of components of the compositions.

Provided herein is a container comprising a bioactive formulation for delivery using an automated system for compounding pharmaceutical agents for treatment of a patient, the bioactive formulation comprising: cyanocobalamin, methylcobalamin, or a combination thereof; ascorbic acid (vitamin C); nicotinamide (vitamin B3); thiamine (vitamin B1); mcg pyridoxine HCl (vitamin B6); 4 riboflavin 5-phosphate sodium (vitamin B2); pantothenic acid (vitamin B5); Zinc sulfate heptahydrate; and botulinum Toxin® or micro botulinum toxin, wherein the container optionally comprises a UV-blocking agent which help prevent degradation of components of the compositions. The container may be an ampoule, vial, needleless injection device or pre-filled syringe combined with an automated system for compounding pharmaceutical agents for treatment of a patient.

Provided herein is a method of treating or ameliorating a disease or one or more symptoms of a condition in a subject in need thereof, comprising administering to the subject an aqueous solution comprising from about 3000 to about 5000 mcg of cyanocobalamin, from about 3000 to about 5000 mcg of cyanocobalamin methylcobalamin, or a combination thereof; from about 700 to about 1000 mg of ascorbic acid (vitamin C); from about 11 to about 15 mg of zinc; from about 4 to about 6 mg of ahseutasanchin; from about 100 to about 200 IU of vitamin E; from about 150 to about 300 IU of vitamin D; from about 100 to about 150 mcg of selenium; from about 30 to about 50 mg of glutathione (GSH); from about 100 to about 150 mg of anthocyanidin; from about 1 to about 500 mg of omega-3; from about 200 to about 300 mg of EPA; from about 200 to about 300 mg of DHA; from about 1 to about 500 mg of lecithin; from about 30 to about 50 mg of coenzyme Q10 (CoQ10); from about 100 to about 150 mcg of chrome; and from about 150 to about 200 mg of magnesium; wherein the composition is administered to the patient through delivery using an automated system for compounding pharmaceutical agents for treatment of a patient. The one or more symptoms are selected from depression, headaches, chronic fatigue syndrome, high stress levels, hyperthyroidism, low energy, hair loss, wound healing, scarring, aging, longevity, wellness purpose, and a combination thereof. The disease is selected from beriberi, Wernicke's encephalophay, ariboflavinosis, pellagra, acne, paresthesia, microcyrtic anemia, or macrocytic anemia. Administration of said composition improves skin elasticity, skin regeneration, metabolism, skin health, skin quality, or a combination.

INCORPORATION BY REFERENCE

All publications, patents, and patent applications mentioned in this specification are herein incorporated by reference to the same extent as if each individual publication, patent, or patent application was specifically and individually indicated to be incorporated by reference.

This application incorporates the specification of U.S. application Ser. No. 13/575,525, entitled "MICRO NEEDLE AND MICRO NEEDLE DEVICE", filed on Jul. 26, 2012, and which published as US 2012-0296280 A1 on Nov. 22, 2012, by reference in its entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
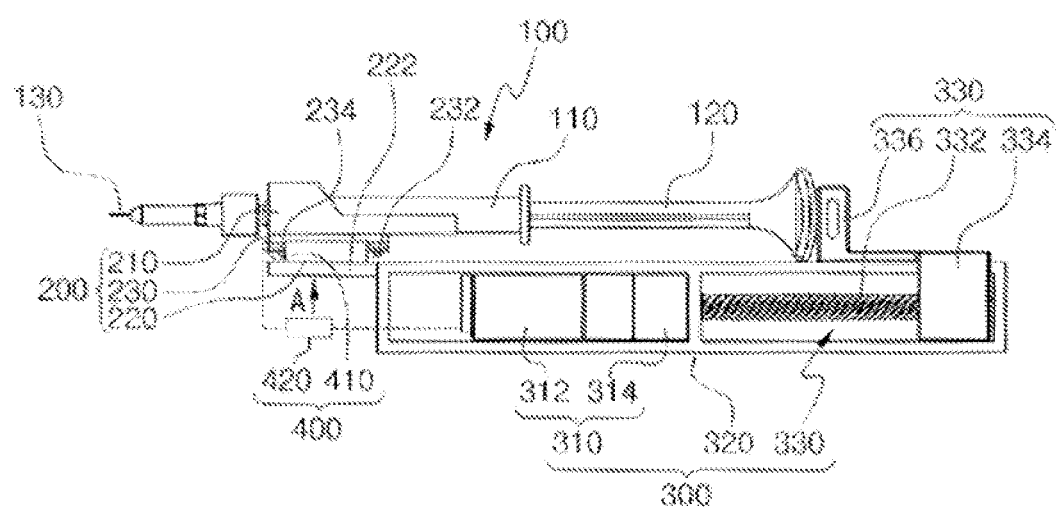
FIG. 1 is a view of a handheld microneedle injection apparatus. The syringe ejection volume is automatically controlled and dispenses into an interchangeable head containing one or several needle.

Unless otherwise defined, all technical and scientific terms used herein have the same meaning as commonly understood by one of ordinary skill in the art. Methods and materials are described herein for use in the present embodiments; other, suitable methods and materials known in the art can also be used. The materials, methods, and examples are illustrative only and not intended to be limiting. In case of conflict, the present specification, including definitions, will control.

Supplementing the diet with additional vitamins and minerals can be a valuable therapy for those with dietary imbalances or different nutritional needs (e.g., for disease prevention). People with dietary imbalances may include those on restrictive diets and those who cannot or will not eat a nutritious diet. Vitamin and mineral supplements are commonly administered to treat specific medical conditions or as general nutritional supplements. Nutritional supplements, often containing vitamins, are used to ensure that adequate amounts of nutrients are obtained if optimal amounts of the nutrients cannot be obtained through a varied diet.

Vitamins, or vital nutrients, and minerals are not synthesized in the human body and must be obtained from the diet for normal metabolic functioning. While they occur naturally in food, vitamins and minerals are often also taken as oral, injectable, or topical supplements to make up for dietary imbalance or to achieve specific physical effects. The most common vitamins used today to promote skin health are A, B, C, D, and E, while the most common minerals used include zinc and calcium. When referring to a vitamin, it would be understood that all chemical forms of the vitamin are contemplated.

B vitamins are a group of water-soluble vitamins that play important roles in cell metabolism. The B vitamins are B1 (thiamine), B2 (riboflavin), B3 (niacin), B5 (pantothenic acid), B6 (pyridoxine), B7 (biotin), B12 (cobalamin) and folic acid. The B vitamins play an important role in many aspects of the body's functioning, and a vitamin B deficiency can have a serious impact on overall health.

Vitamin B supplements are known in the art: such formulations are limited in terms of absorption (oral dosage forms) or may require a hospital visit (IV therapy) at significant cost in terms of time and expense.

Collagen is a type of fibrous protein found most often in the skin, flesh, and connective tissue of vertebrates. In mammals, it is the most abundant protein in the body, and provides structural support for major tissues and organs. In the skin, it is responsible for providing structure, firmness, and smoothness, and it is often a decrease in collagen production that leads to chronic aging. For this reason, collagen is often injected or topically introduced to the skin in attempts to slow or reverse the effects of aging.

Hyaluronic acid (HA) is widely distributed in both prokaryotic and eukaryotic cells. In humans, HA is present in all tissues, especially in the skin (Ref 1). The biological functions of HA include hydration, lubrication of joints, filling capacity, and providing a framework for cells migration[1]. HA also involves in tissue repair, wound healing and immune responses. In terms of cosmetic and aesthetic use, HA plays a role in hydration of the skin and reducing collagen deposition, which leads to reduced scarring. HA-related products are usually used as "dermal fillers".

Due to the lack of suitability of its application with currently formulation availability, HA products are less likely used in treating facial fine lines. Instead, they are more often applied in treatment of deep facial lines (Ref 2). The present invention describe a composition of vitamins and HA for treating facial fine lines, for both intradermal and topical use. The present invention describe a composition of vitamins and HA for treating facial fine lines, for both percutaneous delivery.

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure.

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 2%, 3%, 4%, or 5% of a particular term.

The term "aging-related skin condition" relates to any skin condition or disorder associated with, caused by, or affected by, intrinsic aging and/or extrinsic aging. Aging-related skin conditions that may be treated using the present methods and formulations include, but are not limited to, wrinkles, age spots, sun damage (particularly UV radiation-induced oxidative stress), blemishes, hyperpigmented skin, age spots, increased skin thickness, loss of skin elasticity and collagen content, dry skin, lentigines, melasmas, as well as scars.

Health problems of aging include but not limit to impaired metabolic capacity, Alzheimer's disease, memory loss, impaired cognitive function, Parkinson's disease, incontinence, cancer, cardiovascular disease, arthritis, vision and hearing loss, diabetes, sleep disorders, depression and osteoporosis. The present formulation may relieve aging related health problems by boosting the immune system, promoting energy production, boosting the mood, maintain the central nervous system, detoxifying the body, combating fatigue, promoting cardiovascular function, and exhibiting antioxidant capacity against free radicals.

Improved skin health, includes but is not limited to improved appearance, increased regeneration, increased elasticity, increased anti-oxidative level, reduced photoaging, reduced wrinkles, reduced scarring, reduced bacterial activities including acne, redistribution of fat and/or other content of the skin, reduced number and/or sizes of pores, reduced callusing, reduced sweating and/or body odor through skin, improved scalp health, increased hair density, increased evenness of hair growth, and increased hair strength.

Vitamins and minerals, or vital nutrients, are not synthesized in the human body and must be obtained from the diet for normal metabolic functioning. While they occur naturally in food, vitamins and minerals are often also taken as oral, injectable, or topical supplements to make up for dietary imbalance or to achieve specific physical effects. The most common vitamins used today to promote skin health are A, B, C, D, and E, while the most common minerals used include zinc and calcium.

Vitamin B12, also called cobalamin, is a water-soluble vitamin with a key role in the normal functioning of the brain and nervous system, and for the formation of blood. It is one of the eight B vitamins. It may be involved in the metabolism of every cell of the human body, especially affecting DNA synthesis and regulation, but also fatty acid synthesis and energy production. Vitamin B12 may also be involved in maintenance of the central nervous system and has been used to affect memory loss, Alzheimer's disease, boosting mood, energy and concentration, boost the immune system, and slow aging. Vitamin B12 may also play a role in heart disease, lowering high homocysteine levels (which may contribute to heart disease), male infertility, diabetes, sleep disorders, depression, mental disorders, weak bones (osteoporosis), swollen tendons, AIDS, inflammatory bowel disease, asthma, allergies, a skin disease called vitiligo, preventing cervical and other cancers, and skin infections. Two common forms of Vitamin B12 are cyanocobalamin and methylcobalamin.

Vitamin B12 deficiency may cause macrocytic anemia, fatigue, loss of appetite, loss of balance, weakness, and mood disturbances. It also may cause serious neurologic and neuropsychiatric illness such as paresthesias, ataxia, and memory loss. Vitamin B12 absorption may be impaired at the level of the stomach, where intrinsic factor is produced, or at the level of the terminal ileum, where intrinsic factor bound to vitamin B12 is absorbed.

Niacin and nicotinamide, also known as niacinamide, are forms of vitamin B3. Nicotinamide is the amide of nicotinic acid (vitamin B3/niacin). Nicotinamide is a water-soluble vitamin and is part of the vitamin B group. Nicotinamide may be used for preventing vitamin B3 deficiency and related conditions such as pellagra. Each of these forms of vitamin B3 may be used for schizophrenia, hallucinations due to drugs, Alzheimer's disease and age-related loss of thinking skills, chronic brain syndrome, depression, motion sickness, alcohol dependence, and fluid collection (edema).

Vitamin B1, also known as thiamine, is a water-soluble vitamin and may be utilized for metabolizing carbohydrates and production of energy. Vitamin B1 also may aids in the function of the heart and cardiovascular system and the nervous system.

Vitamin B6, also known as pyridoxine, may be involved in many aspects of macronutrient metabolism, neurotransmitter synthesis, histamine synthesis, hemoglobin synthesis and function and gene expression. Vitamin B6 may assist with cellular metabolism, supports the immune system, with formation of red blood cells and maintenance of healthy brain function. Vitamin B6 may be used for Alzheimer's disease, attention deficit-hyperactivity disorder (ADHD), Down syndrome, autism, diabetes and related nerve pain, sickle cell anemia, migraine headaches, asthma, carpal tunnel syndrome, night leg cramps, muscle cramps, arthritis, allergies, acne and various other skin conditions, and infertility. It is also may be used to treat dizziness, motion sickness, preventing the eye disease age-related macular degeneration (AMD), seizures, convulsions due to fever, and movement disorders (tardive dyskinesia, hyperkinesis, chorea), as well as for increasing appetite and helping people remember dreams. Vitamin B6 may be used for acne, leprosy, attention deficit-hyperactivity disorder (ADHD), memory loss, arthritis, preventing premenstrual headache, improving digestion, protecting against toxins and pollutants, reducing the effects of aging, lowering blood pressure, improving circulation, promoting relaxation, improving orgasm, and preventing cataracts. Vitamin B6 deficiency may cause anemia due to insufficient production of hemoglobin.

Vitamin B2, also known as riboflavin, releases energy from carbohydrates and may be used for preventing low levels of riboflavin (riboflavin deficiency), cervical cancer, and migraine headaches. It also may be used for treating riboflavin deficiency, acne, muscle cramps, burning feet syndrome, carpal tunnel syndrome, and blood disorders such as congenital methemoglobinemia and red blood cell aplasia. It also may be used for increasing energy levels; boosting immune system function; maintaining healthy hair, skin, mucous membranes, and nails; slowing aging; boosting athletic performance; promoting healthy reproductive function; canker sores; memory loss, including Alzheimer's disease; ulcers; burns; alcoholism; liver disease; sickle cell anemia; and treating lactic acidosis brought on by treatment with a class of AIDS medications called NRTI drugs.

The term "vitamin B6" encompasses multiple forms of vitamin B6 suitable for human administration. Several forms of the vitamin are known, but pyridoxal phosphate (PLP; "pyridoxine") is the active form and may be used as a cofactor in many reactions of amino acid metabolism, including transamination, deamination, and decarboxylation. Pyridoxine may be used in enzymatic reactions affecting the release of glucose from glycogen.

Vitamin C, also known as ascorbic acid, is an antioxidant. Vitamin C may be used to protect against free radicals and promote a healthy immune system, wound healing, and forming healthy skin. More specifically, ascorbic acid may be used to prevent and treat scurvy, a disease caused by a lack of vitamin C in the body. People with high intakes of vitamin C from fruits and vegetables may have a lower risk of getting many types of cancer, such as lung, breast, and colon cancer.

Vitamin B5, also known as pantothenic acid, has skincare benefits. For example, it increases the degree of hydration of the skin, reduce the trans-epidermal water loss and keep the elasticity and smoothness of the skin. Vitamin B5 may be used in acne treatments and may be used to reduce itchiness of the skin.

Zinc is an essential mineral found in cells throughout the body. Zinc is required for protein synthesis and collagen formation, and may be used to promote a healthy immune system and assist in wound healing. It may also be used for muscular growth and contraction and to protect the liver from chemical damage such as which can occur with anesthetics or other drugs or toxins. Zinc may also be utilized in bone formation. Zinc deficiency may contribute to fatigue, susceptibility to infection, and slow wound healing.

Ahseutasanchin is a unique pigment belonging to the carotenoid family. It exhibits antioxidant capacity against free radicals.

Vitamin E can boost the immune system and protect people against toxins such as air pollution, neurological disease such as Alzheimer's disease, and diabetes. As an antioxidant, Vitamin E can remove free radicals that damage the cell structure. Owing to this property, another well-known health benefit for Vitamin E is in skin and hair care.

Vitamin D helps intestines absorb nutrients and is essential for calcium utilization, ensuring strong bones and robust immune system.

Selenium displays antioxidant properties that regenerate vitamin C and vitamin E, thereby decreasing the aging of the skin and protect cells from damage. Moreover, selenium also benefits the immune system and protect our body against various infections.

Glutathione (GSH) is an antioxidant which prevent damage to important cellular components caused by free radicals. The strong antioxidant effect of glutathione helps keep cells running smoothly and it also helps the liver remove chemicals that are foreign to the body, such as drugs and pollutants.

Anthocyanidins have a wide range of biological activities including antioxidant, anti-inflammatory, antimicrobial and anti-cancer activities. In addition they display a variety of effects on blood vessels, platelets and lipoproteins able to reduce the risk of coronary heart diseases.

EPA is a form of omega-3 fatty acids which can reduce cellular inflammation.

DHA is a building block of tissue in the brain and retina of the eye. It helps with forming neural transmitters, such as phosphatidylserine, which is important for brain function. EPA and DHA are also well-known for improving skin conditions. Their anti-inflammatory properties help prevent various skin ailments. EPA and DHA can also reduce the damage caused by overexposure to the sun and negative impacts of UV rays.

Lecithin acts as a solvent for cholesterol, triglycerides, and other fats. Therefore, it helps to prevent such ailments as high blood pressure, stroke, heart disease, hardening of the arteries, etc. Also, lecithin plays a vital role in the absorption of nutrients out of the blood stream into the cells.

CoQ10 helps to combat fatigue, boost immune system, fight against free radicals, and keep cells both inside the body and in the skin healthy. The CoQ10 level decreases as people get older, resulting in an impeded ability to produce collagen and elastin, and the loss of collagen and elastin causes our skin wrinkle and sag.

Magnesium can benefit blood pressure and help prevent sudden cardiac arrest and stroke. It also plays a role in detoxification processes and therefore is important for helping to prevent damage from environmental chemicals, heavy metals and other toxins.

Hyaluronic acid (HA) is involved in cartilage resilience and skin repair, has been applied medically for decades for a number of different uses including, for example, cartilage resilience and skin repair. Among the most common of these medical applications employ injectable delivery, for example to treat joint pain, or topical delivery, for example to treat dermatitis. Cosmetically, it is often used as an active agent in facial filler injections to smooth wrinkles and in topical creams and gels to rejuvenate the skin and combat the aging process. Hyaluronic acid includes both cross-linked and non-cross-linked hyaluronic acids.

Micro Hyaluronic Acid FCH is highly stable against heat and pH change, exhibits great permeability to stratum corneum and excellent moisturizing property, and can be used as a cosmetic ingredient. Micro Hyaluronic Acid FCH fits comfortably in skin and has excellent permeability to the stratum corneum. Micro Hyaluronic Acid FCH is ultra low viscosity sodium hyaluronate which has average molecular weight of under 5000. Micro Hyaluronate Acid FCH permeates into skin and shows excellent moisturizing property.

Vitamins and minerals, or vital nutrients, are not synthesized in the human body and must be obtained from the diet for normal metabolic functioning. While they occur naturally in food, vitamins and minerals are often also taken as oral, injectable, or topical supplements to make up for dietary imbalance or to achieve specific physical effects. The most common vitamins used today to promote skin health are A, B, C, D, and E, while the most common minerals used include zinc and calcium.

Bleaching/whitening agents that may be used in the compositions described herein include, but are not limited to, hydroquinone, kojic acid, ascorbic acid, magnesium ascorbyl phosphate or ascorbyl glucosamine, hydroquinone, licorice extract (e.g., *Glycyrrhiza glabra* (licorice) root extract), an alpha MSH antagonist (e.g. undecylenoyl phenylalanine), phytic acid, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid and mixtures thereof.

Retinols used in the compositions described herein include, but are not limited to, retinoic acid.

Collagen is a type of fibrous protein found most often in the skin, flesh, and connective tissue of vertebrates. In mammals, it is the most abundant protein in the body, and provides structural support for major tissues and organs. In the skin, it is responsible for providing structure, firmness, and smoothness, and it is often a decrease in collagen production that leads to chronic aging. For this reason, collagen is often injected or topically introduced to the skin in attempts to slow or reverse the effects of aging (Varani J, Dame M K, Rittie L, Fligiel S E G, Kang S, Fisher G J, Voorhees J J: Decreased Collagen Production in Chronically Aged Skin. Am J Pathol. 2006 June; 168(6):1861-1868. PubMed PMCID: PMC1606623).

Botulinum toxin, a neurotoxic protein, is used cosmetically and therapeutically for treatment of facial lines and wrinkles, upper motor neuron syndrome, excessive sweating, cervical dystonia, chronic migraine, and overactive bladder. The toxin is generally injected into the subcutaneous muscles at the target areas, and works by temporarily (for a period of six weeks to eight months, depending on the location and the dose) inhibiting the release of acetylcholine at the neuromuscular junction and thus paralyzing the muscles achieve the desired affects (BOTOX (onabotulinumtoxinA) [prescribing information]. Irvine, Calif. Allergan, Inc. January 2013). Botulinum toxin refers to any botulinum toxin, including but not limited to botulinum toxin type A, botulinum toxin type B, botulinum toxin type C1, botulinum toxin type D, botulinum toxin type E, botulinum toxin type F and botulinum toxin type G. Botulinum toxin type A includes, for example, Botox, Dysport and Xeomin. Botulinum toxin type B includes, for example, MyoBloc. Botulinum toxin may be provided in a liquid or powder form. A powdered form may be, for example, a sterile, lyophilized preparation. Lyophilized preparations may be reconstituted prior to application. Alternatively, botulinum toxin may be provided as a sterilized pre-dissolved solution. Botulinum toxin may be formulated in an amount of about 0.01 to about 60 units.

"MicroBotox" or "Purtox" as used herein, refers to instances when diluted Botox is injected in multiple very small doses in a treated area. The effects of the Botox are more evenly spread over the areas treated and the risks of having areas over-treated is reduced. Use of MicroBotox generally results in a more natural look (i.e., less frozen) and the dosage of Botox administered is reduced. For some patients suffering from recalcitrant acne problems, MicroBotox (referred to as "mesoBotox" when used in this situation) can be injected very superficially into the facial skin. Following dilution, microBotox may be formulated in an amount of 0.1 to about 99% of the compositions. For example, one would use 0.1 to about 100 units of onabotulinum toxin diluted with at least 2.5 cc of saline.

Minoxidil is a vasodilator that was originally administered orally as a treatment for hypertension, but was found to have the additional effect of slowing hair loss and promoting hair growth. It is now a common topical treatment for androgenic hair loss, and is thought to achieve hair regrowth by increasing the blood flow (and thus the availability of oxygen and vital nutrients) to the hair follicles, stimulating them to resume normal functioning (Olsen E A, Whiting D, Bergfeld W, Miller J, Hordinsky M, Wanser R, Zhang P, Kohut B: A multicenter, randomized, placebo-controlled, double-blind clinical trial of a novel formulation of 5% minoxidil topical foam versus placebo in the treatment of androgenetic alopecia in men. *J Am Acad Dermatol.* 2007 Aug. 29. PubMed PMID: 17761356).

Platelet-rich plasma (PRP) is blood plasma that has been enriched by platelets, and is prepared by separating whole blood via centrifugation and then collecting the plasma-rich layers that emerge. Because it has five times the baseline platelet concentration of plasma (~100,000 platelets per microliter as opposed to the baseline of ~20,000 platelets per microliter), it contains a number of different growth factors (proteins that stimulate tissue growth, the release of which can be induced by the addition of thrombin and calcium chloride. PRP injections have been used clinically for several years as a treatment for nerve, bone, and muscle injuries, and have been used cosmetically to reverse damage to the skin and to promote dermal strength and rejuvenation (Borrione P, Gianfrancesco A D, Pereira M T, Pigozzi F: Platelet-rich plasma in muscle healing. *Am J Phys Med Rehabil.* 2010 October; 89(10):854-61. PubMed PMID: 20855985).

Poly-L-lactic Acid (PLLA) is a type of dermal filler used in the treatment of facial lipoatrophy (the gradual loss of facial fat, generally due to aging). PLLA, upon entering the skin, provides immediate structural support to the skin and also promotes the neo-synthesis of collagen, hiding sunken areas. Over time, it converted by the body into harmless lactic acid, gradually transferring the load to the recently synthesized collagen (SCULPTRA Aesthetic (injectable poly-L-lactic acid) [prescribing information]. Bridgewater, N.J. Sanofi-Aventis U.S. LLC. May 2012).

Biamtoprost is a prostaglandin prodrug that is administered topically to control the progression of Glaucoma and to treat ocular hypertension. Since 2008, the application of this drug has evolved to encompass a cosmetic formulation for the lengthening and darkening of eyelashes and is thought to confer an improved appearance by delivering biamtoprost—a growth stimulating analog—circambient to the hair follicles at the edge of the eyelid.

Compositions

Compositions described herein may be used to treat one or more clinical manifestations and/or symptoms of a disease or skin condition, hair loss, wound healing and/or prevention of scarring, or for anti-aging, longevity and wellness purpose described herein. The present inventors have identified new compositions that may be injected into a patient to improve skin elasticity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and making wrinkles appear softer and/or less prominent, etc.

The compositions and methods provided herein provide vitamin compositions formulated for administration to the skin surface in combination with a microneedle device, the compositions being applied topically, intradermally or a combination of both routes of administration. The compositions and methods provided herein provide vitamin compositions formulated for administration to the skin surface in combination with a microneedle device, the compositions being applied percutaneously. For vitamin supplementation to be effective, the supplements provided to a patient should contain suitable amounts of the various micronutrients required by the patient. Suitable amounts can be determined by the skilled physician and depend on the age, gender and general health of the patient, as well as a surgical, or other procedure planned for the patient. In some cases, it may also be determined based upon the degree and type of trauma a patient has suffered. Previous nutritional status may also be considered when determining a suitable amount of nutritional supplementation. In addition, patient compliance is a very important factor, since nutritional supplementation is not effective if the patient does not receive the supplements and is much less effective if the patient does not receive the proper dose on a consistent basis.

Improved skin health or improved skin quality, as used above, includes but is not limited to improved appearance, increased regeneration, increased elasticity, increased anti-oxidative level, reduced photo-aging, reduced wrinkles, reduced scarring, reduced bacterial activities including acne, redistribution of fat and/or other content of the skin, reduced number and/or sizes of pores, reduced callusing, reduced sweating and/or body odor through skin, improved scalp health, increased hair density, increased evenness of hair growth, and increased hair strength.

Vitamin supplementation may be provided in easy-to-use and clearly labeled packs to increase patient compliance. The supplements may be administered to any patient needing, e.g., improvement of a skin condition such as, for example, skin elasticity, skin regeneration, metabolism, etc. For example, patient populations include, but are not limited to: men over age fifty, and women over age fifty. That is, patients whose skin may not be as elastic or firm as a younger patient. However, it would be understood that humans under the age of fifty may also experience changes in their skin which would benefit from administration of a composition described herein. For example, a patient who may also be administered a composition described herein may be one who had plastic or reconstructive surgery, which population includes any human of any age. In addition to these compositions, a treating physician may add other disease-specific supplements as the patient's condition warrants. In addition to the pre-packaged nutritional supplements, the dispensing physician may add one or more other specific supplements, if needed.

Compositions comprising hyaluronic acid, botulinum toxin, collagen, vitamins, minerals biamptoprost and/or minoxidil act on the skin and/or subcutaneous muscles in order to boost cell rejuvenation and creation, alleviate fine lines and wrinkles, reduce the appearance of scars and blemishes, and improve skin clarity, elasticity, firmness, tone, vitality, and overall health.

Active ingredients which may be used in a composition (formulation) described herein include, but are not limited to, B1 (thiamine), B2 (riboflavin), B3 (niacin), B5 (pantothenic acid), B6 (pyridoxine), B7 (biotin), B12 (cobalamin), hyaluronic acid, collagen, botulinum toxin, platelet-rich plasma, poly-L-lactic acid, lidocaine, epinephrine and folic acid.

In one embodiment, an aqueous solution adapted for human administration, comprises an therapeutically effective amount of one or more of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid (HA), collagen, botulinum toxin, platelet-rich plasma (PRP), poly-L-lactic acid (PLLA), and optionally lidocaine with epinephrine, a chemical stabilizer and optionally a preservative, wherein the aqueous solution is formulated for topical use and/or dermal administration. The pH of the solution can be adjusted to a pH that is physiologically acceptable for administration to humans. In one embodiment, a composition contains only three of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only four of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only five of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only six of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains all of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and lidocaine with epinephrine.

Vitamin B12 may be included in a composition in amount to improve skin appearance. In one embodiment, the aqueous solution comprises from about 2500 mcg to about 3000 mcg cobalamin, from about 3500 mcg to about 4500 mcg cobalamin, or from about 4000 mcg to about 5000 mcg cobalamin. In one embodiment, vitamin B12 is present in a composition in an amount of about 5000 mg. One would appreciate that vitamin B12 exists in multiple forms suitable for therapeutic use, including cyanocobalamin and methylcobalamin, which forms are contemplated for use herein.

Vitamin B3 (nicotinamide) may be included in a composition in amount of from about 10 mg to about 60 mg, from about 20 mg to about 50 mg, from or about 30 mg to about 40 mg. In one embodiment, thiamine is present in a composition in an amount of about 40 mg.

Vitamin B1 may be included in a composition in an amount of from about 2 mg to about 10 mg, from about 4 mg to 8 mg, or from about 4 mg to about 6 mg. In one embodiment, thiamine is present in a composition in an amount of about 6 mg.

Vitamin B6 (pyridoxine) may be included in a composition in an amount of from about 0 mg to about 0.2 mg, about 0 mg to 0.1 mg, or about 0.1 mg to about 0.2 mg. Pyridoxine may be administered as pyridoxine HCl. In one embodiment, pyridoxine HCl is present in a composition in an amount of about 0.1 mg.

Vitamin B2 (Riboflavin 5-phosphate sodium) may be included in a composition in an amount of from about 2 mg to about 10 mg, from about 4 mg to about 8 mg or from about 4 mg to about 6 mg. In one embodiment, riboflavin 5-phosphate sodium is present in a composition in an amount of about 3.6 mg.

Vitamin C (ascorbic acid) may be included in a composition in an amount of from about 50 mg to about 300 mg, from about 100 mg to about 250 mg, or from about 150 mg to about 200 mg. In one embodiment, ascorbic acid is present in a composition in an amount of about 200 mg.

Zinc sulfate heptahydrate may be included in a composition in an amount of from about 0 mg to about 0.2 mg, or from about 0 mg to about 0.1 mg. In one embodiment, zinc is present in a composition in an amount of about 0.1 mg.

Hyaluronic Acid may be included in a composition in an amount of from about 2.4 mg/ml to about 12 mg/ml, or from about 4.8 mg/ml to about 7.2 mg/ml. In one embodiment, the HA is present in a composition in an amount of about 4.8 mg/ml.

Collagen, botulinum toxin, platelet-rich plasma, and poly-L-lactic acid may be included in a composition in any amount as considered necessary to achieve the aesthetic goals set by the patient and doctor.

The aqueous solution may optionally include lidocaine with epinephrine, which are used for providing patient comfort and reduce bruising.

The aqueous solution may optionally include a chemical stabilizer. Any number of chemical stabilizers may be used to stabilize and increase shelf-life of formulations. In one aspect, a chemical stabilizer is employed to retard or prevent degradation of a vitamin compound induced by ultraviolet light. Chemical stabilizers include, but are not limited to, a chelating agent, an anti-oxidant, an acidifying agent or gentisic acid. In one embodiment, the chemical stabilizer is an acidifying agent or gentisic acid.

Solution formulations can be prepared by dissolving these components in an aqueous buffer known in the art of solution formulations such as phosphate buffers and/or citrate buffers.

Provided herein is a product comprising an aqueous solution adapted for human administration, comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg of selenium; from about 30 mg to about 50 mg of glutathione (GSH); from about 100 mg to about 150 mg of anthocyanidin; from about 1 mg to about 500 mg of omega-3; from about 200 mg to about 300 mg of EPA; from about 200 mg to about 300 mg of DHA; from about 1 mg to about 500 mg of lecithin; from about 30 mg to about 50 mg of coenzyme Q10 (CoQ10); from about 100 mcg to about 150 mcg of chrome; from about 150 mg to about 200 mg of magnesium; optionally a chemical stabilizer; and optionally a preservative, wherein the aqueous solution is formulated for administration via a microneedle device.

In one embodiment, the product comprises about 5000 mcg of cyanocobalamin and/or methylcobalamin; about 1000 mg of ascorbic acid (vitamin C); about 15 mg of zinc; about 6 mg of ahseutasanchin; about 200 IU of vitamin E; about 300 IU of vitamin D; about 150 mcg of selenium; about 50 mg of glutathione (GSH); about 150 mg of anthocyanidin; about 500 mg of omega-3; about 300 mg of EPA; about 300 mg of DHA; about 500 mg of lecithin; about 50 mg of coenzyme Q10 (CoQ10); about 150 mcg of chrome; and about 200 mg of magnesium.

In one embodiment, a chemical stabilizer for use in the aqueous solution is gentisic acid. A chemical stabilizer may be present in the formulation in an amount of from about 0.01% to about 2%.

In one embodiment, a preservative is benzyl alcohol. A preservative may be present in the formulation in an amount of from about 0.01% to about 2%.

In one embodiment, the product has a pH from about 7.2 and 7.6, for example, a pH of 7.4.

In one embodiment, the cobalamin is selected from cyanocobalamin or methylcobalamin.

Also provided herein is an aqueous solution formulated for administration via microneedle device comprising from about 3000 to 5000 mcg of cyanocobalamin, from about 3000 to 5000 mcg of methylcobalamin, or a combination thereof; from about 700 to about 1000 mg of ascorbic acid (vitamin C); from about 11 to about 15 mg of zinc; from about 4 to about 6 mg of ahseutasanchin; from about 100 to about 200 IU of vitamin E; from about 150 to about 300 IU of vitamin D; from about 100 to about 150 mcg of selenium; from about 30 to about 50 mg of glutathione (GSH); from about 100 to about 150 mg of anthocyanidin; from about 1 to about 500 mg of omega-3; from about 200 to about 300 mg of EPA; from about 200 to about 300 mg of DHA; from about 1 to about 500 mg of lecithin; from about 30 to about 50 mg of coenzyme Q10 (CoQ10); from about 100 to about 150 mcg of chrome; and from about 150 to about 200 mg of magnesium;

The aqueous solution may further comprise a chemical stabilizer.

The aqueous solution may further comprise a preservative.

The aqueous solution may have a pH of about 7.2 to about 7.6 such as, for example, a pH of 7.4.

The aqueous solution of claim 8, wherein the cobalamin is selected from cyanocobalamin and methylcobalamin, and a combination thereof.

Bioactive compositions suitable for intradermal administration and topical use can include sterile aqueous solutions (where water soluble) or dispersions and sterile powders for the extemporaneous preparation of sterile injectable solutions or dispersion. The compositions may be sterile and should be fluid to the extent that easy injectability exists. It should be stable under the conditions of manufacture and storage and must be preserved against the contaminating action of microorganisms such as bacteria and fungi.

Sterile injectable solutions can be prepared by incorporating the aforementioned components in the required amount in an appropriate solvent with one or a combination of ingredients enumerated above, as required, followed by filtered sterilization, UV sterilization, gamma irradiation, e-beam sterilization, or any other conventional method for sterilization of fluids. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

The pH of the solution can be adjusted to a pH that is physiologically acceptable for administration to humans.

There exists a need for combination use with compositions mentioned above. The present inventors have developed formulations for combining with AQT technology that serve aesthetic enhancement purposes. Included in the formulations described herein are new formulations that are designed to improve skin quality, skin condition, enhance skin texture, and appearance. For example, administration of a composition provided herein may improve skin elasticity, luminosity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and reducing fine lines and making wrinkles and facial fine lines appear softer and/or less prominent.

In one aspect, provided herein is an aqueous solution adapted for human administration, the aqueous solution comprising from about 1500 mcg to about 5000 mcg of cobalamin (vitamin B12); from about 100 mg to about 200 mg of ascorbic acid (vitamin C); from about 10 mg to about 60 mg of nicotinamide (vitamin B3); from about 2 mg to about 10 mg of thiamine hydrochloride (vitamin B1); from about 0.1 mg to about 0.25 mg of pyridoxine HCl (vitamin B6); from about 2 mg to about 10 mg of riboflavin 5-phosphate sodium (vitamin B2); from about 0.1 mg to about 0.5 mg of zinc sulfate heptahydrate; from about 2.4 mg/ml to about 12 mg/ml HA; optionally lidocaine with epinephrine; a chemical stabilizer; and optionally a preservative. Preservatives and chemical stabilizers may be added to the compositions in an amount of from about 0.01% and about 2% of the total volume. This composition alone or in combination with other compounds is delivered into the skin using AQT technology for added benefit of skin quality and health.

In one embodiment, the product comprises an aqueous solution comprising about 5000 mcg of cobalamin (vitamin B12); about 200 mg of ascorbic acid (vitamin C); about 40 mg of nicotinamide (vitamin B3); about 6 mg of thiamine (vitamin B1); about 0.1 mg of pyridoxine HCl (vitamin B6); about 3.6 mg of riboflavin 5-phosphate sodium (vitamin B2); about 0.1 mg of zinc sulfate heptahydrate; about 12 mg/ml HA, and any concentration of, collagen, botulinum toxin, platelet-rich plasma (PRP), and/or poly-L-lactic acid (PLLA) as determined necessary to achieve aesthetic goals set by the doctor and patient. A product provided herein may, in some instances, contain three, four, five, six, or all of the following: cobalamin (vitamin B12); ascorbic acid (vitamin C); nicotinamide (vitamin B3); thiamine (vitamin B1); pyridoxine HCl (vitamin B6); riboflavin 5-phosphate sodium (vitamin B2); zinc sulfate heptahydrate; and hyaluronic acid (HA), collagen, botulinum toxin, platelet-rich plasma (PRP), and/or poly-L-lactic acid (PLLA). This composition alone or in combination with other compounds is delivered into the skin using AQT technology for added benefit of skin quality and health.

In one embodiment, an aqueous solution adapted for human administration, comprises a therapeutically effective amount of one or more of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid (HA), collagen, botulinum toxin, platelet-rich plasma (PRP), poly-L-lactic acid (PLLA), and optionally lidocaine with epinephrine, a chemical stabilizer and optionally a preservative, wherein the aqueous solution is formulated for delivery using AQT technology. The pH of the solution can be adjusted to a pH that is physiologically acceptable for administration to humans. In one embodiment, a composition contains only three of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only four of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only five of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only six of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains all of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and lidocaine with epinephrine.

In one aspect, provided herein is an aqueous solution of functional vitamins and minerals adapted for human administration, the aqueous solution comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg lecithin; from about 30 mg to 50 mg of coenzyme Q10 (CoQ10); from about 100 mcg to 150 mcg of chrome; from about 150 mg to 200 mg of magnesium; optionally a chemical stabilizer; and optionally a preservative, wherein the aqueous solution is formulated for delivery using AQT technology. In order to achieve personalized benefits at a maximal level, one may add or remove few of the components listed above, as well as increasing or reducing the dose. Preservatives and chemical stabilizers may be added to the compositions in an amount of from about 0.01% and about 2% of the total volume.

Provided herein is a composition for delivering micro botulinum toxins alone or with other component combinations using Aquagold (AQT) technology: (a) whereby certain botulinum toxin is freeze- or vacuum-dried and pre-filled in an AQT technology chamber and a user reconstitutes and dilutes an injectable dose of the said botulinum toxin into AQT proper micro botulinum toxin with saline or vitamins or hyaluronic acids or other component combinations; and/or (b) whereby a liquid product of botulinum toxin is diluted with dextrose solution an amount of from 0.2 to 3 ml per up to 49 units of botulinum toxin alone or combined with other components such as vitamins and hyaluronic acid with AQT technology whereby said botulinum toxin is diluted about 50% (up to .+−.49%).

The aqueous solution is formulated in physiological saline and adjusted to an acceptable pH in the range of about 6.5 to about 7.5, thereby neutralizing the solution to minimize pain upon transdermal delivery. Such an aqueous formulation may be optionally supplemented with a preservative (e.g., from about 0.01% to about 2% benzyl alcohol) and/or a chemical stabilizer (e.g., from about 0.01% to about 2% gentisic acid), depending on the anticipated shelf life and environmental factors that could lead to degradation. Painless delivery allows for exclusion of lidocaine or other similar compounds to reduce pain or have an anesthetic effect before non-invasive laser treatments.

Provided herein is a composition for administering dilute hyaluronic acid (cross-linked and/or non-cross-linked or combinations of both) alone or other component combinations using AQT technology, comprising:

(a) A combination of micro botulinum toxin, vitamins and/or micro hyaluronic acid. One example of this combination may be combined mesotherapeutic agents such as micro botulinum toxins and micro hyaluronic acid.

(b) A combination therapeutics may be applied to traditional areas of treatment for aesthetic application including the forehead, neck, lower eyelids, cheek, periorbitally, and intraorbitally as well as non-traditional areas such as décolleté, dorsum of hand, knees, elbows, ankles, lower buttocks, lower part of breasts, chin etc. Age-related skin features such as brow and frown lines, crow's feet, and bunny lines may be targeted to achieve aesthetic goals.

(c) With the specific use of botulinum Toxin® or Micro-botulinum Toxin®, the eyes and chin should typically receive the manufacturer's equivalent of up to 100 units after dilution. The forehead may receive up to 25 units of botulinum toxin after dilution, typically diluted into approximately 1 mL of conveying liquid such as saline.

(d) For patients recovering from a surgical procedure, the application of botulinum toxins has been shown to be beneficial to healing and resultant scar appearance. Those undergoing a breast augmentation or reduction surgery often have scars underneath the breast at the site of the incision. Application of up to 28 units of botulinum Toxin® or Micro-botulinum Toxin® to a scar site of approximately 20 cm under each breast can lead to positive cosmetic outcomes.

Provided herein is a composition for delivering minoxidil and/or bimatoprost alone or with combinations using AQT technology. Vitamin B12 may be added for additional benefits.

Provided herein is a composition for delivering betulinic acid alone or with other compounds using AQT technology for melanoma and other similar conditions.

Provided herein is a composition for delivering hydroxyaryl alkyl ketones and their isosteric derivatives alone or with other compounds using AQT technology for skin whitening or treating sun spots and tan lines.

Provided herein is a composition for delivering retinoic acid alone or with other compounds using AQT technology.

Provided herein is a composition delivering adapalene alone or with other compounds using AQT technology.

Provided herein is a composition for delivering lidocaine and/or tetracaine and/or other similar anesthetic agents alone or in combinations with other components using AQT technology.

Provided herein is a composition for delivering etanercept and/or adalimubab or other similar biologics alone or in combinations with other components using AQT technology.

Provided herein is a composition for delivering functional vitamins and minerals alone or in combinations with other components using AQT technology.

Provided herein is a composition for delivering a wound care hydrogel comprising S-sulfonated keratin associated with a water soluble polymer through hydrogen bonding and further comprising a protein cross-linking agent alone or with other compounds using AQT technology.

The term "cobalamin" or "vitamin B12" encompass multiple forms of vitamin B12 suitable for human administration, including cyanocobalamin or methylcobalamin.

The term "Aquagold technology" or "AQT technology" refers to but is not limited to a method of delivering a composition prepared for direct delivery into the skin by repeated stamping motion of a microneedle device on the skin. Volumes formulated for AQT technology include, but are not limited to, about 0.1 ml, about 0.2 ml, about 0.3 ml, about 0.4 ml, about 0.5 ml, about 0.6 ml, about 0.7 ml, about 0.8 ml, about 0.9 ml, about 1.0 ml or above.

In one embodiment, a non-limiting example of an aqueous solution formulated for delivery of functional vitamins and minerals using AQT technology comprises from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium.

In another aspect, the aqueous solution can have a pH of from about 6.0 to about 8.0. In another aspect, the aqueous solution can have a pH of about 7.4.

Also provided herein is an AQT system combined with a needleless injector or a prefilled syringe comprising an aqueous solution formulated for administration with the needleless injector, the aqueous solution comprising from about 3000 to 5000 mcg of cyanocobalamin, from about 3000 to 5000 mcg of methylcobalamin, or a combination thereof; from about 700 to about 1000 mg of ascorbic acid (vitamin C); from about 11 to about 15 mg of zinc; from about 4 to 6 mg of ahseutasanchin; from about 100 to 200 IU of vitamin E; from about 150 to 300 IU of vitamin D; from about 100 to 150 mcg of selenium; from about 30 to 50 mg of glutathione (GSH); from about 100 to 150 mg of anthocyanidin; from about 1 to about 500 mg of omega-3; from about 200 to 300 mg of EPA; from about 200 to 300 mg of DHA; from about 1 to 500 mg of lecithin; from about 30 to 50 mg of coenzyme Q10 (CoQ10); from about 100 to 150 mcg of chrome; from about 150 to 200 mg of magnesium.

In another embodiment, an AQT system combined with a needleless injector or a prefilled syringe comprises an aqueous solution which comprises from about 3000 to 5000 mcg of cyanocobalamin, from about 3000 to 5000 mcg of methylcobalamin, or a combination thereof; from about 700 to about 1000 mg of ascorbic acid (vitamin C); from about 11 to about 15 mg of zinc; from about 4 to 6 mg of ahseutasanchin; from about 100 to 200 IU of vitamin E; from about 150 to 300 IU of vitamin D; from about 100 to 150 mcg of selenium; from about 30 to 50 mg of glutathione (GSH); from about 100 to 150 mg of anthocyanidin; from about 1 to about 500 mg of omega-3; from about 200 to 300 mg of EPA; from about 200 to 300 mg of DHA; from about 1 to about 500 mg of lecithin; from about 30 to 50 mg of coenzyme Q10 (CoQ10); from about 100 to 150 mcg of chrome; from about 150 to 200 mg of magnesium; where the pH has been adjusted to about 7.4.

Also provided herein is a container, which contains a composition prepared for direct application using AQT technology. Volumes to be considered for packaging in the containers include, but are not limited to, about 0.1 ml, about 0.2 ml, about 0.3 ml, about 0.4 ml, about 0.5 ml, about 0.6 ml, about 0.7 ml, about 0.8 ml, about 0.9 ml, about 1.0 ml, about 1.1 ml, about 1.2 ml, about 1.3 ml, about 1.4 ml, about 1.5 ml, about 1.6 ml, about 1.7 ml, about 1.8 ml, about 1.9 ml, about 2.0 ml, about 2.1 ml, about 2.2 ml, about 2.3 ml, about 2.4 ml, about 2.5 ml, about 2.6 ml, about 2.7 ml, about 2.8 ml, about 2.9 ml, about 3.0 ml, about 3.1 ml, about 3.2 ml, about 3.3 ml, about 3.4 ml, about 3.5 ml, about 3.6 ml, about 3.7 ml, about 3.8 ml, about 3.9 ml, about 4.0 ml, about 4.1 ml, about 4.2 ml, about 4.3 ml, about 4.4 ml, about 4.5 ml, about 4.6 ml, about 4.7 ml, about 4.8 ml, about 4.9 ml, and about 5.0 ml. In one aspect, the container comprises a composition comprising an aqueous solution formulated for delivery using AQT technology, the aqueous solution comprising cyanocobalamin or/and methylcobalamin; ascorbic acid (vitamin C); ahseutasanchin; Vitamin E; Vitamin D; selenium; zinc; glutathione (GSH); anthocyanidin; omega-3; EPA; DHA; lecithin; CoQ10; chrome; and magnesium. In one aspect, the container is an ampoule, vial, a needleless injection device or pre-filled syringe combined with AQT technology. Containers described herein may, in some instances, contain a UV-blocking agent which helps prevent degradation of components of the compositions.

In one embodiment, a container comprises from about 3000 mcg to 5000 mcg cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium. In another embodiment, a container comprises an aqueous solution which comprises from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium, where the pH has been adjusted to about 7.4.

Solution formulations can be prepared by dissolving these components in an aqueous buffer known in the art of solution formulations such as phosphate buffers and/or citrate buffers.

In one aspect, provided herein is an aqueous vitamin composition which is specifically tailored for needleless injection. A vitamin composition which is specifically tailored for needleless injection generally refers to a composition prepared for direct needless injection of a substance in an appropriate amount.

Supplement compositions suitable for microneedle injection can include sterile aqueous solutions (where water soluble) or dispersions and sterile powders for the extemporaneous preparation of sterile injectable solutions or dispersion. The compositions may be sterile and should be fluid to the extent that easy injectability exists. It should be stable under the conditions of manufacture and storage and must be preserved against the contaminating action of microorganisms such as bacteria and fungi.

Sterile injectable solutions can be prepared by incorporating the vitamin component in the required amount in an appropriate solvent with one or a combination of ingredients enumerated above, as required, followed by filtered sterilization, UV sterilization, gamma irradiation, e-beam sterilization, or any other conventional method for sterilization of fluids. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Provided herein a composition described herein for patients undergoing or who have undergone a surgical procedure, or who have suffered an injury. The composition is designed to prevent deficiencies in vitamin B needed for optimal health and healing during the period pre- and post-surgery or for general application and to enable the patient receiving the composition to achieve maximum healing and rapid recovery from a procedure or injury. In one embodiment, surgery is plastic surgery or reconstructive surgery.

Acceptable carriers are physiologically acceptable to the administered patient and retain the therapeutic properties of the compounds with/in which it is administered. Acceptable carriers and their formulations are and generally described in, for example, Remington' pharmaceutical Sciences (18th Edition, ed. A. Gennaro, Mack Publishing Co., Easton, Pa. 1990). One exemplary carrier is physiological saline. The phrase "pharmaceutically acceptable carrier" as used herein means an acceptable material, composition or vehicle, such as a liquid or solid filler, diluent, excipient, and/or solvent involved in carrying or transporting the subject compounds from the administration site of one organ, or portion of the body, to another organ, or portion of the body. Each carrier is acceptable in the sense of being compatible with the other ingredients of the formulation and not injurious to a subject to whom it is administered. Nor should an acceptable carrier alter the specific activity of the subject compounds.

Compositions described herein may be used to treat one or more clinical manifestations and/or symptoms aging related skin problems. The present inventors have identified new compositions that may be applied topically or injected into a patient to improve skin elasticity, skin luminosity, skin regeneration, skin hydration, smoothness and/or softness of skin (i.e., making the skin feel smoother and softer following treatment); the overall appearance of skin; evening out skin tone and texture; clarity and/or radiance of skin; making the skin look younger; and making wrinkles and fine lines appear softer and/or less prominent, etc.

The compositions and methods provided herein provide neurotoxin formulated for topical use or intradermal administration. For a composition comprising a neurotoxin to be effective, the compositions provided to a patient should contain suitable amounts of neurotoxin and other formulation ingredients required by the patient. In one embodiment, the neurotoxin is botulinum toxin or micro botulinum toxin.

Suitable amounts can be determined by the skilled physician and depend on the age, gender and general health of the patient, as well as a surgical, or other procedure planned for the patient. In some cases, it may also be determined based upon the degree of the aging stage. Previous skincare procedures may also be considered when determining a suitable amount of aesthetic composition. In addition, patient compliance is a very important factor, since aesthetic composition is not effective if the patient does not receive the composition and is much less effective if the patient does not receive the proper dose on a consistent basis. Provided herein are compositions comprising a neurotoxin for treating facial fine lines, for both intradermal and topical use. These compositions represent an advance over compositions currently on the market; the commercial products are less likely used in treating facial fine lines, but rather, are more often applied in treatment of deep facial lines.

The compositions and methods provided herein provide ahseutasanchin formulated for topical use or intradermal administration. For an ahseutasanchin composition to be effective, the compositions provided to a patient should contain suitable amounts of ahseutasanchin and other formulation ingredients required by the patient. Suitable amounts can be determined by the skilled physician and depend on the age, gender and general health of the patient, as well as a surgical, or other procedure planned for the patient. In some cases, it may also be determined based upon the degree of the aging stage. Previous skincare procedures may also be considered when determining a suitable amount of aesthetic composition. In addition, patient compliance is a very important factor, since aesthetic composition is not effective if the patient does not receive the composition and is much less effective if the patient does not receive the proper dose on a consistent basis. Provided herein are composition of ahseutasanchin for treating facial fine lines, for both intradermal and topical use. These compositions represent an advance over compositions currently on the market; the commercial products are less likely used in treating facial fine lines, but rather, are more often applied in treatment of deep facial lines.

The aqueous solution may optionally include lidocaine with epinephrine, which are used for providing patient comfort and reduce bruising.

The aqueous solution may optionally include a chemical stabilizer. Any number of chemical stabilizers may be used to stabilize and increase shelf-life of formulations. In one aspect, a chemical stabilizer is employed to retard or prevent degradation of a vitamin compound induced by ultraviolet light. Chemical stabilizers include, but are not limited to, a chelating agent, an anti-oxidant, an acidifying agent or gentisic acid. In one embodiment, the chemical stabilizer is an acidifying agent or gentisic acid.

Solution formulations can be prepared by dissolving these components in an aqueous buffer known in the art of solution formulations such as phosphate buffers and/or citrate buffers.

Vitamin and HA compositions suitable for intradermal administration and topical use can include sterile aqueous solutions (where water soluble) or dispersions and sterile powders for the extemporaneous preparation of sterile injectable solutions or dispersion. The compositions may be sterile and should be fluid to the extent that easy injectability exists. It should be stable under the conditions of manufacture and storage and must be preserved against the contaminating action of microorganisms such as bacteria and fungi.

Sterile injectable solutions can be prepared by incorporating the vitamin component and HA in the required amount in an appropriate solvent with one or a combination of ingredients enumerated above, as required, followed by filtered sterilization, UV sterilization, gamma irradiation, e-beam sterilization, or any other conventional method for sterilization of fluids. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Compositions described herein may be used to treat one or more clinical manifestations and/or symptoms aging related skin problems. The present inventors have identified new compositions that may be applied topically or injected into a patient to improve skin elasticity, skin luminosity, skin regeneration, skin hydration, smoothness and/or softness of skin (i.e., making the skin feel smoother and softer following treatment); the overall appearance of skin; evening out skin tone and texture; clarity and/or radiance of skin; making the skin look younger; and making wrinkles and fine lines appear softer and/or less prominent, etc. The compositions and methods provided herein provide bioactive compositions formulated for topical use or intradermal administration.

For these compositions to be effective, the compositions provided to a patient should contain suitable amounts of the various active agents required by the patient. Suitable amounts can be determined by the skilled physician and depend on the age, gender and general health of the patient, as well as a surgical, or other procedure planned for the patient. In some cases, it may also be determined based upon the degree of the aging stage. Previous skincare procedures may also be considered when determining a suitable amount of aesthetic composition. In addition, patient compliance is a very important factor, since aesthetic composition is not effective if the patient does not receive the composition and is much less effective if the patient does not receive the proper dose on a consistent basis.

Active ingredients which may be used in a composition (formulation) described herein include, but are not limited to, B1 (thiamine), B2 (riboflavin), B3 (niacin), B5 (pantothenic acid), B6 (pyridoxine), B7 (biotin), B12 (cobalamin), hyaluronic acid, collagen, botulinum toxin, platelet-rich plasma, poly-L-lactic acid, lidocaine, epinephrine and folic acid.

In one embodiment, an aqueous solution adapted for human administration, comprises an therapeutically effective amount of one or more of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid (HA), collagen, botulinum toxin, platelet-rich plasma (PRP), poly-L-lactic acid (PLLA), and optionally lidocaine with epinephrine, a chemical stabilizer and optionally a preservative, wherein the aqueous solution is formulated for topical use and/or dermal administration. The pH of the solution can be adjusted to a pH that is physiologically acceptable for administration to humans. In one embodiment, a composition contains only three of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only four of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only five of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains only six of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and/or lidocaine with epinephrine. In another embodiment, a composition contains all of the following: cobalamin (vitamin B12), ascorbic acid (vitamin C), nicotinamide (vitamin B3), thiamine (vitamin B1), pyridoxine HCl (vitamin B6), riboflavin 5-phosphate sodium (vitamin B2), zinc sulfate heptahydrate, hyaluronic acid, collagen, botulinum toxin, platelet-rich plasma, poly-L-lactic acid and lidocaine with epinephrine.

Vitamin B12 may be included in a composition in amount to improve skin appearance. In one embodiment, the aqueous solution comprises from about 2500 mcg to about 3000 mcg cobalamin, from about 3500 mcg to about 4500 mcg cobalamin, or from about 4000 mcg to about 5000 mcg cobalamin. In one embodiment, vitamin B12 is present in a composition in an amount of about 5000 mg. One would appreciate that vitamin B12 exists in multiple forms suitable for therapeutic use, including cyanocobalamin and methylcobalamin, which forms are contemplated for use herein.

Vitamin B3 (nicotinamide) may be included in a composition in amount of from about 10 mg to about 60 mg, from about 20 mg to about 50 mg, from or about 30 mg to about 40 mg. In one embodiment, thiamine is present in a composition in an amount of about 40 mg.

Vitamin B1 may be included in a composition in an amount of from about 2 to about 10 mg, from about 4 mg to 8 mg, or from about 4 mg to about 6 mg. In one embodiment, thiamine is present in a composition in an amount of about 6 mg.

Vitamin B6 (pyridoxine) may be included in a composition in an amount of from about 0 mg to about 0.2 mg, about 0 mg to 0.1 mg, or about 0.1 mg to about 0.2 mg. Pyridoxine may be administered as pyridoxine HCl. In one embodiment, pyridoxine HCl is present in a composition in an amount of about 0.1 mg.

Vitamin B2 (Riboflavin 5-phosphate sodium) may be included in a composition in an amount of from about 2 mg to about 10 mg, from about 4 mg to about 8 mg or from about 4 mg to about 6 mg. In one embodiment, riboflavin 5-phosphate sodium is present in a composition in an amount of about 3.6 mg.

Vitamin C (ascorbic acid) may be included in a composition in an amount of from about 50 mg to about 300 mg, from about 100 mg to about 250 mg, or from about 150 mg to about 200 mg. In one embodiment, ascorbic acid is present in a composition in an amount of about 200 mg.

Zinc sulfate heptahydrate may be included in a composition in an amount of from about 0 mg to about 0.2 mg, or from about 0 mg to about 0.1 mg. In one embodiment, zinc is present in a composition in an amount of about 0.1 mg.

Hyaluronic Acid may be included in a composition in an amount of from about 2.4 mg/ml to about 12 mg/ml, or from about 4.8 mg/ml to about 7.2 mg/ml. In one embodiment, the HA is present in a composition in an amount of about 4.8 mg/ml. In one instance, hyaluronic acid will be in any concentration, from 0.01% to 100%, and can be administered via the micro needle array either independently or in conjunction with the aforementioned bioactive formulations. The formulations will consist of vitamins, minerals, hyaluronic acid, botulinum toxin, collagen, minoxidil, bimatoprost or any compatible combinations thereof that are believed to improve skin health.

Collagen, botulinum toxin, platelet-rich plasma, and poly-L-lactic acid may be included in a composition in any amount as considered necessary to achieve the aesthetic goals set by the patient and doctor or prefilled by a manufacturer.

The aqueous solution may optionally include lidocaine with epinephrine, which are used for providing patient comfort and reduce bruising.

The aqueous solution may optionally include a chemical stabilizer. Any number of chemical stabilizers may be used to stabilize and increase shelf-life of formulations. In one aspect, a chemical stabilizer is employed to retard or prevent degradation of a vitamin compound induced by ultraviolet light. Chemical stabilizers include, but are not limited to, a chelating agent, an anti-oxidant, an acidifying agent or gentisic acid. In one embodiment, the chemical stabilizer is an acidifying agent or gentisic acid.

Solution formulations can be prepared by dissolving these components in an aqueous buffer known in the art of solution formulations such as phosphate buffers and/or citrate buffers.

Bioactive compositions suitable for intradermal administration and topical use can include sterile aqueous solutions (where water soluble) or dispersions and sterile powders for the extemporaneous preparation of sterile injectable solutions or dispersion. The compositions may be sterile and should be fluid to the extent that optimal delivery exists. It should be stable under the conditions of manufacture and storage and must be preserved against the contaminating action of microorganisms such as bacteria and fungi.

Sterile injectable solutions can be prepared by incorporating the aforementioned components in the required amount in an appropriate solvent with one or a combination of ingredients enumerated above, as required, followed by filtered sterilization, UV sterilization, gamma irradiation, e-beam sterilization, or any other conventional method for sterilization of fluids. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

The amount of optional preservative in any of the compositions described herein may be about 0.05%, about 0.1%, about 0.25%, about 0.5%, about 0.75%, about 1.0%, about 1.25%, about 1.5%, about 1.75%, about 2%, or any integer therein.

The amount of optional chemical stabilizer in any of the compositions described herein may be about 0.05%, about 0.1%, about 0.25%, about 0.5%, about 0.75%, about 1.0%, about 1.25%, about 1.5%, about 1.75%, about 2%, or any integer therein. In one embodiment, the volume that is injected is about 1 ml.

An acceptable pH range for the formulations described herein are those which are acceptable for administration to human patients and include, but are not limited to, from about pH 6.0 to about pH 8.0, from about pH 6.5 to about pH 7.5, and from about pH 7.0 to about pH 7.5. In one embodiment, the pH is adjusted to about 7.4.

Compositions described herein may be used to treat one or more clinical manifestations and/or symptoms of aging-related health problems, skin conditions, hair loss, wound healing and/or prevention of scarring, or for anti-aging, longevity and wellness purpose described herein. The present inventors have identified new compositions that may be administered as disclosed herein into a patient to relieve aging related health problems by boosting the immune system, promoting energy production, boosting the mood, maintain the central nervous system, detoxifying the body, combating fatigue, promoting cardiovascular function, and exhibiting antioxidant capacity against free radicals, etc. The compositions and methods provided herein provide vitamin compositions formulated for administration as disclosed herein. It is important to note that in order to achieve personalized benefits at maximal level, one may add or remove few of the components listed above, as well as increasing or reducing the dose. For vitamin supplementation to be effective, the supplements provided to a patient should contain suitable amounts of the various micronutrients required by the patient. Suitable amounts can be determined by the skilled physician and depend on the age, gender and general health of the patient, as well as a surgical, or other procedure planned for the patient. In some cases, it may also be determined based upon the degree and type of trauma a patient has suffered. Previous nutritional status may also be considered when determining a suitable amount of nutritional supplementation. In addition, patient compliance is a very important factor, since nutritional supplementation is not effective if the patient does not receive the supplements and is much less effective if the patient does not receive the proper dose on a consistent basis. Vitamin supplementation may be provided in easy-to-use and clearly labeled packs to increase patient compliance. The supplements may be administered to any patient needing, e.g., improvement of an aging-related skin condition such as, for example, skin elasticity, skin regeneration, metabolism, etc. For example, patient populations include, but are not limited to: men over age fifty, and women over age fifty. That is, patients whose skin may not be as elastic or firm as a younger patient. However, it would be understood that humans under the age of fifty may also experience changes in their skin which would benefit from administration of a composition described herein. For example, a patient who may also be administered a composition described herein may be one who had plastic or reconstructive surgery, which population includes any human of any age. In addition to these compositions, a treating physician may add other disease-specific supplements as the patient's condition warrants. In addition to the pre-packaged nutritional supplements, the dispensing physician may add one or more other specific supplements, if needed.

In one embodiment, an aqueous solution adapted for human administration, comprises an therapeutically effective amount of following ingredients: cyanocobalamin or/and methylcobalamin (vitamin B12), ascorbic acid (vitamin C), zinc, ahseutasanchin, vitamin E, vitamin D, selenium, glutathione (GSH), anthocyanidin, omega-3, EPA, DHA, lecithin, CoQ10, chrome, and magnesium. The pH of the solution can be adjusted to a pH that is physiologically acceptable for administration to humans.

Vitamin B12 may be included in a composition to increase metabolism, or improve aging-related skin conditions. In one embodiment, the aqueous solution comprises from about 3000 to about 5000 mcg of cyanocobalamin or/and methylcobalamin. One would appreciate that vitamin B12 exists in multiple forms suitable for therapeutic use, including cyanocobalamin and methylcobalamin, which forms are contemplated for use herein.

Vitamin C (ascorbic acid) is included in a composition in an amount of from about 700 to about 1000 mg. Zinc is included in a composition in an amount of from about 11 mg to about 15 mg. Ahseutasanchin is included in a composition in an amount of from about 4 mg to about 6 mg. Vitamin E is included in a composition in an amount of from about 100 IU to about 200 IU. Vitamin D is included in a composition in an amount of from about 150 IU to about 300 IU. Selenium is included in a composition in an amount of from about 100 mcg to about 150 mcg. Glutathione (GSH) is included in a composition in an amount of from about 30 mg to about 50 mg. Anthocyanidin is included in a composition in an amount of from about 100 mg to about 150 mg. Omega-3 is included in a composition in an amount about 1 mg to about 500 mg. EPA is included in a composition in an amount of from 200 mg to about 300 mg. DHA is included in a composition in an amount of from about 200 mg to about 300 mg. Lecithin is included in a composition in an amount about 1 mg to about 500 mg. CoQ10 is included in a composition in an amount of from about 30 mg to about 50 mg. Chrome is included in a composition in an amount of from about 100 mcg to about 150 mcg. Magnesium is included in a composition in an amount of from about 150 mg to about 200 mg.

Embodiments described herein relate to vitamin supplement compositions formulated for administration as disclosed herein and methods of use thereof.

Supplementing the diet with additional vitamins and minerals can be a valuable therapy for those with dietary imbalances or different nutritional needs (e.g., for disease prevention). People with dietary imbalances may include those on restrictive diets and those who cannot or will not eat a nutritious diet. Vitamin and mineral supplements are commonly administered to treat specific medical conditions or as general nutritional supplements. Nutritional supplements, often containing vitamins, are used to ensure that adequate amounts of nutrients are obtained if optimal amounts of the nutrients cannot be obtained through a varied diet.

B vitamins are a group of water-soluble vitamins that play important roles in cell metabolism. The B vitamins are B1 (thiamine), B2 (riboflavin), B3 (niacin), B5 (pantothenic acid), B6 (pyridoxine), B7 (biotin), B12 (cobalamin) and folic acid. The B vitamins play an important role in many aspects of the body's functioning, and a vitamin B deficiency can have a serious impact on overall health.

Vitamin B supplement formulations are limited in terms of absorption (oral dosage forms) or may require a hospital visit (IV therapy) at significant cost in terms of time and expense.

There exists a need for vitamin formulations. The present inventors have developed new vitamin compositions formulated for administration as disclosed herein, which can be used to treat or ameliorate a disease or one or more symptoms associated with a vitamin deficiency or other condition in a human patient. Included in the formulations described herein are new injectable formulations that are designed to improve aging-related conditions and appearance, e.g., from inside, rather than topical administration of, for example, a cream agent. For example, administration of a composition provided herein may improve aging-related health condition, such as boosting the immune system, promoting energy production, boosting the mood, maintain the central nervous system, detoxifying the body, combating fatigue, promoting cardiovascular function, and exhibiting antioxidant capacity against free radicals, evening out skin tone and texture, making the skin look younger, making wrinkles appear softer and/or less prominent.

In one aspect, provided herein is an aqueous solution adapted for human administration, the aqueous solution comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium; optionally a chemical stabilizer; and optionally a preservative, wherein the aqueous solution is formulated for administration as disclosed herein. In order to achieve personalized benefits at maximal level, one may add or remove few of the components listed above, as well as increasing or reducing the dose. Preservatives and chemical stabilizers may be added to the compositions in an amount of from about 0.01% and about 2% of the total volume.

The term "needleless injection" or "microneedle injection" refers but is not limited to compositions prepared for needleless injection of a substance. Volumes formulated for injection include, but are not limited to, about 0.1 ml, about 0.2 ml, about 0.3 ml, about 0.4 ml, about 0.5 ml, about 0.6 ml, about 0.7 ml, about 0.8 ml, about 0.9 ml, about 1.0 ml or above.

In one embodiment, a non-limiting example of an aqueous solution formulated for injection with the microneedle devices disclosed herein comprises from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium.

In another aspect, the aqueous solution can have a pH of from about 6.0 to about 8.0. In another aspect, the aqueous solution can have a pH of about 7.4.

Also provided herein is a needleless injector or a prefilled syringe or an AQT microneedle system comprising an aqueous solution formulated for administration, the aqueous solution comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to 500 mg of lecithin; from about 30 mg to 50 mg of coenzyme Q10 CoQ10; from about 100 mcg to 150 mcg of chrome; from about 150 mg to 200 mg of magnesium.

In another embodiment, a needleless injector or a prefilled syringe comprises an aqueous solution which comprises from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 CoQ10; from about 100 mcg to 150 mcg of chrome; from about 150 mg to 200 mg of magnesium; where the pH has been adjusted to about 7.4.

In another embodiment, a needleless injector or a prefilled syringe comprises a bioactive formulation comprising hyaluronic acid, botulinum toxin, collagen, vitamins, minerals, minoxidil, platelet-rich plasma (PRP), and/or poly-L-lactic acid (PLLA) or a combination thereof.

Also provided herein is a container that contains a composition prepared for administration as disclosed herein.

In one aspect, provided herein is a container comprising a bioactive formulation for delivery using an automated system for compounding pharmaceutical agents for needleless injection treatment of a patient, the bioactive formulation comprising Cyanocobalamin or methylcobalamin; ascorbic acid (vitamin C); ahseutasanchin; Vitamin E; Vitamin D; selenium; zinc; glutathione (GSH); anthocyanidin; Omega-3; EPA; DHA; lecithin; CoQ10; chrome; and magnesium, wherein the container optionally comprises a UV-blocking agent which help prevent degradation of components of the compositions.

In another aspect, provided herein is a container comprising a bioactive formulation for delivery using an automated system for compounding pharmaceutical agents for needleless injection treatment of a patient, the bioactive formulation comprising cyanocobalamin, methylcobalamin, or a combination thereof; ascorbic acid (vitamin C); nicotinamide (vitamin B3); thiamine (vitamin B1); mcg pyridoxine HCl (vitamin B6); 4 riboflavin 5-phosphate sodium (vitamin B2); pantothenic acid (vitamin B5); Zinc sulfate heptahydrate; and botulinum Toxin® or micro botulinum toxin, wherein the container optionally comprises a UV-blocking agent which help prevent degradation of components of the compositions.

In another aspect, provided herein is a container comprising a bioactive formulation for delivery using an automated system for compounding pharmaceutical agents for needleless injection treatment of a patient, the bioactive formulation comprising hyaluronic acid, botulinum toxin, collagen, vitamins, minerals, minoxidil, platelet-rich plasma (PRP), and/or poly-L-lactic acid (PLLA) or a combination thereof.

The container can be an ampoule, vial or pre-filled syringe combined with an automated system for compounding pharmaceutical agents for needleless injection treatment of a patient.

Volumes to be considered for packaging in the containers include, but are not limited to, about 0.1 ml, about 0.2 ml, about 0.3 ml, about 0.4 ml, about 0.5 ml, about 0.6 ml, about 0.7 ml, about 0.8 ml, about 0.9 ml, about 1.0 ml, about 1.1 ml, about 1.2 ml, about 1.3 ml, about 1.4 ml, about 1.5 ml, about 1.6 ml, about 1.7 ml, about 1.8 ml, about 1.9 ml, about 2.0 ml, about 2.1 ml, about 2.2 ml, about 2.3 ml, about 2.4 ml, about 2.5 ml, about 2.6 ml, about 2.7 ml, about 2.8 ml, about 2.9 ml, about 3.0 ml, about 3.1 ml, about 3.2 ml, about 3.3 ml, about 3.4 ml, about 3.5 ml, about 3.6 ml, about 3.7 ml, about 3.8 ml, about 3.9 ml, about 4.0 ml, about 4.1 ml, about 4.2 ml, about 4.3 ml, about 4.4 ml, about 4.5 ml, about 4.6 ml, about 4.7 ml, about 4.8 ml, about 4.9 ml, and about 5.0 ml. In one aspect, the container comprises a composition comprising an aqueous solution formulated for administration, the aqueous solution formulated for needleless injection, a AQT microneedle system, a prefilled syringe or other delivery methods, comprising cyanocobalamin or/and methylcobalamin; ascorbic acid (vitamin C); ahseutasanchin; Vitamin E; Vitamin D; selenium; zinc; glutathione (GSH); anthocyanidin; Omega-3; EPA; DHA; lecithin; CoQ10; chrome; and magnesium. In one aspect, the container is an ampoule, vial, a needleless injection device or pre-filled syringe. Containers described herein may, in some instances, contain a UV-blocking agent which helps prevent degradation of components of the compositions. In one embodiment, a container comprises from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium. In another embodiment, a container comprises an aqueous solution which comprises about 3000 mcg to about 5000 mcg cyanocobalamin or/and methylcobalamin; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium, where the pH has been adjusted to about 7.4.

The aqueous solution may optionally include a chemical stabilizer. Any number of chemical stabilizers may be used to stabilize and increase shelf-life of formulations. In one aspect, a chemical stabilizer is employed to retard or prevent degradation of a vitamin compound induced by ultraviolet light. Chemical stabilizers include, but are not limited to, a chelating agent, an anti-oxidant, an acidifying agent or gentisic acid. In one embodiment, the chemical stabilizer is an acidifying agent or gentisic acid.

The aqueous solution may optionally include a preservative. Any number of preservatives may be used to increase shelf-life of the formulations disclosed herein. Non-limiting examples of preservatives are, for example, benzyl alcohol, methylparaben, propylparaben, Benzyl alcohol, thimerosal, m-Cresol and methyl p-hydroxybenzoate. In one embodiment, benzyl alcohol also acts as a mild anesthetic potential that may mitigate the pain of injection.

Solution formulations can be prepared by dissolving these components in an aqueous buffer known in the art of solution formulations such as phosphate buffers and/or citrate buffers.

Supplement compositions suitable for microneedle injection, or an AQT microneedle system, can include sterile aqueous solutions (where water soluble) or dispersions and sterile powders for the extemporaneous preparation of sterile injectable solutions or dispersion. The compositions may be sterile and should be fluid to the extent that easy inject ability exists. It should be stable under the conditions of manufacture and storage and must be preserved against the contaminating action of microorganisms such as bacteria and fungi.

Sterile injectable solutions can be prepared by incorporating the vitamin component in the required amount in an appropriate solvent with one or a combination of ingredients enumerated above, as required, followed by filtered sterilization, UV sterilization, gamma irradiation, e-beam sterilization, or any other conventional method for sterilization of fluids. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Provided herein a composition described herein for patients undergoing or who have undergone a surgical procedure, or who have suffered an injury. The composition is designed to prevent deficiencies in vitamin B needed for optimal health and to promote healing during the period pre- and post-surgery or for general application and to enable the patient receiving the composition to achieve maximum healing and rapid recovery from a procedure or injury. In one embodiment, surgery is plastic surgery or reconstructive surgery. Acceptable carriers are physiologically acceptable to the administered patient and retain the therapeutic properties of the compounds with/in which it is administered. Acceptable carriers and their formulations are and generally described in, for example, Remington' pharmaceutical Sciences (18th Edition, ed. A. Gennaro, Mack Publishing Co., Easton, Pa. 1990). One exemplary carrier is physiological saline. The phrase "pharmaceutically acceptable carrier" as used herein means an acceptable material, composition or vehicle, such as a liquid or solid filler, diluent, excipient, and/or solvent involved in carrying or transporting the subject compounds from the administration site of one organ, or portion of the body, to another organ, or portion of the body. Each carrier is acceptable in the sense of being compatible with the other ingredients of the formulation and not injurious to a subject to whom it is administered. Nor should an acceptable carrier alter the specific activity of the subject compounds.

Provided herein is an aqueous solution containing the following ingredients: from about 3000 to 5000 mcg cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 KT to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium; and about 1 ml q.s., sterile water for injection. The aqueous solution is formulated in physiological saline and adjusted to an acceptable pH, thereby minimizing any injecting pain beyond the needle prick. The aqueous solution may be optionally supplemented with a preservative (e.g., benzyl alcohol) and/or a chemical stabilizer (e.g., gentisic acid), depending on anticipated shelf-life.

The amount of optional preservative may be about 0.05%, about 0.1%, about 0.25%, about 0.5%, about 0.75%, about 1.0%, about 1.25%, about 1.5%, about 1.75%, about 2%, or any integer therein.

The amount of optional chemical stabilizer may be about 0.05%, about 0.1%, about 0.25%, about 0.5%, about 0.75%, about 1.0%, about 1.25%, about 1.5%, about 1.75%, about 2%, or any integer therein. In one embodiment, the volume that is injected is about 1 ml.

An acceptable pH range for the formulations described herein are those which are acceptable for administration to human patients and include, but are not limited to, from about pH 6.0 to about pH 8.0, from about pH 6.5 to about pH 7.5, and from about pH 7.0 to about pH 7.5. In one embodiment, the pH is adjusted to about 7.4.

Provided herein is an aqueous solution containing the following ingredients: from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium; and about 1 ml q.s., sterile water for injection. The aqueous solution is formulated in physiological saline and adjusted to an acceptable pH, thereby minimizing any injecting pain beyond the needle prick. The aqueous solution may be optionally supplemented with a preservative (e.g., benzyl alcohol) and/or a chemical stabilizer (e.g., gentisic acid), depending on anticipated shelf-life.

The amount of optional preservative may be about 0.05%, about 0.1%, about 0.25%, about 0.5%, about 0.75%, about 1.0%, about 1.25%, about 1.5%, about 1.75%, about 2%, or any integer therein.

The amount of optional chemical stabilizer may be about 0.05%, about 0.1%, about 0.25%, about 0.5%, about 0.75%, about 1.0%, about 1.25%, about 1.5%, about 1.75%, about 2%, or any integer therein. In one embodiment, the volume that is injected is about 1 ml.

An acceptable pH range for the formulations described herein are those which are acceptable for administration to human patients and include, but are not limited to, from about pH 6.0 to about pH 8.0, from about pH 6.5 to about pH 7.5, and from about pH 7.0 to about pH 7.5. In one embodiment, the pH is adjusted to about 7.4.

Provided herein a composition described herein for patients undergoing or who have undergone a surgical procedure, or who have suffered an injury. The composition is designed to prevent deficiencies in vitamin B needed for optimal health and to promote healing during the period pre- and post-surgery or for general application and to enable the patient receiving the composition to achieve maximum healing and rapid recovery from a procedure or injury. In one embodiment, surgery is plastic surgery or reconstructive surgery.

Compositions described herein may be used to treat one or more clinical manifestations and/or symptoms of aging-related health problems, skin conditions, hair loss, wound healing and/or prevention of scarring, or for anti-aging, longevity and wellness purpose described herein. The present inventors have identified new compositions that may be injected into a patient to relieve aging related health problems by boosting the immune system, promoting energy production, boosting the mood, maintain the central nervous system, detoxifying the body, combating fatigue, promoting cardiovascular function, and exhibiting antioxidant capacity against free radicals, etc. The compositions and methods provided herein provide vitamin compositions formulated for delivery using AQT technology.

In certain instances, to achieve personalized benefits at maximal level, one may add or remove few of the components of a formulation described herein, increasing or reducing the dose, or a combination thereof. In one embodiment, for vitamin supplementation to be effective, the supplements provided to a patient can contain suitable amounts of the various micronutrients required by the patient.

Vitamin supplementation may be provided in easy-to-use and clearly labeled packs to increase patient compliance. The supplements may be administered to any patient needing, e.g., improvement of an aging-related skin condition such as, for example, skin elasticity, skin regeneration, metabolism, etc. For example, patient populations include, but are not limited to: men over age fifty, and women over age fifty. That is, patients whose skin may not be as elastic or firm as a younger patient. However, it would be understood that humans under the age of fifty might also experience changes in their skin, which would benefit from administration of a composition described herein. For example, a patient who may also be administered a composition described herein may be one who had plastic or reconstructive surgery, which population includes any human of any age. In addition to these compositions, a treating physician may add other disease-specific supplements as the patient's condition warrants. In addition to the pre-packaged nutritional supplements, the dispensing physician may add one or more other specific supplements, if needed.

In one embodiment, an aqueous solution adapted for human administration, comprises an therapeutically effective amount of following ingredients: cyanocobalamin or/and methylcobalamin (vitamin B12), ascorbic acid (vitamin C), zinc, ahseutasanchin, vitamin E, vitamin D, selenium, glutathione (GSH), anthocyanidin, omega-3, EPA, DHA, lecithin, CoQ10, chrome, and magnesium. The pH of the solution can be adjusted to a pH that is physiologically acceptable for administration to humans.

Vitamin B12 may be included in a composition to increase metabolism, or improve aging-related skin conditions. In one embodiment, the aqueous solution comprises from about 3000 mcg to about 5000 mcg of cyanocobalamin and/or methylcobalamin. One would appreciate that vitamin B12 exists in multiple forms suitable for therapeutic use, including cyanocobalamin and methylcobalamin, which forms are contemplated for use herein.

Vitamin C (ascorbic acid) is included in a composition in an amount of from about 700 mg to about 1000 mg.

Zinc is included in a composition in an amount of from about 11 mg to about 15 mg.

Ahseutasanchin is included in a composition in an amount of from about 4 mg to about 6 mg.

Vitamin E is included in a composition in an amount of from about 100 IU to about 200 IU.

Vitamin D is included in a composition in an amount of from about 150 IU to about 300 IU.

Selenium is included in a composition in an amount of from about 100 mcg to about 150 mcg.

Glutathione (GSH) is included in a composition in an amount of from about 30 mg to about 50 mg.

Anthocyanidin is included in a composition in an amount of from about 100 mg to about 150 mg.

Omega-3 is included in a composition in an amount about 1 mg to about 500 mg.

EPA is included in a composition in an amount of from 200 mg to about 300 mg.

DHA is included in a composition in an amount of from about 200 mg to about 300 mg.

Lecithin is included in a composition in an amount about 1 mg to about 500 mg.

CoQ10 is included in a composition in an amount of from about 30 mg to about 50 mg.

Chrome is included in a composition in an amount of from about 100 mcg to about 150 mcg.

Magnesium is included in a composition in an amount of from about 150 mg to about 200 mg.

The aqueous solution may optionally include a chemical stabilizer. Any number of chemical stabilizers may be used to stabilize and increase shelf life of formulations. In one aspect, a chemical stabilizer is employed to retard or prevent degradation of a vitamin compound induced by ultraviolet light. Chemical stabilizers include, but are not limited to, a chelating agent, an anti-oxidant, acidifying agent or gentisic acid. In one embodiment, the chemical stabilizer is an acidifying agent or gentisic acid.

An aqueous solution may optionally include a preservative. Any number of preservatives may be used to increase shelf life of intramuscularly injectable formulations. Non-limiting examples of preservatives are, for example, benzyl alcohol, methylparaben, propylparaben, benzyl alcohol, thimerosal, m-Cresol and methyl p-hydroxybenzoate. In one embodiment, benzyl alcohol also acts as a mild anesthetic potential that may mitigate the pain of injection.

An may optionally include a preservative and a chemical stabilizer.

Solution formulations can be prepared by dissolving these components in an aqueous buffer known in the art of solution formulations such as phosphate buffers and/or citrate buffers.

In one aspect, provided herein is an aqueous vitamin composition which is specifically tailored for (but not limited to) delivery using AQT technology. A vitamin composition which is specifically tailored for delivery using AQT technology generally refers to a composition prepared for administration of a substance in an amount appropriate for delivery using AQT technology.

The aforementioned components of the bioactive formulations (compositions) can be combined in any ratio, and administered in any volume, as determined necessary.

Containers

Compositions described herein may be packed into a container such as, for example, an ampoule, vial or pre-filled syringe.

Provided herein is a container comprising a composition described herein prepared for administration of a substance, wherein the composition is an aqueous solution consisting of water-soluble components. The vitamin compositions described herein are typically packed in a sealed and sterilized plastic or glass container. The container can be supplied in a unit dosage form such as an ampoule, vial or disposable pre-filled syringe. Containers described herein may, in some instances, contain a UV-blocking agent which help prevent degradation of components of the compositions.

Provided herein is a container comprising an aqueous solution formulated for needleless injection, the aqueous solution comprising: Cyanocobalamin and/or methylcobalamin; ascorbic acid (vitamin C); ahseutasanchin; Vitamin E; Vitamin D; selenium; zinc; glutathione (GSH); anthocyanidin; Omega-3; EPA; DHA; lecithin; CoQ10; chrome; and magnesium, wherein the container optionally comprises a UV-blocking agent which help prevent degradation of components of the compositions. The container may bean ampoule, vial or pre-filled syringe.

Compositions described herein may be packed into a container such as, for example, an ampoule, vial or pre-filled syringe combined with AQT technology.

Provided herein is a container combined with AQT technology comprising a composition described herein prepared for administration of a substance, wherein the composition is an aqueous solution consisting of water-soluble components. The vitamin compositions described herein are typically packed in a sealed and sterilized plastic or glass container. The container can be supplied in a unit dosage form such as an ampoule, vial or disposable pre-filled syringe. Containers described herein may, in some instances, contain a UV-blocking agent which helps prevent degradation of components of the compositions.

Provided herein is a vial or ampoule combined with Aquagold (AQT) technology comprising a pre-formulated vitamin solution formulated for delivery using Aquagold (AQT) technology. Also provided herein is a vial containing sterile powders for the preparation of sterile injectable solutions; methods of preparation are vacuum drying and freeze-drying, which yield a powder of the active ingredient plus any additional desired ingredient from a previously filtered or otherwise sterilized solution thereof. The vial can contain a composition in sterile powders in unit dosage form which after the addition of sterile water is then stable for at least three months, at least six months or at least one year when stored at room temperature and is suitable for delivery using AQT technology.

Provided herein is a pre-filled syringe combined with AQT technology comprising a composition described herein. Pre-filled syringes may contain 1 cc (1 ml), or up to 1.2 cc. In some embodiments, the syringe is a 1 cc or a 2 cc syringe.

Provided herein is a needleless injection device combined with AQT technology comprising a composition described herein. Needleless injection devices may contain 1 cc (1 ml), or up to 1.2 cc. In some embodiments, the syringe is a 1 cc or a 2 cc syringe.

The dosage amounts in these formulas can be modified depending on the judgment of the treating physician and the requirements of the individual patient. More specifically, the dosage amounts of one, some, or all of the nutritional compounds can be decreased by 5%, 10%, 20%, 30%, 40%, 50% or up to about 75% or increased by 20%, 40%, 50%, 75%, 100%, 200%, 300%, 400% or up to about 500% of the stated preferred amounts.

Volumes to be considered for packaging in vials and ampoules include, but are not limited to, about 0.1 ml, about 0.2 ml, about 0.3 ml, about 0.4 ml, about 0.5 ml, about 0.6 ml, about 0.7 ml, about 0.8 ml, about 0.9 ml, about 1.0 ml, about 1.1 ml, about 1.2 ml, about 1.3 ml, about 1.4 ml, about 1.5 ml, about 1.6 ml, about 1.7 ml, about 1.8 ml, about 1.9 ml, about 2.0 ml, about 2.1 ml, about 2.2 ml, about 2.3 ml, about 2.4 ml, about 2.5 ml, about 2.6 ml, about 2.7 ml, about 2.8 ml, about 2.9 ml, about 3.0 ml, about 3.1 ml, about 3.2 ml, about 3.3 ml, about 3.4 ml, about 3.5 ml, about 3.6 ml, about 3.7 ml, about 3.8 ml, about 3.9 ml, about 4.0 ml, about 4.1 ml, about 4.2 ml, about 4.3 ml, about 4.4 ml, about 4.5 ml, about 4.6 ml, about 4.7 ml, about 4.8 ml, about 4.9 ml, and about 5.0 ml.

Provided herein is a pre-filled syringe, comprising a composition described herein. Pre-filled syringes may contain 1 cc (1 ml), or up to 1.2 cc. In some embodiments, the syringe is a 1 cc or a 2 cc syringe.

Provided herein is a needleless injection device comprising a composition described herein. Needleless injection devices may contain 1 cc (1 ml), or up to 1.2 cc. In some embodiments, the syringe is a 1 cc or a 2 cc syringe.

The dosage amounts in these formulas can be modified depending on the judgment of the treating physician and the requirements of the individual patient. More specifically, the daily dosage amounts of one, some, or all of the nutritional compounds can be decreased by 5%, 10%, 20%, 30%, 40%, 50% or up to about 75% or increased by 20%, 40%, 50%, 75%, 100%, 200%, 300%, 400% or up to about 500% of the stated preferred amounts. In another embodiment, the daily dosage amounts of one, some, or all of the nutritional compounds can be decreased by 5%, 10%, 15%, 20%, 25% or up to about 30%; or increased by 10%, 15%, 20%, 25%, 30%, 40%, 50%, 75%, or up to about 100% of the stated preferred amounts.

Methods of Use

Generally, the methods include administering a therapeutically effective amount of a composition as described herein, to a subject who is in need of, or who has been determined to be in need of, such treatment.

A "subject" or "patient" (e.g., a mammal such as a human or a non-human animal) can be a mammal who exhibits one or more clinical manifestations and/or symptoms of a disease or skin condition, hair loss, wound healing and/or prevention of scarring, or for anti-aging, longevity and wellness purpose described herein. In certain situations, a subject may be asymptomatic and yet still have clinical manifestations of the disease or condition.

A physician or veterinarian can readily determine and prescribe the effective amount of the formulation required. For example, the physician or veterinarian could start doses of the compounds employed in the formulation at levels lower than that required in order to achieve the desired therapeutic effect and gradually increase the dosage until the desired effect is achieved. Alternatively, a dose can remain constant.

Provided herein is a method of promoting vitality and well-being in a human patient, the method comprising administering a composition formulated for needleless injection, wherein the composition is administered to the human patient. Additionally or alternatively, provided herein is a method of promoting vitality, well-being and skin conditions in a human patient, the method comprising administering a vitamin B supplement composition formulated for needleless injection, wherein the vitamin B supplement composition is administered to the human patient. Compositions to be administered are described in more detail above.

Also provided herein is a method of treating or ameliorating disease or symptoms associated with aging process in a human patient in need thereof, comprising administering to the patient an aqueous solution comprising cyanocobalamin or/and methylcobalamin; ascorbic acid (vitamin C); ahseutasanchin; Vitamin E; Vitamin D; selenium; zinc; glutathione (GSH); anthocyanidin; Omega-3; EPA; DHA; lecithin; CoQ10; chrome; and magnesium. In one aspect, the container is an ampoule, vial, a needleless injection device or pre-filled syringe. Containers described herein may, in some instances, contain a UV-blocking agent which helps prevent degradation of components of the compositions. In one embodiment, a container comprises from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium.

In one aspect, the disease or symptom to be treated includes those associated with a vitamin B deficiency, such as, for example, chronic fatigue syndrome, high stress levels, pellagra, acne, microcyrtic anemia, macrocytic anemia, reduced skin elasticity, impaired skin regeneration rate, slowed metabolism rate, reduced smoothness and/or softness of skin, dullness of skin, hyperpigmentation or a combination thereof.

Also provided herein is a method of improving tissue repair and regeneration in a human patient in need thereof, comprising administering to the patient an aqueous solution comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium; wherein the composition is administered to the patient through needleless injection.

Also provided herein is a method of improving aging-related skin conditions, such as skin elasticity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and making wrinkles appear softer and/or less prominent in human patient in need thereof, comprising administering to the patient an aqueous solution comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium.

In order to achieve personalized benefits at maximal level, one may add or remove few of the components listed above, as well as increasing or reducing the dose.

Provided herein is a method of treating or ameliorating a disease or one or more symptoms associated with a vitamin B deficiency in a human patient in need thereof. The method comprises administering to a patient in need thereof, an aqueous solution comprising an effective amount of cyanocobalamin and/or methylcobalamin (vitamin B12), ascorbic acid (vitamin C), zinc, ahseutasanchin, vitamin E, vitamin D, selenium, glutathione (GSH), anthocyanidin, omega-3, EPA, DHA, lecithin, coenzyme Q10 (CoQ10), chrome, and magnesium, and optionally a chemical stabilizer and optionally a preservative, optionally a chemical stabilizer or a preservative, wherein the aqueous solution is formulated for needleless injection. In one embodiment, the method comprises administering to the patient an aqueous solution comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium; wherein the composition is administered to the patient through needleless injection.

Typically, symptoms of vitamin B deficiency include, but are not limited to, chronic fatigue syndrome, high stress levels, low energy, reduced skin elasticity, slow skin regeneration, hyperpigmentation, vitiligo and reduced rate of metabolism.

The methods described herein include methods for the treatment of disorders associated with vitamin B deficiencies. In some embodiments, the disorder is beriberi, ariboflavinosis, pellagra, acne, paresthesia, microcyrtic anemia, or macrocytic anemia.

Provided herein is a method for improving the cosmetic appearance of a subject, comprising administering a bioactive formulation using a system described herein. In one embodiment, the subject being treated suffers from a disease selected from beriberi, Wernicke's encephalophay, ariboflavinosis, pellagra, acne, paresthesia, microcyrtic anemia, or macrocytic anemia. In another embodiment, administration of said bioactive formulation improves skin elasticity, skin regeneration, metabolism, or a combination. The bioactive formulation may be delivered painlessly directly tapped into the skin using repeated motion. The bioactive formulation may exhibit characteristics of enhanced or microdelivery through an automated compounding technology. Collagen may be generated as the bioactive formulation is administered into skin through microneedles with a repeated motion. A predetermined dosage of the bioactive formulation may be administered into the skin in a manner substantially without absorption of said compounds or formulations via the gastrointestinal tract. Presented herein is a method of improving skin health using microneedle delivery of certain bioactive formulations composed of hyaluronic acid, botulinum toxin, collagen, vitamins, minerals, minoxidil, platelet-rich plasma (PRP), and/or poly-L-lactic acid (PLLA). Improving skin health in a subject comprises, for example, reduction of pore size indicating that skin cells are healthy, increase in moisture content/hydration of the skin resulting in radiance of the skin, easy breakdown of dark spots showing high metabolism and vitamin C, elasticity, natural glow, less sagging, wrinkles, smaller pore sizes, high elasticity, smoothness, high content of moisture, etc.

In one aspect, a formulation is administered until one or more symptoms are reduced. In one embodiment, one or more symptoms are reduced in severity or duration by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, one or more symptoms are reduced in severity or duration by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

Provided herein is a method of treating or improving one or more aspects of aging-related health problems in a patient in need thereof comprising administering to the patient a composition described herein. In one embodiment, the composition is administered via the methods disclosed herein. For example, administration of a composition herein may improve cognitive function; combat fatigue; promote energy production; relieve anxiety and depression; promote calcium intake; maintain the central nervous system; boost the immune system; and maintain the blood pressure. In one embodiment, the method comprises administering to the patient an aqueous solution comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 20 mcg to about 40 mcg of nicotinamide (vitamin B3); from about 3 mg to about 6 mg of thiamine hydrochloride; from about 4 mg to about 10 mg of pyridoxine HCl (vitamin B6); from about 2 mg to about 3.6 mg of riboflavin 5-phosphate sodium (vitamin B2); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium; wherein the composition is administered to the patient through needleless injection.

In one aspect, a formulation is administered until one or more symptoms are improved. In one embodiment, skin elasticity, skin regeneration, metabolism, or a combination thereof are improved by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, skin elasticity, skin regeneration, metabolism, or a combination thereof are improved by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

Also provided herein is a method of improving wound healing in a human patient in need thereof, comprising administering to the patient an aqueous solution composition described herein. In one embodiment, the composition is via needleless injection. In one embodiment, the method comprises administering to the patient an aqueous solution comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 20 mcg to about 40 mcg of nicotinamide (vitamin B3); from about 3 mg to about 6 mg of thiamine hydrochloride; from about 4 mg to about 10 mg of pyridoxine HCl (vitamin B6); from about 2 mg to about 3.6 mg of riboflavin 5-phosphate sodium (vitamin B2); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium; wherein the composition is administered to the patient as disclosed herein. In some instances, the wound is a post-surgical wound or the result of trauma or surgery. In one embodiment, surgery is plastic surgery or reconstructive surgery. The treating physician may determine that the solution is to be administered prior to surgery, after surgery, or both. According to the method, the aqueous solution may be administered to a human on a periodic basis, for example, on a daily basis, a weekly basis, twice-a-month, a monthly basis, or as recommended depending on the judgment of the treating physician and the requirements of the individual patient, or as recommended. In one embodiment, a composition described herein is administered 1 day, 2 days, 3 days, 4 days, 5 days or 6 days prior to surgery. In another embodiment, a composition described herein is administered 1 day, 2 days, 3 days, 4 days, 5 days or 6 days after surgery. In yet another embodiment, a composition described herein is administered 1 day, 2 days, 3 days, 4 days, 5 days or 6 days prior to surgery and also 1 day, 2 days, 3 days, 4 days, 5 days or 6 days after surgery.

Provided herein is a method of treating or ameliorating a disease or one or more symptoms of a condition in a patient in need thereof, comprising administering to the patient an aqueous solution comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg of selenium; from about 30 mg to about 50 mg of glutathione (GSH); from about 100 mg to about 150 mg of anthocyanidin; from about 1 mg to about 500 mg of omega-3; from about 200 mg to about 300 mg of EPA; from about 200 mg to about 300 mg of DHA; from about 1 mg to about 500 mg of lecithin; from about 30 mg to about 50 mg of coenzyme Q10 (CoQ10); from about 100 mcg to about 150 mcg of chrome; and from about 150 mg to about 200 mg of magnesium; wherein the composition is administered to the patient through needleless injection. The one or more symptoms are selected from depression, headaches, chronic fatigue syndrome, high stress levels, hyperthyroidism, low energy, hair loss, wound healing, scarring, aging, longevity, wellness purpose, and a combination thereof. The disease is selected from beriberi, Wernicke's encephalopathy, ariboflavinosis, pellagra, acne, paresthesia, microcyrtic anemia, or macrocytic anemia. Administration of the composition improves skin elasticity, skin regeneration, metabolism, or a combination thereof. The aqueous solution further comprises a chemical stabilizer in some instances. The aqueous solution further comprises a preservative in some instances. The aqueous solution further comprises a chemical stabilizer and a preservative in some instances.

A method of improving wound healing in a human patient in need thereof, comprising administering to the patient an aqueous solution comprising: from about 3000 to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg of selenium; from about 30 mg to about 50 mg of glutathione (GSH); from about 100 mg to about 150 mg of anthocyanidin; from about 1 mg to about 500 mg of omega-3; from about 200 mg to about 300 mg of EPA; from about 200 mg to about 300 mg of DHA; from about 1 mg to about 500 mg of lecithin; from about 30 mg to about 50 mg of coenzyme Q10 (CoQ10); from about 100 mcg to about 150 mcg of chrome; and from about 150 mg to about 200 mg of magnesium; wherein the composition is administered to the patient through administration as disclosed herein. In some instances, the wound is a post-surgical wound. The aqueous solution may be administered to the patient prior to surgery. The aqueous solution may be administered to the patient after surgery. The aqueous solution may be administered to the patient prior to and after surgery.

Provided herein is a method of promoting vitality and well-being in a human patient, the method comprising administering a composition formulated for delivery using AQT technology, wherein the composition is administered to the human patient.

Also provided herein is a method of treating or ameliorating disease or symptoms associated with aging process in a human patient in need thereof, comprising administering to the patient an aqueous solution comprising functional vitamins and minerals such as cyanocobalamin or/and methylcobalamin; ascorbic acid (vitamin C); ahseutasanchin; vitamin E; vitamin D; selenium; zinc; glutathione (GSH); anthocyanidin; omega-3; EPA; DHA; lecithin; coenzyme Q10 (CoQ10); chrome; and magnesium. In one aspect, the container is an ampoule, vial or pre-filled syringe combined with AQT technology. Containers described herein may, in some instances, contain a UV-blocking agent which helps prevent degradation of components of the compositions. In one embodiment, a container comprises from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium.

In one aspect, the disease or symptom to be treated includes those associated with a vitamin B deficiency, such as, for example, chronic fatigue syndrome, high stress levels, pellagra, acne, microcyrtic anemia, macrocytic anemia, reduced skin elasticity, impaired skin regeneration rate, slowed metabolism rate, reduced smoothness and/or softness of skin, dullness of skin, hyperpigmentation or a combination thereof.

Also provided herein is a method of improving tissue repair and regeneration in a human patient in need thereof, comprising administering to the patient an aqueous solution comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium; wherein the composition is administered to the patient using Aquagold (AQT) technology.

Also provided herein is a method of improving aging-related skin conditions, such as skin elasticity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and making wrinkles appear softer and/or less prominent in human patient in need thereof, comprising administering to the patient an aqueous solution comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium.

Provided herein is a method of treating or ameliorating a disease or one or more symptoms associated with a vitamin B deficiency in a human patient in need thereof. The method comprises administering to a patient in need thereof, an aqueous solution comprising an effective amount of cyanocobalamin or/and methylcobalamin (vitamin B12), ascorbic acid (vitamin C), zinc, ahseutasanchin, vitamin E, vitamin D, selenium, glutathione (GSH), anthocyanidin, omega-3, EPA, DHA, lecithin, CoQ10, chrome, and magnesium, and optionally a chemical stabilizer and optionally a preservative, optionally a chemical stabilizer or a preservative, wherein the aqueous solution is formulated for needleless injection. In one embodiment, the method comprises administering to the patient an aqueous solution comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium; wherein the composition is administered to the patient through Aquagold (AQT) technology.

Typically, symptoms of vitamin B deficiency include, but are not limited to, chronic fatigue syndrome, high stress levels, low energy, reduced skin elasticity, slow skin regeneration, hyperpigmentation, vitiligo and reduced rate of metabolism.

The methods described herein include methods for the treatment of disorders associated with vitamin B deficiencies. In some embodiments, the disorder is beriberi, ariboflavinosis, pellagra, acne, paresthesia, microcyrtic anemia, or macrocytic anemia.

In one aspect, a formulation is administered until one or more symptoms are reduced. In one embodiment, one or more symptoms are reduced in severity or duration by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, one or more symptoms are reduced in severity or duration by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

Provided herein is a method of treating or improving one or more aspects of aging-related health problems in a patient in need thereof comprising administering to the patient a composition described herein. In one embodiment, the composition is administered using AQT technology. For example, administration of a composition herein may improve cognitive function; combat fatigue; promote energy production; relieve anxiety and depression; promote calcium intake; maintain the central nervous system; boost the immune system; and maintain the blood pressure. In one embodiment, the method comprises administering to the patient an aqueous solution comprising about from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 20 mcg to about 40 mcg of nicotinamide (vitamin B3); from about 3 mg to about 6 mg of thiamine hydrochloride; from about 4 mg to about 10 mg of pyridoxine HCl (vitamin B6); from about 2 mg to about 3.6 mg of riboflavin 5-phosphate sodium (vitamin B2); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium; wherein the composition is administered to the patient through AQT technology.

In one aspect, a formulation is administered until one or more symptoms are improved. In one embodiment, skin elasticity, skin regeneration, metabolism, or a combination thereof are improved by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, skin elasticity, skin regeneration, metabolism, or a combination thereof are improved by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

Also provided herein is a method of improving wound healing in a human patient in need thereof, comprising administering to the patient an aqueous solution composition described herein. In one embodiment, the composition is via AQT technology. In one embodiment, the method comprises administering to the patient an aqueous solution comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 20 mcg to about 40 mcg of nicotinamide (vitamin B3); from about 3 mg to about 6 mg of thiamine HCl; from about 4 mg to about 10 mg of pyridoxine HCl (vitamin B6); from about 2 mg to about 3.6 mg of riboflavin 5-phosphate sodium (vitamin B2); from about 11 mg to about 15 mg of zinc; from about 4 mg to 6 mg of ahseutasanchin; from about 100 IU to 200 IU of vitamin E; from about 150 IU to 300 IU of vitamin D; from about 100 mcg to 150 mcg of selenium; from about 30 mg to 50 mg of glutathione (GSH); from about 100 mg to 150 mg of anthocyanidin; from about 1 mg to about 500 mg of omega-3; from about 200 mg to 300 mg of EPA; from about 200 mg to 300 mg of DHA; from about 1 mg to about 500 mg of lecithin; from about 30 mg to 50 mg of coenzyme Q10 (CoQ10); from about 100 mcg to 150 mcg of chrome; from about 150 mg to 200 mg of magnesium; wherein the composition is administered to the patient through Aquagold (AQT) technology. In some instances, the wound is a post-surgical wound or the result of trauma or surgery. In one embodiment, surgery is plastic surgery or reconstructive surgery. The treating physician may determine that the solution is to be administered prior to surgery, after surgery, or both. According to the method, the aqueous solution may be administered to a human on a periodic basis, for example, on a daily basis, a weekly basis or as recommended depending on the judgment of the treating physician and the requirements of the individual patient or as recommended. In one embodiment, a composition described herein is administered 1 day, 2 days, 3 days, 4 days, 5 days or 6 days prior to surgery. In another embodiment, a composition described herein is administered 1 day, 2 days, 3 days, 4 days, 5 days or 6 days after surgery. In yet another embodiment, a composition described herein is administered 1 day, 2 days, 3 days, 4 days, 5 days or 6 days prior to surgery and also 1 day, 2 days, 3 days, 4 days, 5 days or 6 days after surgery.

In one aspect, a formulation is administered until one or more symptoms are reduced. In one embodiment, one or more symptoms are reduced in severity or duration by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, one or more symptoms are reduced in severity or duration by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

Provided herein is a method of treating or improving one or more aspects of skin damage in a patient in need thereof comprising administering to the patient a composition described herein. Administration of a composition herein may improve skin elasticity, skin regeneration, metabolism, smoothness and/or softness of skin (i.e., making the skin feel smoother and softer following treatment); the overall appearance of skin; evening out skin tone and texture; clarity and/or radiance of skin; making the skin look younger; and making wrinkles appear softer and/or less prominent, or a combination thereof.

In one embodiment, the method comprises administering to the patient an aqueous solution described herein.

In one aspect, a formulation is administered until one or more symptoms are improved. In one embodiment, skin elasticity, skin regeneration, metabolism, or a combination thereof are improved by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, skin elasticity, skin regeneration, metabolism, or a combination thereof are improved by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

Also provided herein is a method of improving wound healing in a human patient in need thereof, comprising administering to the patient an aqueous solution composition described herein.

In some instances, the wound is a post-surgical wound or the result of trauma or surgery. In one embodiment, surgery is plastic surgery or reconstructive surgery. The treating physician may determine that the bioactive formulation is to be administered prior to surgery, after surgery, or both. According to the method, the bioactive formulation may be administered to a human on a periodic basis, for example on a daily basis, a weekly basis or as recommended depending on the judgment of the treating physician and the requirements of the individual patient or as recommended.

In one embodiment, the method comprises administering to the patient a bioactive formulation described herein. In some instances, the wound is a post-surgical wound or the result of trauma or surgery. In one embodiment, surgery is plastic surgery or reconstructive surgery. The treating physician may determine that the bioactive formulation is to be administered prior to surgery, after surgery, or both. According to the method, the bioactive formulation may be administered to a human on a periodic basis, for example on a daily basis, a weekly basis or as recommended depending on the judgment of the treating physician and the requirements of the individual patient or as recommended.

Provided herein is a method of treating or improving one or more aspects of aging-related skin damage in a patient in need thereof comprising administering to the patient a composition described herein. In one embodiment, the composition is administered via intradermal injection. In another embodiment, the composition is administered via topical use. For example, administration of a composition herein may improve skin elasticity, skin regeneration, skin hydration, smoothness and/or softness of skin (i.e., making the skin feel smoother and softer following treatment); the overall appearance of skin; evening out skin tone and texture; clarity and/or radiance of skin; making the skin look younger; and making wrinkles and fine lines appear softer and/or less prominent, or a combination thereof.

In one embodiment for intradermal injection, the method comprises administering to the patient an aqueous solution described herein.

Zinc sulfate heptahydrate may be included in a composition that is formulated to improve provides aesthetic enhancement to a subject. In one embodiment, the aqueous solution comprises from about 0.05 to about 5 mg zinc sulfate heptahydrate, from about 0.75 to about 2 mg zinc sulfate heptahydrate, from about 0.1 to about 1 mg zinc sulfate heptahydrate, or from about 0.1 to about 0.5 mg zinc sulfate heptahydrate. In one embodiment, zinc sulfate heptahydrate is present in a composition in an amount of about 0.1 mg.

Hyaluronic acid may be included in a composition that is formulated to improve provides aesthetic enhancement to a subject. In one embodiment, the aqueous solution comprises from about 0.5 mg/ml to about 25 mg/ml hyaluronic acid, from about 1.0 mg/ml to about 20 mg/ml hyaluronic acid, from about 1.5 mg/ml to about 15 mg/ml hyaluronic acid, or from about 2.4 mg/ml to about 12 mg/ml hyaluronic acid. In one embodiment, hyaluronic acid is present in a composition in an amount of about 12 mg/ml.

In one aspect, a formulation is administered until one or more symptoms are improved. In one embodiment, skin elasticity, skin regeneration, skin hydration, skin luminosity, skin clarity or a combination thereof are improved by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, skin elasticity, skin regeneration, skin hydration, skin luminosity, skin clarity or a combination thereof are improved by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

An "effective amount" is an amount sufficient to result in one or more beneficial or desired results, either partially or completely. For example, a therapeutic amount is one that achieves the desired therapeutic effect. For example, a patient may experience about a 10%, 20%, 30%, 40%, 50%, 60%, 70%, 80%, 90%, or 100% improvement in one or more symptoms. This amount can be the same or different from a prophylactically effective amount, which is an amount necessary to improve aging-related skin conditions.

An effective amount can be administered in one or more administrations, applications or dosages. A therapeutically effective amount of a therapeutic compound (i.e., an effective dosage) depends on the aesthetic and therapeutic compounds selected.

One would understand that the compositions provided herein may be administered in the described methods in a variety of dosing regimens which can be determined by the treating physician based upon the patient to be treated and the severity of the condition to be treated. Treatment of a subject with a therapeutically effective amount of the therapeutic compounds described herein can include a single treatment or a series of treatments. For example, a composition may be administered intradermally or topically to a patient on a periodic basis, for example on a daily basis, a weekly basis or as recommended depending on the judgment of the treating physician and the requirements of the individual patient or as recommended. In another example, a composition may be administered once daily for about 5 days, about 10 days, about 20 days, about 30 days, about 2 months, about 3 months, about 4 months, about 5 months, about 6 months, about 1 year, about 2 years, about 3 years, about 4 years, about 5 years or more. Alternatively, a composition may be administered once, twice, three times, about 4 times, about 5 times, about 10 times, about 20 times, about 30 times, about 40 times, about 50 times or more. Alternatively, a composition may be administered on days 1, 3, 7, 10, 14, 21, 30, 60 and 90 of a 90-day treatment period. A patient's symptoms may be monitored during treatment and the physician may alter the treatment schedule based upon one or more of the effects of the compositions.

In one embodiment, a composition described herein is administered 1 day, 2 days, 3 days, 4 days, 5 days or 6 days prior to surgery. In another embodiment, a composition described herein is administered 1 day, 2 days, 3 days, 4 days, 5 days or 6 days after surgery. In yet another embodiment, a composition described herein is administered 1 day, 2 days, 3 days, 4 days, 5 days or 6 days prior to surgery and also 1 day, 2 days, 3 days, 4 days, 5 days or 6 days after surgery.

An "effective amount" is an amount sufficient to result in one or more beneficial or desired results, either partially or completely. For example, a therapeutic amount is one that achieves the desired therapeutic effect. For example, a patient may experience about a 10%, 20%, 30%, 40%, 50%, 60%, 70%, 80%, 90%, or 100% improvement in one or more symptoms. This amount can be the same or different from a prophylactically effective amount, which is an amount necessary to prevent onset of disease or disease symptoms.

An effective amount can be administered in one or more administrations, applications or dosages. A therapeutically effective amount of a therapeutic compound (i.e., an effective dosage) depends on the therapeutic compounds selected.

One would understand that the compositions provided herein may be administered in the described methods in a variety of dosing regimens which can be determined by the treating physician based upon the patient to be treated and the severity of the condition to be treated. Treatment of a subject with a therapeutically effective amount of the therapeutic compounds described herein can include a single treatment or a series of treatments. For example, a composition may be administered to a patient on a periodic basis, for example on a daily basis, a weekly basis or as recommended depending on the judgment of the treating physician and the requirements of the individual patient or as recommended. In another example, a composition may be administered once daily for about 5 days, about 10 days, about 20 days, about 30 days, about 2 months, about 3 months, about 4 months, about 5 months, about 6 months, about 1 year, about 2 years, about 3 years, about 4 years, about 5 years or more. Alternatively, a composition may be administered once, twice, three times, about 4 times, about 5 times, about 10 times, about 20 times, about 30 times, about 40 times, about 50 times or more. Alternatively, a composition may be administered on days 1, 3, 7, 10, 14, 21, 30, 60 and 90 of a 90-day treatment period. A patient's symptoms may be monitored during treatment and the physician may alter the treatment schedule based upon one or more of the effects of the compositions.

One would understand that the compositions provided herein may be administered in the described methods in a variety of dosing regimens which can be determined by the treating physician based upon the patient to be treated and the severity of the condition to be treated. Treatment of a subject with a therapeutically effective amount of the therapeutic compounds described herein can include a single treatment or a series of treatments. For example, a composition may be administered as disclosed herein to a patient on a daily basis, a weekly basis or as recommended depending on the judgment of the treating physician and the requirements of the individual patient or as recommended. In another example, a composition may be administered once daily for about 5 days, about 10 days, about 20 days, about 30 days, about 2 months, about 3 months, about 4 months, about 5 months, about 6 months, about 1 year, about 2 years, about 3 years, about 4 years, about 5 years or more. Alternatively, a composition may be administered once, twice, three times, about 4 times, about 5 times, about 10 times, about 20 times, about 30 times, about 40 times, about 50 times or more. In one embodiment, the composition is administered percutaneously.

Alternatively, a composition may be administered on days 1, 3, 7, 10, 14, 21, 30, 60 and 90 of a 90-day treatment period. A patient's symptoms may be monitored during treatment and the physician may alter the treatment schedule based upon one or more of the effects of the compositions.

It may be appreciated that certain factors may influence the dosage and timing required to effectively treat a subject, including but not limited to the severity of the disease or disorder, previous treatments, the general health and/or age of the subject, and other diseases present.

Compositions described herein may be used to treat one or more clinical manifestations and/or symptoms aging related skin problems. The present inventors have identified new compositions that may be applied using AQT technology into a patient to improve overall skin quality, skin elasticity, skin luminosity, skin regeneration, skin hydration, smoothness and/or softness of skin (i.e., making the skin feel smoother and softer following treatment); the overall appearance and health of skin; evening out skin tone and texture; clarity and/or radiance of skin; making the skin look younger; and making wrinkles and fine lines appear softer and/or less prominent, etc. The compositions and methods provided herein provide bioactive compositions formulated with AQT technology. For these compositions to be effective, the compositions provided to a patient should contain suitable amounts of the various active agents required by the patient. Suitable amounts can be determined by the skilled physician and depend on the age, gender and general health of the patient, as well as a surgical, or other procedure planned for the patient. In some cases, it may also be determined based upon the degree of the aging stage. Previous skincare procedures may also be considered when determining a suitable amount of aesthetic composition. In addition, patient compliance is a very important factor, since aesthetic composition is not effective if the patient does not receive the composition and is much less effective if the patient does not receive the proper dose on a consistent basis.

The referred method includes but not limited to hyaluronic acid (HA) or a combination of vitamin supplement compositions and hyaluronic acid (HA) or a combination of hyaluronic acid (HA), micro hyaluronic acid and botulinum toxin or a combination of hyaluronic acid (HA), botulinum toxin and vitamin supplement compositions, micro botulinum toxin, Platelet-rich plasma (PRP), Poly-L- lactic Acid (PLLA), minoxidil, bimatoprost, lidocaine, tattoo removal agents, scar therapy, burn wounds treatment, stretch mark remedies with or without vitamins and any combinations thereof that can be formulated for new delivery of intradermal injection, transjection, AQT and/or topical use.

The referred methods may lead to enhanced effect compared to topicals and/or lighten injectable effect and broadly fill the gap between topicals and injectables.

Simple topical application of topical drugs results in limited bioavailability in many cases and thereby suboptimal therapeutic outcomes. Many drugs do not have the necessary physiochemical properties to be effectively delivered through the skin by passive diffusion. The advantages of this method of delivery over others are as follows: it allows the delivered substances to be absorbed by the body without being altered by digestive enzymes, as would occur if an oral delivery method were used; it is relatively painless, as opposed to intramuscular or subcutaneous injections; and it facilitates rapid diffusion of the delivered substance through the dermis, as the micro needles physically penetrate the barrier of the epidermis, which traditional topical delivery methods do not.

Existing treatments of hyaluronic acid (HA) or botulinum toxin products address deeper facial lines by injecting into muscle layer. The present invention describes a composition of micro HA alone or in combinations with botulinum toxin, and/or vitamin formulations using AQT technology for new benefits such as addressing fine lines, rejuvenation, moisture retention, reducing pore size, reducing sweat, enhance radiance, and improving overall skin quality and/or skin health by delivering through conventional methods as well as AQT technology.

Hyaluronic acid, a naturally occurring chemical in the human body involved in cartilage resilience and skin repair, has been applied medically for decades for a number of different uses. Among the most common of these medical applications employ injectable delivery, for example to treat joint pain, or topical delivery, for example to treat dermatitis. Cosmetically, it is often used as an active agent in facial filler injections to smooth wrinkles and in topical creams and gels to rejuvenate the skin and combat the aging process. Hyaluronic acid (HA) is widely distributed in both prokaryotic and eukaryotic cells. In humans, HA is present in all tissues, especially in the skin. The biological functions of HA include hydrating the tissues, lubricating the joints, maintaining the firmness of the skin, and providing a framework for cells migration. HA is also involved in tissue repair, wound healing and immune responses. In terms of cosmetic and aesthetic use, HA plays a role in hydration of the skin and regulation of collagen deposition, which leads to reduced scarring. HA-related products are usually used as "dermal fillers."

Provided herein is a method of treating or improving one or more aspects of aging-related skin damage in a patient in need thereof comprising administering to the patient a composition described herein. In one embodiment, the composition is administered via intradermal injection. In another embodiment, the composition is administered via topical use. For example, administration of a composition herein may improve skin elasticity, skin regeneration, skin hydration, smoothness and/or softness of skin (i.e., making the skin feel smoother and softer following treatment); the overall appearance of skin; evening out skin tone and texture; clarity and/or radiance of skin; making the skin look younger; and making wrinkles and fine lines appear softer and/or less prominent, or a combination thereof. In one embodiment for intradermal injection, the method comprises administering to the patient an aqueous solution comprising from about 4000 mcg to about 5000 mcg of cobalamin (vitamin B12); from about 100 mg to about 200 mg of ascorbic acid (vitamin C); from about 10 mg to about 60 mg of nicotinamide (vitamin B3); from about 2 mg to about 10 mg of thiamine (vitamin B1); from about 0.1 mg to about 0.2 mg of pyridoxine HCl (vitamin B6); from about 2 mg to about 10 mg of riboflavin 5-phosphate sodium (vitamin B2); from about 0.1 mg to about 0.2 mg of zinc sulfate heptahydrate; from about 2.4 mg/ml to 2.4 mg/ml of HA and any concentration of collagen, botulinum toxin, platelet-rich plasma, and/or poly-L-lactic acid as determined necessary to achieve the aesthetic goals set by the doctor and patient. In another embodiment for topical use, the composition is administered via topical use, the method comprises administering to the patient an aqueous solution comprising about 5000 mcg of cobalamin (vitamin B12); about 200 mg of ascorbic acid (vitamin C); about 40 mg of nicotinamide (vitamin B3); about 6 mg of thiamine hydrochloride (vitamin B1); about 3 mg of pyridoxine hydrochloride (vitamin B6); about 3.6 mg of riboflavin 5-phosphate sodium (vitamin B2); and about 0.1 mg of zinc sulfate heptahydrate; about 12 mg/ml HA, and any concentration of collagen, botulinum toxin, platelet-rich plasma, and/or poly-L-lactic acid where the pH has been adjusted to about 7.4.

Provided herein is a method of treating or improving one or more aspects of aging-related skin damage in a patient in need thereof comprising administering to the patient a composition described herein. For example, administration of a composition herein may improve skin elasticity, skin regeneration, skin hydration, smoothness and/or softness of skin (i.e., making the skin feel smoother and softer following treatment); the overall appearance of skin; evening out skin tone and texture; clarity and/or radiance of skin; making the skin look younger; and making wrinkles and fine lines appear softer and/or less prominent, or a combination thereof. In one embodiment for intradermal injection, the method comprises administering to the patient an aqueous solution comprising from about 4000 mcg to about 5000 mcg of cobalamin (vitamin B12); from about 100 mg to about 200 mg of ascorbic acid (vitamin C); from about 10 mg to about 60 mg of nicotinamide (vitamin B3); from about 2 mg to about 10 mg of thiamine (vitamin B1); from about 0.1 mg to about 0.2 mg of pyridoxine HCl (vitamin B6); from about 2 mg to about 10 mg of riboflavin 5-phosphate sodium (vitamin B2); from about 0.1 mg to about 0.2 mg of zinc sulfate heptahydrate; from about 2.4 to 2.1 mg/ml of HA and any concentration of collagen, botulinum toxin, platelet-rich plasma, and/or poly-L-lactic acid as determined necessary to achieve the aesthetic goals set by the doctor and patient. In another embodiment for topical use, the composition is administered via topical use, the method comprises administering to the patient an aqueous solution comprising about 5000 mcg of cobalamin (vitamin B12); about 200 mg of ascorbic acid (vitamin C); about 40 mg of nicotinamide (vitamin B3); about 6 mg of thiamine hydrochloride (vitamin B1); about 3 mg of pyridoxine hydrochloride (vitamin B6); about 3.6 mg of riboflavin 5-phosphate sodium (vitamin B2); and about 0.1 mg of zinc sulfate heptahydrate; about 12 mg/ml of HA, and any concentration of collagen, botulinum toxin, platelet-rich plasma, and/or poly-L-lactic acid where the pH has been adjusted to about 7.4. In one embodiment, the composition is administered via conventional methods. In another embodiment, the composition is administered via AQT technology.

A microneedle array is used to deliver a drug directly to the dermis, the second layer of skin. Preferably, the microneedle arrays or needleless injector devices as disclosed herein deliver the bioactive agent or drug into the dermal and epidermal junction area. The microneedles puncture the epidermal barrier and deliver the drug directly to the dermis to maximize diffusion to the bloodstream and absorption by the body's active tissues. As stated above, this delivery method has an advantage over oral delivery because it allows the drug to be absorbed without coming into contact with powerful digestive enzymes, over injectable delivery because it is comparatively painless, and over topical delivery because it allows for much greater absorption of the delivered drug. The microneedle array will be attached a reservoir that will contain the drugs to be delivered, and this reservoir will itself be attached to contain an apparatus to encourage flow of the drug solution contained in the reservoir through the microneedles and into the skin.

In one aspect, a formulation is administered until one or more symptoms are improved. In one embodiment, skin quality, skin health, skin elasticity, skin regeneration, skin hydration, skin luminosity, skin clarity or a combination thereof are improved by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, skin quality, skin health, skin elasticity, skin regeneration, skin hydration, skin luminosity, skin clarity or a combination thereof are improved by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

One would understand that the compositions provided herein may be administered in the described methods in a variety of dosing regimens which can be determined by the treating physician based upon the patient to be treated and the severity of the condition to be treated. Treatment of a subject with a therapeutically effective amount of the therapeutic compounds described herein can include a single treatment or a series of treatments. For example, a composition may be administered using AQT technology to a patient on a periodic basis, for example on a daily basis, a weekly basis or as recommended depending on the judgment of the treating physician and the requirements of the individual patient or as recommended. In another example, a composition may be administered once daily for about 5 days, about 10 days, about 20 days, about 30 days, about 2 months, about 3 months, about 4 months, about 5 months, about 6 months, about 1 year, about 2 years, about 3 years, about 4 years, about 5 years or more. Alternatively, a composition may be administered once, twice, three times, about 4 times, about 5 times, about 10 times, about 20 times, about 30 times, about 40 times, about 50 times or more.

Alternatively, a composition may be administered on days 1, 3, 7, 10, 14, 21, 30, 60 and 90 of a 90-day treatment period. A patient's symptoms may be monitored during treatment and the physician may alter the treatment schedule based upon one or more of the effects of the compositions.

Presented is the method of improving therapeutic outcomes using microneedle delivery of certain bioactive formulations composed of hyaluronic acid, botulinum toxin, collagen, vitamins, minerals, retinoic acid, biamtoprost, minoxidil, lidocaine, tattoo removing agents, scar therapy, burn wounds, stem cell therapy, hormonal delivery, personalized vaccines, injectable microchips and/or other drugs or solutions and/or any combinations thereof such that the therapeutic outcome will be enhanced by using micro needle delivery instead of traditional topical application treatment methods.

Simple topical application of topical drugs results in limited bioavailability in many cases and therefore suboptimal therapeutic outcomes. Many drugs do not have the necessary physiochemical properties to be effectively delivered through the skin by passive diffusion. Microneedles may be used for percutaneous delivery of bioactive agents, such as medicines or cosmetics, to the body. The advantages of this method of delivery over others are as follows: it allows the delivered substances to be absorbed by the body without being altered by digestive enzymes, as would occur if an oral delivery method were used; it is relatively painless, as opposed to intramuscular or subcutaneous injections; and it facilitates rapid diffusion of the delivered substance through the dermis, as the micro needles physically penetrate the barrier of the epidermis, which traditional topical delivery methods do not. Preferably, the microneedle arrays or needleless injector devices as disclosed herein deliver the bioactive agent or drug into the dermal and epidermal junction area.

While the uses of the microneedle injection as a general delivery method have been previously explored, the use of this method to deliver certain bioactive skin-enhancing substances to the skin itself more efficiently itself have not been. The coupling of this delivery method with any of the substances listed above to improve skin health has significant potential.

Improved skin health, as used above, includes but is not limited to improved appearance, increased regeneration, increased elasticity, increased anti-oxidative level, reduced photo-aging, reduced wrinkles, reduced scarring, reduced bacterial activities including acne, redistribution of fat and/or other content of the skin, reduced number and/or sizes of pores, reduced callusing, reduced sweating and/or body odor through skin, improved scalp health, increased hair density, increased evenness of hair growth, and increased hair strength. Improved skin health can also be assessed using patient reported outcome (PRO) or a visual analog scale (VAS).

A microneedle array or a single microneedle may be used to deliver hyaluronic acid, a vitamin formulation, or any combination thereof, directly to the dermis, the second layer of skin. Preferably, the microneedle arrays or needleless injector devices as disclosed herein deliver the bioactive agent or drug into the dermal and epidermal junction area. The micro needles puncture the epidermal barrier and deliver the desired substances directly to the dermis for faster, more efficient, and more effective absorption by the skin. Preferably, the microneedle arrays or needleless injector devices as disclosed herein deliver the bioactive agent or drug into the dermal and epidermal junction area. As stated above, this delivery method has an advantage over oral delivery because it allows the desired substances to be absorbed without coming into contact with and risking modification by digestive enzymes, over injectable delivery because it is much less painful, and over topical delivery because it delivers the active substances directly to the dermis and thus prevents them from having to pass through the mostly impermeable epidermis. Preferably, the microneedle arrays or needleless injector devices as disclosed herein deliver the bioactive agent or drug into the dermal and epidermal junction area.

The formulations composed of hyaluronic acid, botulinum toxin, collagen, vitamins, minerals biamptoprost and/or minoxidil act on the skin and/or subcutaneous muscles in order to boost cell rejuvenation and creation, alleviate fine lines and wrinkles, reduce the appearance of scars and blemishes, and improve skin clarity, elasticity, firmness, tone, vitality, and overall health.

In one embodiment for intradermal injection and/or AQT, the method comprises administering to the patient an aqueous solution comprising from about 4000 mcg to about 5000 mcg of cobalamin (vitamin B12); from about 100 mg to about 200 mg of ascorbic acid (vitamin C); from about 10 mg to about 60 mg of nicotinamide (vitamin B3); from about 2 mg to about 10 mg of thiamine (vitamin B1); from about 0.1 mg to about 0.2 mg of pyridoxine HCl (vitamin B6); from about 2 mg to about 10 mg of riboflavin 5-phosphate sodium (vitamin B2); from about 0.1 mg to about 0.2 mg of zinc sulfate heptahydrate; from about 2.4 to 2.1 mg/ml of HA and any concentration of collagen, botulinum toxin, platelet-rich plasma, and/or poly-L-lactic acid as determined necessary to achieve the aesthetic goals set by the doctor and patient.

Provided herein is a method for delivering dihydroergotamine alone or with other compounds using AQT technology. Vitamin B12 may be added for additional benefits. Target effect includes but not limited to improving conditions of migraine, mild Alzheimer's disease, and chronic fatigue syndrome.

Provided herein is a method of delivering stem cell therapy alone or in combination use of laser, ultrasound, or radio frequency. The device may comprise of a screw thread design, which will allow the red blood cells (commonly used in stem cell therapy) to pass slowly and steadily into the dermis.

Provided herein is a method of delivering growth factors including platelet-rich plasma (PRP) alone or in combination use of laser, ultrasound, or radio frequency.

Provided herein is a method of delivering live fat cells to desired areas as a natural filler using automated compounding technology.

Provided herein is a method of delivering parathyroid hormone for Osteoporosis treatment and to increase bone mineral density in the aging population.

Provided herein is a method of removing tattoos by using tattoos removal compounds and formulations with automated compounding technology. For example, the method may comprise a) applying a formulation to the tattooed area, the formulation consisting essentially of: sea salt, purified water, aloe barbadensis (aloe vera) extract, lidocaine hydrochloride and hydroxyethylcellulose; and (b) repeating the tapping motion whenever applicable Provided herein is a method to deliver bioactive compounds or formulations to pediatrics painlessly using Aquagold (AQT) technology. One example is the delivery of vaccines comprising enzymes, which otherwise would be degraded in the hostile digestive tract.

Provided herein is a method to deliver bioactive compounds or formulations in the military setting using Aquagold (AQT) technology. Bioactive compounds by themselves or a combination of but not limited to lidocaine and other temporary anaesthetics, etanercepts, muscle relaxants, burn wounds treatment agents etc.

Provided herein is a method of delivering personalized treatment using AQT technology and smart labeled therapeutics to follow the supply chain for the drugs from the moment it is manufactured to the moment the patient consumes it, allowing a better understanding of economic, social and health outcomes.

Provided herein is a method of delivering personalized treatment using AQT technology and a powered device Provided herein is a method of delivering treatment using AQT technology and an automatic, adjustable injection device with dosage and speed control. The said device will penetrate into the dermis according to the requirements of the treatment. The injection depth may vary anywhere between 250 μm to 1.5 mm. The minimum depth will allow direct delivery right under the dermis while the maximum depth will ensure the delivery into the deep dermal region as discussed below with respect to smart touch technology.

In one aspect, a formulation is administered until one or more symptoms are improved. In one embodiment, skin elasticity, skin regeneration, skin hydration, skin luminosity, skin clarity or a combination thereof are improved by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, skin quality, skin health, skin elasticity, skin regeneration, skin hydration, skin luminosity, skin clarity or a combination thereof are improved by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

One would understand that the compositions provided herein may be administered in the described methods in a variety of dosing regimens which can be determined by the treating physician based upon the patient to be treated and the severity of the condition to be treated.

Treatment of a subject with a therapeutically effective amount of the therapeutic compounds described herein can include a single treatment or a series of treatments. For example, a composition may be administered as disclosed herein to a patient on a daily basis, a weekly basis or as recommended depending on the judgment of the treating physician and the requirements of the individual patient or as recommended. In another example, a composition may be administered once daily for about 5 days, about 10 days, about 20 days, about 30 days, about 2 months, about 3 months, about 4 months, about 5 months, about 6 months, about 1 year, about 2 years, about 3 years, about 4 years, about 5 years or more. Alternatively, a composition may be administered once, twice, three times, about 4 times, about 5 times, about 10 times, about 20 times, about 30 times, about 40 times, about 50 times or more. Alternatively, a composition may be administered on days 1, 3, 7, 10, 14, 21, 30, 60 and 90 of a 90-day treatment period. A patient's symptoms may be monitored during treatment and the physician may alter the treatment schedule based upon one or more of the effects of the compositions.

Microneedle Arrays and Systems Associated with Same

Microneedle injections are used today for the delivery of substances, such as medicines or cosmetics, through the skin to the body. There are certain advantages of this delivery method over others: it increases absorption of the substance as compared to an oral delivery method by allowing the substance to be introduced to the body without first exposing it to a hostile digestive environment; it decreases the pain associated with delivery of the substance as compared to intramuscular or subcutaneous injections by minimizing trauma to the skin and underlying tissues; and it allows for more rapid diffusion of the delivered substance through the dermis as compared to traditional topical delivery methods, as the microneedles physically penetrate the epidermis.

Microneedle technology has the potential to revolutionize the administration of medicines, biologics, nutraceuticals, and aesthetic skin treatments. The ability of microneedles to deliver therapeutic agents painlessly while achieving high bioactivity makes this technology an appealing platform of administration for many applications. Microneedle arrays may also be used in order to increase dosage that is delivered and/or to increase the effective delivery area on a target surface. Traditional injection methods lack the ability to deliver micro droplets of treatment solution to the skin. Such technological advancements, embodied by our invention, prevent the uneven and otherwise lumpy upwelling of fluid beneath the skin and preferentially enable the uniform dissipation of the delivered treatment formulation into the skin.

With a microneedle system designed to penetrate the stratum corneum, therapeutic agents in a liquid solution may be conveyed to the dermis and subcutis of the skin. Compared to topically applied bioactive skin treatments, dermal administration has been shown to significantly improve bioavailability. Furthermore, drugs, nutrients, and aesthetic compositions that cannot permeate the skin may be directly delivered into the tissue.

The direct application device comprises a single or an array of microneedles that will serve not only as an anchor to the skin, but also as a collagen stimulator platform (via collagen induction therapy) to accelerate skin healing or combat age-related decreases in collagen neosynthesis. Each microneedle will have one or multiple grooves inset along its outer wall. This structural feature of the dermal delivery device allows liquids stored in a reservoir at the base of each needle to travel along the needle shaft into the tissue. Altogether, this innovation is a functional treatment regimen applicator that enables the optimal restorative efficacy of bioactive formulations delivered beneath the surface of the skin.

With a microneedle system designed to deliver liquid compositions to the dermal and subcuticular layers of the skin, a broad range of therapeutic objectives can be met. This includes but is not limited to the administration of vaccines, vitamins, minerals, biologics, organic or inorganic drugs, and anesthetics. Combinations of the aforementioned therapeutics may also be formulated to achieve medicinal, therapeutic, pain-management, or aesthetic goals.

Provided herein is a system that presents additional advantage conferring elements specific to the controlled delivery of many types of treatment solutions above that of existing microneedle platforms that facilitate the direct application of bioactive formulations transdermally. Due to a microneedle design that facilitates liquid flow along the outside of the needle, our direct applicator system does not suffer from the issue of clogging that hollow microneedle systems do. Furthermore, consistent delivery depth of treatment is achieved over a topical application after microneedling. This in turn, allows for the patient-specific delivery of kinetic enhancing, nutritional, anesthetic or medicinal agents to the skin, in accordance with practitioner-determined concentrations. With a pressure activated release of liquid formulations our system is easily used through a repeated motion delivery to the skin.

Scaling the microneedle delivery system as necessitated by care objectives that require, for example, more microneedles to administer liquid formulations over a larger target area is also possible. This extension of the design could prove important to applications such as the treatment of large areas of tissue trauma in military or post-operative situations.

A device for detecting an analyte and/or releasing a biochemical into a biological fluid can include an array of hollowed needles, in which each needle includes a protruded needle structure including an exterior wall forming a hollow interior and an opening at a terminal end of the protruded needle structure that exposes the hollow interior, and a probe inside the exterior wall to interact with one or more chemical or biological substances that come in contact with the probe via the opening to produce a probe sensing signal, and an array of wires that are coupled to probes of the array of hollowed needles, respectively, each wire being electrically conductive to transmit the probe sensing signal produced by a respective probe. Sensing biological events in vitro and in vivo can provide real-time detection of physiologically relevant compounds, such as monitoring of metabolites, electrolytes, biochemicals, neurotransmitters, medically relevant molecules, cancer biomarkers, and pathogenic microorganisms.

Provided herein is a system for the controlled administration of treatment solutions possibly comprising nutritional, medicinal, aesthetic or pain management agent supplemented treatment solutions directly to the dermis and/or subcutis of the skin with a repeated tapping motion using a microneedle direct delivery system.

The delivery of liquid formulations to the dermis is facilitated by microneedle penetration of the skin, liquid properties, such as viscosity or degree of emulsification, design of the microneedles, including recesses in the shaft to allow flow, and the driving force of the liquid, which may include capillary force, gravity, or positive pressure.

The underlying treatment strategy utilizes our AQT technology for delivering liquid therapeutic regimens directly to the skin; while minimizing the undesirable consequences associated with traditional transdermal modes of administration. AQT technology is discussed in more detail below with respect to compounding systems and as described in PCT Publication WO 2012/109032, entitled "System and Method for Personalized Injection Treatment": An automated system for compounding pharmaceutical agents for injection treatment of a patient is provided. The system comprises: a housing enclosing an interior space; an inventory structure having a plurality of chambers for individually holding one or more pharmaceutical agent-containing single use capsules, wherein each capsule has a volume capacity of from about 0.1 to about 10.0 mL liquid; means for selecting capsules in accordance with predetermined pharmaceutical agents contained in said capsules; means for moving the selected capsules to a processing area; means for sequentially transferring a controlled quantity of the predetermined pharmaceutical agent with direct fluid communication from each selected capsule to a product container such as a product vial or a syringe under positive or negative pressure; and means for automatically discarding spent capsules from which the pharmaceutical agents have been removed after a single use. This innovative technology will enable a novel personalized medicine platform where the personalized medicine opportunity can be implemented, it can be used to safely and efficiently expand physician services, improve treatment and improve outcomes. This device is applicable for patients requiring effective doses of treatment combinations of vitamins, growth hormone, glucosamine, omega-3, botulinumtoxin A, insulin and other agents that are used for in-office injection.

The competitive benefit of microneedle-facilitated delivery of treatment formulations is consistence of drug delivery to vital areas and an exceptional rate of activity. By utilizing an array of microneedles, consistent penetration depth may be achieved over a broad range of treatment areas with repeated motion delivery, for ease of use and expanded applicability to patient care objectives. Furthermore, improvement of therapeutic outcome following a bioactive treatment administered by microneedles, such as response kinetic, has been shown in similar delivery systems that pierce the stratum corneum.

Our invention further embodies a system which enables improved clinical outcomes by reducing the occurrence of dermal trauma, pain, swelling, irritation etc. to the skin, while improving the bioavailability and uniform distribution of a treatment regimen; thereby enhancing the therapeutic activity and rate of action conferred to the skin over and above existing topical and injection systems.

Biological treatments not limited to recombinant proteins, hormones, extracts, attenuated microorganisms, stem cells and nucleic acid based therapies may also be applied to the skin through AQT technology. With delivery to the dermis or subcutis, the second and third layers of the skin respectively, therapeutic biologics that are sensitive to degradation in the ex vivo environment may benefit patients with a greater degree of curative potency. Moreover, oral methods of delivery can reduce the therapeutic potential of biologics due to the presence of proteolytic enzymes. Certain therapeutics can produce renal or hepatic toxicity during their clearance from the body if they are administered orally or intravenously. With our invention, liver and kidney toxicity may be avoided and treatment is localized.

A microneedle array may contain from 1 to about 500 microneedles, which will be anywhere from about 0.1 to about 2.5 mm in length and from about 0.01 to about 0.5 mm in diameter, and be composed of any metal, metal alloy, metalloid, polymer, or combination thereof, such as gold, steel, silicon, PVP (polyvinylpyrrlidone) (Sullivan S P, Murthy N, Prausnitz M R: Minimally invasive protein delivery with rapidly dissolving polymer microneedles. Adv Mat. 2008 March; 20(5):933-938. PubMed PMCID: PMC3519393), etc. The microneedles may each have one or more recesses running a certain depth into the outer wall to allow for flow of the substance to be delivered down the microneedle and into the dermis; these recesses can be in a plurality of shapes, including but not limited to: straight line, cross shape (+), flat shape (−), or screw thread shape going clockwise or counterclockwise (see, US Publication Number: US 2012-0296280 A1).

A microneedle array will consist of from about 1 to about 500 microneedles, which will be anywhere from about 0.1 to about 2.5 mm in length and from 0.01 to about 0.5 mm in diameter, and be composed of any metal, metal alloy, metalloid, polymer, or combination thereof, such as gold, steel, silicon, PVP (polyvinylpyrrlidone), etc. The microneedles will each have one or more recesses running a certain depth into the outer wall to allow for flow of the substance to be delivered down the microneedle and into the dermis; these recesses can be in a plurality of shapes, including but not limited to: straight line, cross shape (+), flat shape (−), or screw thread shape going clockwise or counterclockwise. The array will be in any shape or combination of shapes, continuous, or discontinuous. The list of possible shapes includes, but is not limited to, circles, triangles, rectangles, squares, rhomboids, trapezoids, and any other regular or irregular polygons. The array will be attached to a reservoir to hold the substances to be delivered, and this reservoir will be any volume (0.25 mL to 5 mL), shape, color, or material (glass, metal, alloy, or polymer), as determined necessary. This reservoir will itself be attached to or contain a means to encourage flow of the drug solutions contained in the reservoir into the skin. Two non-limiting examples of such means are 1) a plate and spring that allows the contained solutions to flow only when the device is tapped into the skin, and 2) a syringe that contains the drug solutions to be delivered and includes a plunger that can be depressed to mechanically drive the solution into the skin.

While the uses of the microneedle injection as a general delivery method have been previously explored, the use of this method to deliver certain bioactive skin-enhancing substances to the skin itself more efficiently itself have not been. The coupling of this delivery method with any of the substances listed above to improve skin health has significant potential.

The delivery of treatments using devices are described, with the possibility of including supplementary and or adjuvant component of bioactive formulations for direct dermal and/or subcutaneous targeting with a microneedle applicator system.

A microneedle direct applicator device will contain, in some instances, an array of from about 1 to about 500 microneedles that are about from 0.1 mm to about 2.5 mm in length and about from 0.001 mm to about 0.5 mm in diameter and be composed of materials that can be made as microneedles including but not limited to, any metal, metal alloy, metalloid, ceramic, polymer, gold, steel, titanium, silicon, PVP (polyvinylpyrrolidone), etc. or any combination thereof.

The microneedles will each have one or more recesses running a certain depth into the outer wall to allow for flow of the substance to be delivered down the microneedle and into the dermis. These recesses can take a plurality of shapes, including but not limited to: straight line, cross shape (+), flat shape (−), or screw thread shape going clockwise or counterclockwise. The array will be in any shape or combination of shapes, continuous, or discontinuous. The list of possible shapes includes, but is not limited to, circles, triangles, rectangles, squares, rhomboids, trapezoids, and any other regular or irregular polygons. The array will be attached to a reservoir, which contains the substances to be delivered, and this reservoir will be any volume (0.25 mL to 5 mL), shape, color, or material (glass, metal, alloy, or polymer), as determined necessary. This reservoir will itself be attached to or contain a means to encourage flow of the substances contained in the reservoir into the skin. Two non-limiting examples of such means are 1) a plate and spring that allows the contained substance to flow only when the device is tapped against the skin, and 2) a syringe that contains the substances to be delivered and includes a plunger that can be depressed to eject the liquid formulations into the skin.

The delivered substances may be of varying viscosities and concentration, from 0.01% to 100%, and will be administered via the microneedle array either independently or in conjunction with the aforementioned nutritional vitamin or mineral, medicinal, or anesthetic supplemented formulations. Functional formulations may include one or more of the following: vitamins, minerals, hormones, antioxidants, hyaluronic acid, micro hyaluronic acid, botulinum toxin, micro-botulinum toxin, collagen, bimatoprost, minoxidil, platelet-rich plasma (PRP), poly-L-lactic acid (PLLA), lidocaine, benzocaine, muscle relaxants, growth factors, insulin, recombinant proteins, polysaccharides, bimatoprost, betulinic acid, chemical preservatives, chemical stabilizers, hydroxyaryl alkyl ketones and their isosteric derivatives, extracts, parathyroid hormone, attenuated microorganisms, stem cells and nucleic acid based therapies or any compatible combinations thereof that may be administered through AQT technology to meet desired therapeutic objectives. The aforementioned components of the bioactive formulations can be combined in any ratio, and administered in any volume, as determined necessary.

The costimulatory effect of the microneedle induced collagen stimulation, in tandem with the direct application of a bioactive adjuvant treatment solution to the dermis or subcutis, may altogether encompass local or systemic benefits that embody the curative potency of the direct dermal delivery of possibly combinatorial bioactive formulations. Furthermore, oral methods of delivery can reduce the therapeutic potential of biologics due to the presence of proteolytic enzymes; our system of therapeutic agent administration enables the activation of high efficacious treatment formulations upon delivery to the dermis.

The formulations described serve to illustrate the possibilities for combinatorial treatment solutions engendered by AQT technology (described in more detail below) capable of delivering liquids directly to the epidermal, dermal and subcuticular layers of the skin. Therefore, it should be understood that further embodiments developed for use with non-hollow or hollow microneedle systems of delivery by those skilled in the art fall within the spirit and scope of this disclosure.

In another aspect, a microneedle device for use in the systems and methods described herein is a device such as described in U.S. Pat. No. 8,257,324, which is hereby incorporated by reference. Briefly, the devices include a substrate to which a plurality of hollow microneedles are attached or integrated, and at least one reservoir, containing a bioactive formulation, selectably in communication with the microneedles, wherein the volume or amount of bioactive formulation to be delivered can be selectively altered. The reservoir can be, for example, formed of a deformable, preferably elastic, material. The device typically includes a means, such as a plunger, for compressing the reservoir to drive the bioactive formulation from the reservoir through the microneedles, A reservoir, can be, for example, a syringe or pump connected to the substrate. A device, in some instances, comprises: a plurality of hollow microneedles (each having a base end and a tip), with at least one hollow pathway disposed at or between the base end and the tip, wherein the microneedles comprise a metal; a substrate to which the base ends of the microneedles are attached or integrated; at least one reservoir in which the material is disposed and which is in connection with the base end of at least one of the microneedles, either integrally or separably; a sealing mechanism interposed between the at least one reservoir and the substrate, wherein the sealing mechanism comprises a fracturable barrier; and a device that expels the material in the reservoir into the base end of at least one of the microneedles and into the skin. The reservoir comprises a syringe secured to the substrate, and the device that expels the material comprises a plunger connected to a top surface of the reservoir. The substrate may be adapted to removably connect to a standard or Luer-lock syringe. In one instance, the device may further include a spring engaged with the plunger. In another instance, the device may further include an attachment mechanism that secures the syringe to the device. In another instance, the device may further include a sealing mechanism that is secured to the tips of the microneedles. In another instance, the device may further include means for providing feedback to indicate that delivery of the material from the reservoir has been initiated or completed. An osmotic pump may be included to expel the material from the reservoir. A plurality of microneedles may be disposed at an angle other than perpendicular to the substrate. In certain instances, the at least one reservoir comprises multiple reservoirs that can be connected to or are in communication with each other. The multiple reservoirs may comprise a first reservoir and a second reservoir, wherein the first reservoir contains a solid formulation and the second reservoir contains a liquid carrier for the solid formulation. A fracturable barrier for use in the devices can be, for example, a thin foil, a polymer, a laminate film, or a biodegradable polymer. The device may further comprise, in some instances, means for providing feedback to indicate that the microneedles have penetrated the skin.

Embodiments described herein relate to application of formulations to the skin.

Microneedles may be used for the delivery of substances, such as therapeutics, nutraceuticals or aesthetic treatments, through the skin to the body. There are certain advantages of this delivery method over others: it increases absorption of the substance as compared to an oral delivery method by allowing the substance to be introduced to the body without first exposing it to a hostile digestive environment; it decreases the pain associated with delivery of the substance as compared to intramuscular or subcutaneous injections by minimizing trauma to the skin, and underlying tissues; and it allows for more rapid diffusion of the delivered substance through the dermis as compared to traditional topical delivery methods, as the microneedles physically penetrate the epidermis.

The present methods efficiently deliver certain bioactive skin-enhancing substances through the stratum corneum has not been. The coupling of this delivery method with any of the substances listed above to improve skin health has significant potential.

Simple topical application of topical drugs results in limited bioavailability in many cases and therefore suboptimal therapeutic outcomes. Many drugs do not have the necessary physiochemical properties to be effectively delivered through the skin by passive diffusion. Microneedle injections are used today for percutaneous delivery of bioactive agents, such as medicines or cosmetics, to the body. The advantages of this method of delivery over others are as follows: it allows the delivered substances to be absorbed by the body without being altered by digestive enzymes, as would occur if an oral delivery method were used; it is relatively painless, as opposed to intramuscular or subcutaneous injections; and it facilitates rapid diffusion of the delivered substance through the dermis, as the microneedles physically penetrate the barrier of the epidermis, which traditional topical delivery methods do not.

A microneedle array is used to deliver hyaluronic acid, a vitamin formulation, or any combination thereof, directly to the dermis, the second layer of skin. The microneedles puncture the epidermal barrier and deliver the desired substances directly to the dermis for faster, more efficient, and more effective absorption by the skin. As stated above, this delivery method has an advantage over oral delivery because it allows the desired substances to be absorbed without coming into contact with and risking modification by digestive enzymes, over injectable delivery because it is much less painful, and over topical delivery because it delivers the active substances directly to the dermis and thus prevents them from having to pass through the mostly impermeable epidermis.

A microneedle array may be used to deliver a bioactive formulation comprising hyaluronic acid, botulinum toxin, collagen, vitamins, minerals, minoxidil, platelet-rich plasma (PRP), and/or poly-L-lactic acid (PLLA) or any combination thereof, directly to the dermis, the second layer of skin. The microneedles puncture the epidermal barrier and deliver the desired substances directly to the dermis for faster, more efficient and more effective absorption by the skin. As stated above, this delivery method has an advantage over oral delivery because it allows the desired substances to be absorbed without coming into contact with and risking modification by digestive enzymes, over injectable delivery because it is much less painful, and over topical delivery because it delivers the active substances directly to the dermis and thus prevents them from having to pass through the mostly impermeable epidermis. The formulations composed of hyaluronic acid, botulinum toxin, collagen, vitamins, minerals, minoxidil, platelet-rich plasma (PRP), and/or poly-L-lactic acid (PLLA) act on the skin and/or subcutaneous muscles in order to boost cell rejuvenation and creation, improve overall skin quality, alleviate fine lines and wrinkles, reduce the appearance of scars and blemishes, reduce pore size, and improve skin clarity, elasticity, firmness, tone, vitality, and overall health.

A microneedle array may be used to deliver a bioactive formulation comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg of selenium; from about 30 mg to about 50 mg of glutathione (GSH); from about 100 mg to about 150 mg of anthocyanidin; from about 1 mg to about 500 mg of omega-3; from about 200 mg to about 300 mg of EPA; from about 200 mg to about 300 mg of DHA; from about 1 mg to about 500 mg of lecithin; from about 30 mg to about 50 mg of coenzyme Q10 (CoQ10); from about 100 mcg to about 150 mcg of chrome; and from about 150 mg to about 200 mg of magnesium, directly to the dermis, the second layer of skin. The microneedles puncture the epidermal barrier and deliver the desired substances directly to the dermis for faster, more efficient and more effective absorption by the skin. As stated above, this delivery method has an advantage over oral delivery because it allows the desired substances to be absorbed without coming into contact with and risking modification by digestive enzymes, over injectable delivery because it is much less painful, and over topical delivery because it delivers the active substances directly to the dermis and thus prevents them from having to pass through the mostly impermeable epidermis. The bioactive formulations composed of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg of selenium; from about 30 mg to about 50 mg of glutathione (GSH); from about 100 mg to about 150 mg of anthocyanidin; from about 1 mg to about 500 mg of omega-3; from about 200 mg to about 300 mg of EPA; from about 200 mg to about 300 mg of DHA; from about 1 mg to about 500 mg of lecithin; from about 30 mg to about 50 mg of CoQ10; from about 100 mcg to about 150 mcg of chrome; and from about 150 mg to about 200 mg of magnesium, act on the skin and/or subcutaneous muscles in order to boost cell rejuvenation and creation, alleviate fine lines and wrinkles, reduce the appearance of scars and blemishes, and improve skin clarity, elasticity, firmness, tone, vitality, and overall health.

A microneedle array may be used to deliver a bioactive formulation directly to the dermis, the second layer of skin. The microneedles puncture the epidermal barrier and deliver the desired substances directly to the dermis for faster, more efficient and more effective absorption by the skin. As stated above, this delivery method has an advantage over oral delivery because it allows the desired substances to be absorbed without coming into contact with and risking modification by digestive enzymes, over injectable delivery because it is much less painful, and over topical delivery because it delivers the active substances directly to the dermis and thus prevents them from having to pass through the mostly impermeable epidermis. The bioactive formulations act on the skin and/or subcutaneous muscles in order to boost cell rejuvenation and creation, alleviate fine lines and wrinkles, reduce the appearance of scars and blemishes, and improve skin clarity, elasticity, firmness, tone, vitality, and overall health.

The device can include, in some instances, a single or plurality of solid, screw-type microneedles, of single or varied length. Typically the needles attach to a substrate or a embedded within the substrate. The substrate can be made of any metal, metal alloy, ceramics, organics metalloid, polymer, or combination thereof, including composites, such as gold, steel, silicon, PVP (polyvinylpyrrlidone) etc. The screw-shape dimensions may be variable. For example, in one embodiment the screw-shape may be a tight coiled screw shape, whereas in another embodiment the screw-shape might be a loose coiled screw shape whereby the screw threads in one embodiment lie closely together along the outer edge of the needle and, in another embodiment, the screw threads lie far from each other along the outer edge of the needle.

In one embodiment a reservoir would attach to the substrate to allow drug solution to flow down the side of the microneedles. In one embodiment the reservoir is a solid canister of differing sizes depending on the desired volume or amount of drug to be delivered. The reservoir contains the drug to be delivered. In another embodiment, the reservoir can be supported by a mechanical (spring loaded or electrified machine-driven) pump system to deliver the drug solution. In another embodiment, the reservoir is composed of a rubber, elastic, or otherwise deformable and flexible material to allow manual squeezing to deliver the drug solution. In another embodiment the device includes hollow needles or needles with alternative ridges and shapes to more efficiently drive solution from the reservoir through to the dermis.

The micro needle array will consist of from about 1 to about 500 micro needles, which will be anywhere from about 0.1 to about 2.5 mm in length and from about 0.01 to about 0.5 mm in diameter, and be composed of any metal, metal alloy, ceramics, organics metalloid, polymer, or combination thereof, including composites, such as gold, steel, silicon, PVP (polyvinylpyrrlidone) etc. The array will be in any shape or combination of shapes, continuous, or discontinuous. The list of possible shapes includes, but is not limited to, circles, triangles, rectangles, squares, rhomboids, trapezoids, and any other regular or irregular polygons. A single array may include needles of variable length to treat different levels of the skin including scalp. In one embodiment the array may be flat. In another embodiment, the array may be curved. The array will be attached to a reservoir to hold the substances to be delivered, and this reservoir will be any volume (0.25 mL to 5 mL), shape, color, or material (glass, metal, alloy, or polymer), as determined necessary. The microneedle shaft may be straight or tapered.

A device described herein may contain, in certain instances, about twenty (2) screw thread design surgical grade microneedles. Each microneedle has a diameter that is thinner than a human hair and may be used for direct dermal application. In one instance, a microneedle has a diameter of less than about 0.18 mm. In another instance, a microneedle has a diameter of about 0.15 mm, about 0.14 mm, about 0.13 mm, about 0.12 mm, about 0.11 mm, or about 0.10 mm. Each microneedle may be plated with 24 carat gold. The device allows for targeted and uniform delivery of a composition comprising a bioactive substance into the skin in a process that is painless compared to injectables. Microneedle injection of a composition comprising a bioactive substance with a device described herein delivers treatments in the skin with improvement compared to other forms of administration; for example, minimal hepatic/renal toxicity compared to oral injection, faster absorption compared to topical administration, flavor/gastrointestinal side effects are better than an inhaler/nasal spray, aesthetic and functional benefits compared to patches, less pain compared to injectables, or a combination thereof. Administration results in easy and precise delivery of a composition comprising a bioactive substance with no bruising, pain, swelling and bleeding. Delivery of a composition comprising a bioactive substance may include sensitive areas and areas difficult to treat with traditional methods, such as around the eyes and mouth. Treatment with the device may also induce the production of several growth factors that recruit collagen-producing fibroblasts.

In one embodiment, a device described herein has the following characteristics:

| Model | Device 1 | Device 2 |
|---|---|---|
| Height | 47.73 mm | 47.73 mm |
| Width | 20 mm | 20 mm |
| Length of microneedle | 600 μm | 250 μm |
| Number of microneedles | 20 | 20 |
| Width of microneedles | 130 μm | 130 μm |
| Size of sheath | 100 μm | 100 μm |
| Microneedle material | 24-carat gold plated stainless steel | 24-carat gold plated stainless steel |
| Reusability | Single use | Multiple use |

The device may include means, manual or mechanical, for compressing the reservoir, creating a vacuum, or otherwise using gravity or pressure to drive the drug from the reservoir through the microneedles or down along the sides of the microneedle. The means can include a plunger, pump or suction mechanism. In another embodiment, the reservoir further includes a means for controlling rate and precise quantity of drug delivered by utilizing a semi-permeable membrane, to regulate the rate or extent of drug which flows along the shaft of the microneedles. The microneedle device enhances transportation of drugs across or into the tissue at a useful rate. For example, the microneedle device must be capable of delivering drug at a rate sufficient to be therapeutically useful. The rate of delivery of the drug composition can be controlled by altering one or more of several design variables. For example, the amount of material flowing through the needles can be controlled by manipulating the effective hydrodynamic conductivity (the volumetric through-capacity) of a single device array, for example, by using more or fewer microneedles, by increasing or decreasing the number or diameter of the bores in the microneedles, or by filling at least some of the microneedle bores with a diffusion-limiting material. It is preferred, however, to simplify the manufacturing process by limiting the needle design to two or three "sizes" of microneedle arrays to accommodate, for example small, medium, and large volumetric flows, for which the delivery rate is controlled by other means.

Other means for controlling the rate of delivery include varying the driving force applied to the drug composition in the reservoir. For example, in passive diffusion systems, the concentration of drug in the reservoir can be increased to increase the rate of mass transfer. In active systems, for example, the pressure applied to the reservoir can be varied, such as by varying the spring constant or number of springs or elastic bands. In either active or passive systems, the barrier material can be selected to provide a particular rate of diffusion for the drug molecules being delivered through the barrier at the needle inlet.

The purpose of the device, in some instances, is to improve the health and vitality of the skin, as detailed herein. This can be achieved both by the delivery of bioactive formulations directly to the dermis and by the mechanical stimulation of the nerve endings in the skin from the tapping of the micro needle device onto the surface of skin.

The array may be in any shape or combination of shapes, continuous, or discontinuous. The list of possible shapes includes, but is not limited to, circles, triangles, rectangles, squares, rhomboids, trapezoids, and any other regular or irregular polygons.

The array may be attached to a reservoir to hold the substances to be delivered, and this reservoir may be any volume (about 0.25 mL to about 5 mL), shape, color, or material (glass, metal, alloy, or polymer), as determined necessary.

This reservoir will itself be attached to or contain a means to encourage flow of the drug solutions contained in the reservoir into the skin. Two non-limiting examples of such means are 1) a plate and spring that allows the contained solutions to flow only when the device is tapped into the skin, and 2) a syringe that contains the drug solutions to be delivered and includes a plunger that can be depressed to mechanically drive the solution into the skin.

Delivered substances may be in any concentration, e.g., from about 0.01% to about 100%, and will be administered via a microneedle array either independently, or in conjunction with the aforementioned bioactive formulations. The formulations that may be administered using such microneedle arrays include any of the solutions (formulations) described herein. The aforementioned components of the solutions may be combined in any ratio, and administered in any volume, as determined necessary.

A device can include a single or plurality of solid, screw-type microneedles, of single or varied lengths housed in a plastic or polymer composite head which embodies a corrugated rubber connector. Typically the needles attach to a substrate or are embedded within the substrate. The substrate can be made of any metal, metal alloy, ceramics, organics metalloid, polymer, or combination thereof, including composites, such as gold, steel, silicon, PVP (polyvinylpyrrlidone) etc. The screw-shape dimensions may be variable. For example, in one embodiment the screw-shape may be a tight coiled screw shape, whereas in another embodiment the screw-shape might be a loose coiled screw shape. The corrugated rubber connector is a unique advantage conferring feature which bestows the microneedle head with a universally adoptable feature for interfacing the micro needle cartridges with multiple glass and or plastic vials, reservoirs and containers as well as electronic appendages for an altogether enhanced adjunct liquid handling, security and surveillance utility.

In one embodiment a reservoir would attach to the substrate to allow drug solution to flow down the side of the microneedles. In one embodiment the reservoir is a solid canister of differing sizes depending on the desired volume or amount of drug to be delivered. The reservoir contains the drug to be delivered. In another embodiment, the reservoir can be supported by a mechanical (spring loaded or electrified machine-driven) pump system to deliver the drug solution. In another embodiment, the reservoir is composed of a rubber, elastic, or otherwise deformable and flexible material to allow manual squeezing to deliver the drug solution. In another embodiment the device includes hollow needles or needles with alternative ridges and shapes to more efficiently drive solution from the reservoir through to the dermis. These methods may be powered with electricity or other available power source. These methods may incorporate lasers, radio frequency, micro needle devices, and/or ultra sounds. The powered device may be computer operated measuring dosage and/or depth and/or speed and/or area. The powered device may be enhanced with artificial intelligence for longitudinal improvements and applications of big data. The powered device may include a compounding chamber and/or reconstituting chamber. The powered device may have a 3-D printing chamber for nano technology such as injectable microchips and/or smart label functionality.

In one aspect, a device may incorporate data producing entities and the data consuming entities agree on the aspects of the data on which they want to maximize post-aggregation utility, and which aspects can be preferentially convolved to achieve mathematically bounded and provable de-identification requirements. In one aspect the data producing entities easily transmit the raw source data through a novel mechanism to a trusted third party computational entity. In another aspect the third part computational entity may be untrusted under a range of adversarial models such as honest-but-curious, global passive adversary, and global active adversary. In these latter cases secure multi-party computation techniques provably protect against the adversary. In either case we will call this third party the data aggregation entity. After receiving the raw source data, the data aggregation entity performs our novel transformations on the data, and provides to the data consuming entities unique statistical information maximizing chosen utility while meeting the previously agreed upon constraints.

The AQT system may be a product of a desktop form-factor suitable for use on an ordinary clinical work surface, it may be a device of size and weight to be easily hand carried to its point-of-use, or it may be a device of size and weight as to be operated while held in the operator's hand. The invention has a mechanism in which medical devices may be loaded into an inventory chamber. The medical devices may be for external use, may be implantable, may be injectable, may be wearable, and may be suitable for passage through the digestive tract. These devices may be introduced into the invention pre-enclosed in a container which contains a microprocessor protecting the provenance and other aspects of the enclosed medical device. This microprocessor interacts with the invention before dispensing the medical device to ensure multiple safety aspects, such as that the dispensed device has not been recalled, is unexpired, is genuine, has not been subjected to improper environmental conditions or forces, and so forth. Inside our invention the device is prepared in an aseptic environment for immediate use. This preparation may contain either or both of mechanical preparation and software preparation. The mechanical preparation may include attachment of wires or accessories, and the 2nd or 3rd printing of customized parts. Such printing is not restricted to printing of ink, but includes other printing technologies such as printing of circuitry, films of metal, plastics, biological materials, and similar substances. The aforementioned mechanical preparation may include procedures customized for an individual patient. The software preparation may include programming of the device, including programming customized for the individual patient. The invention is capable of stand-alone operation, however in a preferred embodiment the invention can operate together with a network to facilitate telemedicine, and machine assisted diagnosis and/or treatment. The preparation of medical devices may include custom compounding of substances including pharmaceuticals, adhesives, lubricants, pharmaceutical or hormone impregnated plastics, and so forth. These substances may be directly applied to the medical device inside the invention, or they may be combined after dispensing, or they may be used separately.

Provided herein are a machine for manufacture and customization of medical devices including implantable medical devices. In a preferred embodiment, the invention interoperates with a network for computer assisted design and customization of devices based on personal information pertinent to an individual patient. The invention is designed to create and dispense customized medical devices in or near the clinical environment in which the medical devices are to be used.

A cadre of micro needles housed in a plastic or polymer composite head is used to deliver treatment solutions, vitamins and any combination thereof, directly to the dermis, the second layer of skin. The application of a mechanical load to the pin of the spring lock system enables the micro needles to puncture the epidermal barrier and deliver the desired substances directly to the dermis for faster, more efficient, and more effective absorption by the skin. The Spring Plate mechanism, housed in the plastic or polymer composite cartridge, is effectively the interface whereby the manual direct application mechanism calibrates the controlled delivery of the treatment solution into the skin.

As stated above, the enhanced delivery of treatment solutions to the skin is dependent on the existence of a trans-epidermal osmotic gradient and hydration force which enables the efficient delivery of treatment solutions to the transdermal space. Advanced advantage conferring efficiencies may also be embodied by a micro needle head which contains a corrugated butyl rubber connector. The corrugated rubber connector is a unique advantage conferring feature which bestows the microneedle head with a universally adoptable feature for interfacing with multiple glass and or plastic vials, reservoirs and containers as well as electronic appendages for an altogether enhanced adjunct liquid handling, security and surveillance utility. The corrugated rubber connector allows for the accommodation of adjunct features such as a threaded single use, self-destruct locking features with or without RFID labels, as well as a snap lock mechanism or a naïve clasp and screw feature for multiple refills, usage and or removals of the head.

An apparatus is provided to enable the direct gene transfer of genetic material into a target cell site ("microseeding"), as a means of obtaining long term expression of native or non-native polypeptides in a host. The apparatus includes a matrix of microneedles that oscillate at a predetermined frequency and receive the genetic material from a delivery system that is integrated with the apparatus. Direct delivery of genetic material is accomplished using a microseeding assembly for delivering genetic material from a dispenser to a target site. The assembly includes a housing and a matrix of microneedles disposed on a translatable shaft at one end of the housing. An integrated dispenser support assembly is connected to the housing for supporting a genetic material dispenser. The support assembly includes an actuator for initiating the delivery of genetic material from the dispenser to the microneedles. A drive assembly is connected to the housing and communicates with the actuator and the microneedles to initiate delivery of genetic material to the microneedles and to oscillate the microneedles at a predetermined frequency.

A further embodiment of the microneedle head, are the corrugated ridges, which facilitate the secure adjunct positioning of the head to the reservoir. The head containing the micro needle mounted array plate may bear a threaded single use, self destruct locking feature with or without a snap lock mechanism or a naïve threaded screw feature for multiple refills, usage and or removals of the head. The universal applicability of the corrugated connector enhances the utility of the drug delivery platform.

A further embodiment of the Spring Plate Delivery System is the manual pin-adjusted mechanism for the release and or inhibition of fluid flow from the reservoir to the transdermal space in the skin via naïve or screw thread microneedles. During intervals of mechanical load the translational force contributes to the elevation of the micro needle mounted plate, which enables the otherwise unhindered flow of treatment solutions through the micro needles and into the transdermal space. In the absence of a mechanical load the converse is true and the treatment solution is contained securely in the reservoir. The presence of a corrugated rubber connector may vary in length and as such confers additional utility features which encompass the flexibility of the spring plate delivery system, thereby enabling the delivery of treatment solutions to hard to reach areas of the body.

Advanced advantage conferring efficiencies may be embodied by a micro needle cartridge which contains the micro needle mounted array plate together with adjunct liquid handling and device security and surveillance bearing features such as a corrugated rubber single use, self-destruct locking feature with or without RFID or corrugated rubber fittings with or without RFID. RFID labelled heads or plastic and or polymer composite heads bearing appendages with RFID labels, ensure improved surveillance measures, thereby assuring the safety of the patient once the operating system and other updates are approved by the relevant marketing authorities and or the FDA; a further advantage of the RFID label is that the medicine can only be used as labeled by an approved device that is not counterfeit thereby further diminishing the liability of the manufactures.

The purpose of the head, which embodies a spring plated micro needle delivery system, is to deliver efficiently small volumes of the treatment solution to the transdermal region of the skin. This will be achieved both by the delivery of bioactive formulations directly to the dermis and by the mechanical stimulation of the nerve endings in the skin from the tapping of the micro needle device onto the surface of skin.

The invention may be in a desktop form-factor suitable for use on an ordinary clinical work surface, it may be a device of size and weight to be easily hand carried to its point-of-use, or it may be a device of size and weight as to be operated while held in the operator's hand. The invention may be suitable for use in an operating theater, and similar controlled environments, however will not require such strictly controlled environments for safe operation. The invention has a mechanism in which medical device components and materials may be loaded into an inventory chamber. The produced medical devices may be for external use, may be implantable, may be wearable, may be injectable, and may be suitable for passage through the digestive tract. The materials from which devices are assembled may be introduced into the invention in pre-enclosed cartridges, which contain microprocessors protecting the provenance and other aspects of the enclosed materials. These microprocessors interact with the invention (an in a preferred embodiment a centralized medical informatics system) before dispensing the medical device to ensure multiple safety aspects, such as that none of the constituents of the produced device have been recalled, are unexpired, are counterfeit, and have not been subjected to improper environmental conditions or forces. Inside our invention the device is produced in an aseptic environment for immediate use. This production (manufacture) consists of mechanical assembly and may include software preparation of the finished device. The invention internally fabricates some or all of the target medical device and may additionally provide custom assembly with pre-manufactured components and accessories. The fabrication process may include computer assisted manufacturing processes such as machining, laser cutting/etching, deposition, and the 2d or 3d printing of customized parts. Such printing is not restricted to printing of ink, but includes other printing technologies such as printing of circuitry, films of metal, plastics, biological materials, and similar substances. The manufacture and preparation of medical devices by the invention may include procedures customized for an individual patient.

The information in traditional medical labels is static, and once the medicine or device leaves the factory the label cannot be safely changed. In our invention the information packaged with the medicine can continue to be safely changed, which in many ways benefits patient safety while enabling novel medical informatics systems.

Our smart medical labels can communicate with external computational entities through one or more of wireless or contact-based information interchange protocols. When a smart medical label is in an environment in which communication is possible, the label checks with the network to find out if any updates are available. If updates are available, the label checks to make sure that the update is cryptographically assured to be authorized, and if so the label will update itself or permit updates by an appropriate external computational entity.

The novel medical informatics systems include disruption tolerant systems where physical movement of data is required in order to achieve utility in areas with damaged infrastructure (such as during a disaster or war), and areas with weak infrastructure such as developing areas including rural areas of developed countries. The return of used smart medicine containers back up along the supply line can carry information including reports of conditions in the field, answers to questions passed down the line, and information about where and when the medicine was used including information needed to support anti-counterfeiting schemes. Through these means label updates can be promulgated through physical movement along the supply chain of other smart labels, including compatible labels of other medicines or devices.

In one aspect, a cryptographic protocol between the medicine container and the medical device detects devices that have malware, are corrupt, and in some cases that are programmed incorrectly. If any such errors are detected, the smart medicine container will refuse to authenticate itself to the device. Thereby the safety of the patient is increased and the liability of the manufacturer is decreased. Our invention also ensures that only relevant authorities approve operating system and other updates. Our invention additionally ensures that the medicine can only be used as labeled by an approved device that is not counterfeit. Our scheme uses a combination of Device Tied Functions, Remote Attestation, and trusted hardware technology together with symmetric and asymmetric cryptologic methods.

When a medicine is used, there are many important details of the context of this use. Smart medical labels as well as other intelligent medical devices and supplies can participate in emergency communications, while also aggregating data to permit release to responders without violating relevant regulations such as HIPAA. Disrupted networks, in which centralized access to information resources is not always available, occur in many situations.

In our system, medical supplies containing smart medical labels move physically through areas in which they are transported and used. Such labels include highly constrained components such as RFID tags, devices that are less constrained such as medium-sized microcontrollers, and devices that are resource rich such as devices with direct connections to infrastructure such as electricity or network access. In our system these smart medicine labels achieve ad-hoc coordination in which according to their respective resource constraints they operate as a mesh network with domain specific consideration of prioritized aggregation of medical data. The various pieces of patient data are brought together in the locations where they are most needed, with priority to items that can be combined for de-identification conducive to specified utility.

Authentication and verification of medicine is critically important. Many people have been injured due to medicine that is expired, counterfeit, exposed to inappropriate conditions during shipping, or otherwise inappropriate for use. In our invention, active technology integrated into the medicine packaging can prevent all of these problems.

The present embodiments achieve capability under a set of resource constraints that are superior to what could be achieved under the resource constraints of each component separately. Additionally, existing systems require a fully-connected model in order to address some of the desirable properties of such a system. In our invention not all points-of-use need be connected to the central database all of the time. Our novel scheme presents significant improvements on prior art through a combination approach including packet-ferrying, time bounded encryption, predictive modeling, AI and statistical detection.

The server is the essential tool to the process in order to create the smart formulation for a patient. It is a solid platform, collecting all aspects of medical information from the patient, doctor, clinical logistics, and etc. Once the server has collected the initial information provided by the MD, including the patient's information and the provided treatment package's microchip and bar code, its high-tech characteristics of intelligence collects longitudinal data, analyzes the data by a powerful AI ensemble approach, and transforms the data into telemedicine, a computer assisted diagnosis in-turn transforming a treatment into a smart formulation treatment for that particular individual.

This distinct server application achieves the ability to not only collect and analyze data, it also provides a patient-centric portal where both physicians and patients can input their insightful health and lifestyle information, creating even more data for the server to process and analyze, and to ultimately create a formulation mostly geared for their well being.

In one aspect, provided herein is a method by which the end-user of medicines or medical devices is provided with a high assurance of the required properties through a cryptographic scheme that includes physical ferrying of data in one or a combination of elements of the supply chain. Without loss of generality, in an example embodiment, an ecosystem will contain individual medicine bottles with embedded RFID transponders, boxes of small collections of such bottles in which each box has a microcontroller with contact-based or contactless short-range communication, infrastructure points such as Wi-Fi hotspots and smartphones with cellular network access, and medical devices involved in the consumption of the individual medicine bottles such as a compounding device. A cryptographic scheme is employed such that regardless of availability of network access any consumer can detect whether they are the intended consumer (and if not that the medicine may be counterfeit). Furthermore the designated consumer will only accept any valid medicine once (preventing subversion of the supply line to use valid medicine labels for counterfeiting). Additional features include early detection of supply subversion, and propagation of medicine assurance information for medicine, which is not committed to a specific consumer.

The device may improve the health and vitality of the skin, as described above. This may be achieved both by the delivery of bioactive formulations directly to the dermis and by the mechanical stimulation of the nerve endings in the skin from the tapping of the microneedle device onto the surface of skin.

Improved skin quality and health following application of a composition described herein using a device described herein, includes but is not limited to improved appearance, increased regeneration, increased elasticity, increased anti-oxidative level, reduced photo-aging, reduced wrinkles, reduced scarring, reduced bacterial activities including acne, redistribution of fat and/or other content of the skin, reduced number and/or sizes of pores, reduced callusing, reduced sweating and/or body odor through skin, improved scalp health, increased hair density, increased evenness of hair growth, and increased hair strength.

While the uses of the microneedle injection as a general delivery method have been previously explored, the use of a method to deliver certain bioactive skin-enhancing substances or compositions described herein to the skin itself more efficiently have not been. The coupling of this delivery method with any of the substances listed above to improve skin health has significant potential.

Improved skin health, as used above, includes but is not limited to improved appearance, increased regeneration, increased elasticity, increased anti-oxidative level, reduced photo-aging, reduced wrinkles, reduced scarring, reduced bacterial activities including acne, redistribution of fat and/or other content of the skin, reduced number and/or sizes of pores, reduced callusing, reduced sweating and/or body odor through skin, improved scalp health, increased hair density, increased evenness of hair growth, and increased hair strength.

One would understand that a microneedle array as described herein may be used to administer any of the compositions described herein to a subject in need thereof.

Systems

Provided herein is a system, comprising a bioactive formation and a microneedle delivery system, wherein the bioactive formulation comprises a neurotoxin, hyaluronic acid and a pharmaceutically acceptable excipient.

Provided herein is a system, comprising a bioactive formation and a microneedle delivery system, wherein the bioactive formulation comprises a micro neurotoxin toxin, micro hyaluronic acid and a pharmaceutically acceptable excipient. Other suitable microneedle devices such as pens, rollers, and patches, may be used to delivery or collect liquids when interfaced with tissue. They can be manually or electronically applied to achieve a stamping motion, or rolled over the skin. Such devices also include, in some instances, an autoinjector.

Provided herein is a system, comprising a bioactive formation and a microneedle delivery system, wherein the bioactive formulation comprises a neurotoxin, one or more vitamins, one or more minerals, one or more retinols, one or more antioxidants, one or more growth factors, one or more bleaching/whitening agents, or a combination thereof.

In one aspect, provided herein is a system comprising a microneedle delivery device and a bioactive formulation, comprising (a) a single or an array of microneedles with a channel for liquid form to pass through; (b) a reservoir chamber with bioactive compounds or formulations customized or prefilled; (c) a plunger that releases the said compounds or formulations; (d) an optional security material to anti-reverse lock the microneedles and the chamber; (e) an optional adapter to fit any reservoir chamber; (f) an optional RFID smart label connecting to artificial intelligence portal; (g) an optional cloud-based informatics platform connected to system (big data predictive analytics); (h) an optional UV blocking agent for the chamber; and (i) an optional addition of a patch form using the groove in the microneedles for the purpose of sustained and/or extended release of the compositions, formulations or microchips.

The optional security material may comprise a Butyl Rubber O-Ring for optimizing the end-user utility and or experience. In one embodiment, the optimized butyl rubber O-ring confers pivotal advantages for the delivery of therapeutic treatment solutions to a tissue bed. In another embodiment, the optimized butyl rubber O-ring enable the overall improvement in performance and or utility of the underlying medical device. In another embodiment, the optimized butyl rubber O-ring is a flat or circular Butyl Rubber O-Ring. In another embodiment, the optimized butyl rubber O-ring serves as a liquid handling and leakage prevention seal, and improves the system efficiency characterized by an airtight mechanism for applying uniform volumes of treatment solutions. In another embodiment, the optimized butyl rubber O-ring further substantiates the overall suitability of the material in the context of medical device performance.

Modular Smart Label Data Transmission Systems for Applied End-User Optimization

Disruption tolerant transmission of supply chain and end user data, allows for both advanced safety assurances and enhanced personalized utility of medical devices in or near the clinical environment. The embodiment of this invention encompasses the application of disruption tolerant transmission smart labels to microneedle patches and other modular medical devices.

Counterfeit medicines pose serious health problems for the intended user, thus traceability and authentication technologies are in need to protect the consumer. Our invention, comprised of a smart label data transmission cryptographic system which is employed such that regardless of the availability of network access, any consumer can detect and verify whether they are the intended subject and if not, the invention will be able to recognize counterfeit medicine by identifying anomalous data descriptors. Our invention integrates medicine tracking and packaging technologies that can prevent common problems associated with health data security risks.

Our invention addresses a system which composes software frontend and backend interfaces. The software can be custom programmed for both the device and individual patient, capable of stand-alone or modular operation, or operated together with a network to facilitate telemedicine, self-assisted, and machine-assisted diagnosis and/or treatment. Smart medical labels as well as other intelligent medical devices might also aggregate data to permit interaction with emergency responders without violating relevant regulations such as HIPAA. These medical devices may be prepared with custom compounding of substances including pharmaceuticals, adhesives, lubricants, and pharmaceutical or hormone impregnated plastics. These substances may be directly applied to the medical device, inside the invention, or they may be combined after dispensing, or may be used separately.

Our invention addresses a system which may consist of either or both hardware preparation and software preparation. Hardware preparation may include attachment of wires or accessories, cutting, etching and or the lithographic printing of customized parts. Such printing is not restricted to printing of ink, but includes other printing technologies such as printing of circuitry, films of metal, plastics, biological materials, and similar substances. The software preparation may include programming of the device, including programming customized for the individual patient. The invention is capable of stand-alone operation and may include custom compounding of substances including pharmaceuticals, adhesives, lubricants, pharmaceutical or hormone impregnated plastics. Our invention addresses the application of a disruption tolerant transmission system which delivers superior personalized benefits and safety assurances for each individual. The said system, interfaces case based patient information, allowing the MD to first assess the condition of the patient then, based upon the prevailing data, provide a treatment package for the patient that contains a disruption tolerant smart label microchip and/or barcode. The microchip may be attached to any part of the packaging, and could potentially be a biodegradable entity, where the chip can be placed inside the injectable, on a patch product, or inside a pill.

Our invention further addresses an application which accommodates the processing of information from microchips, barcodes, and patient records whereby data entered into the server which leads to the formulation of new treatment packages are created and recommended for that particular patient. Most devices run common operating systems, and have updatable firmware and programming. These and other factors make them more vulnerable than previous generations to malware, mis-programming, and memory corruption. As more vital information is delivered into the server by the MD, it not only functions as passive storage, but is subsequently processed and over time serves as an interactive personalized longitudinal data architecture, allowing the server to intelligently produce a smart formulation for that particular patient's needs each time as needed. Our invention enhances an application for patient related data analytics, supply usage, and logistical elements of clinical practice. There is an especially great benefit for epidemiology where due to privacy and security concerns, the sharing of data is either undesirable or illegal. Our invention permits utility of analytics over interactive data architecture not previously possible.

Our invention confers cryptographic security to modular workflow systems such as in the clinical or supply chain environment. Application of disruption tolerant transmission networking platforms to the clinical or supply chain setting allows for stronger more efficient data transmission, thereby improving process management and furthering compliance objectives.

Our invention allows for the customization of personalized treatment strategies. Customized programming for the individual patient may enhance the application of combinatorial or stand-alone interventional operations, thereby introducing operational efficiencies to machine assisted diagnosis and/or treatment platforms such as the microneedle patch and therapeutic platform.

Our invention further supports a cryptographic disruption tolerant interface, which allows for the maintenance of sophisticated networking and data storage platforms, which, in turn, support the custom compounding of substances and other dosage formulation functions.

Our invention, as stated above supports a system whereby the end-user of medicines or medical devices is provided with a high assurance of the underlying identity and compendial properties through a cryptographic system that includes the physical ferrying of data in one or a combination of elements of the supply chain. In this environment it is the goal of the medicine producer to supply medicine to the medicine consumer with assurance as to provenance, non-expiry, and non-violation of environmental requirements. The use of a cryptographic system supports the verification of customer identity, compound identity as well as the early detection of supply subversion, and propagation of medicine assurance information for medicine which is not committed to a specific consumer.

Our invention further addresses the delivery of logistical benefits to data analytic objectives. Our platform allows for the direct utility of analytics over active data sets without compromising safety assurances in process management which may result from the illegal and or undesirable sharing of confidential patient data, supply usage, and logistical elements of clinical practice and other sensitive data archives.

The invention as described above supports a telemedicine ecosystem which consists of individual medicine bottles with embedded RFID transponders, boxes of small collections of such bottles in which each box has a microcontroller with contact based or range communication, together with infrastructure points such as WiFi hotspots and contactless short smartphones with cellular network access, and or medical devices involved in the consumption of the individual medicine bottles such as a compounding device.

The invention addresses the advantage of our smart medical labels and their overarching ability to communicate with external computational entities through one or more wireless or contact based information interchange protocols. When a smart medical label is in an environment in which communication is possible, the label checks with the network to find out if any updates are available. If updates are available, the label checks to make sure that the update is cryptographically assured to be authorized, and if so the label will update itself or permit updates by an appropriate external computational entity.

The invention addresses the operational advantage of novel medical informatics systems which integrate disruption tolerant systems where the physical movement of data is required in order to achieve utility in areas with damaged or weak infrastructure such as developing areas including rural areas of developed countries. In these cases the introduction of operational efficiencies through the utility of disruption tolerant transmission interfaces can be added at any point in the supply line and carried to other points in the supply line or to the end user.

The invention underscores a novel mechanism whereby raw source data is transmitted to a trusted third party computational entity. In another aspect the third party computational entity may be untrusted under a range of adversarial models such as honest but curious, global passive adversary, and global active adversary. After receiving the raw source data, the data aggregation entity performs a novel transformation on the data, and provides to the data consuming entity unique statistical information maximizing chosen utility while meeting the previously agreed upon constraints.

The invention further addresses the enhanced efficacy of a cryptographic protocol between the medicine container or microneedle patch and the medical device in such an event that the said devices have malware, are corrupt, and in some cases are programmed incorrectly. If any such errors are detected, the smart medicine container will refuse to authenticate itself to the device, and by that or other means make it impossible to use the medicine in a manner approved by the manufacturer. Therein our invention assures the safety of the patient and the diminished liability of the manufacturer. Our invention also ensures that the operating system and other updates are approved by the relevant authorities; a distinct advantage when specific machine states are FDA approved. Our invention additionally ensures that the medicine can only be used as labeled by an approved device that is not counterfeit. Our system uses a combination of Device Tied Functions, remote attestation, and trusted hardware technology together with symmetric and asymmetric cryptologic methods.

Method of Using Technology and Various Input for Smart Formulation

Presented is the process of personalized medicine through the uses of the appropriate components to receive the recommended formulation.

Herein lays an opportunity to place focus not only to help supplement and improve health, but to also address the opportunity to move from optimized to personalized medicine. Each individual is different; therefore each individual's treatment should be assessed differently.

With the use of the appropriate components, the process exhibited as a guide, shows not only how one may receive a personalized formulation, but also shows how efficiently high-tech and robust it can be.

In order to achieve personalized benefits at maximal level for each individual, it is evident that a combination of the right tools needs to be used.

Step 1: MD will first assess the condition of the patient. The information gathered by the MD can entail any type of medical material, such as a skin condition, general health, lab data, DNA information, etc.

Step 2: Based upon the patient's condition, MD will then provide a treatment package for the patient. The treatment package will have a microchip and a barcode. The microchip may be attached to any part of the packaging, and it could potentially be a biodegradable entity, where the chip can be placed inside the injectable, on a patch product, or inside a pill.

Step 3: The information from the microchip, barcode, and the patient's records are immediately processed and stored in a server—a cloud product.

Step 4: Based on various inputs into the server, a new formulation treatment package is created and recommended for that particular patient.

Steps 1-4 are repeated as necessary, as more vital information is collected into the server. The server not only as storage, will process all of the patient's information, and over time create personalized longitudinal data, allowing the server to intelligently produce a smart formulation for that particular patient's needs each time as needed.

The server is the essential tool to the process in order to create the smart formulation for a patient. It is a solid platform, collecting all aspects of medical information from the patient, doctor, clinical logistics, and etc.

Once the server has collected the initial information provided by the MD, including the patient's information and the provided treatment package's microchip and bar code, its high-tech characteristics of intelligence collects longitudinal data, analyzes the data by a powerful AI ensemble approach, and transforms the data into telemedicine, a computer assisted diagnosis in-turn transforming a treatment into a smart formulation treatment for that particular individual.

This distinct server application achieves the ability to not only collect and analyze data, it also provides a patient-centric portal where both physicians and patients can input their insightful health and lifestyle information, creating even more data for the server to process and analyze, and to ultimately create a formulation mostly geared for their well being.

Supply Chain Assurance Through Logistic-Aware Smart Medical Labels in a Semi-Connected Model Provided herein is a method by which the end-user of medicines or medical devices is provided with a high assurance of the required properties through a cryptographic scheme that includes physical ferrying of data in one or a combination of elements of the supply chain.

Our invention is a method by which the end-user of medicines or medical devices is provided with a high assurance of the required properties through a cryptographic scheme that includes physical ferrying of data in one or a combination of elements of the supply chain. Without loss of generality, in an example embodiment, our ecosystem will consist of individual medicine bottles with embedded RFID transponders, boxes of small collections of such bottles in which each box has a microcontroller with contact-based or contactless short-range communication, infrastructure points such as Wi-Fi hotspots and smartphones with cellular network access, and medical devices involved in the consumption of the individual medicine bottles such as a compounding device. In this environment it is the goal of the medicine producer to supply medicine to the medicine consumer with assurance as to provenance, non-expiry, non-violation of environmental requirements, etc. A cryptographic scheme is employed such that regardless of availability of network access any consumer can detect whether they are the intended consumer (and if not that the medicine may be counterfeit). Furthermore the designated consumer will only accept any valid medicine once (preventing subversion of the supply line to use valid medicine labels for counterfeiting). Additional features include early detection of supply subversion, and propagation of medicine assurance information for medicine which is not committed to a specific consumer.

Method of Using Active Technology for Medicine Packaging

Presented is the process of using active technology integrated into the medicine packaging process.

Authentication and verification of medicine is critically important. Many people have been injured due to medicine that is expired, counterfeit, exposed to inappropriate conditions during shipping, or otherwise inappropriate for use. In our invention, active technology integrated into the medicine packaging can prevent all of these problems.

Multi-factor safety guard against giving the patient the wrong drug. Factors are: (1) Optical (1D or 2D barcode) Including 3-D (holographic) barcode; (2) Interaction with RFID on individual medicine capsule; (3) Interaction with microprocessor incorporated into medicine shipping unit (such as cartridge); and (4) Processing over these data by medical device at point of use (which medical device can include purpose-built authenticators)

Interaction of all of these data occur within a central database: Including predictive modeling for advanced detection of areas of concern, AI and statistical detection of historical areas of concern to ensure security and data protection.

Our invention is distinguished by the interaction among each of these elements to achieve capability under a set of different resource constraints that is superior to what could be achieved under the resource constraints of each component separately. Additionally, existing systems require a fully-connected model in order to address some of the desirable properties of such a system. In our invention, not all points-of-use need be connected to the central database all of the time. Our novel scheme presents significant improvements on prior art through a combination approach including packet-ferrying, time bounded encryption, predictive modeling, AI and statistical detection.

Computer-Assisted Point-of-Use Manufacture of Personalized Medical Devices

Presented herein is an invention designed to create and dispense customized medical devices in or near the clinical environment in which the medical devices are to be used.

This invention consists of a machine for manufacture and customization of medical devices including implantable medical devices. In a preferred embodiment, the invention interoperates with a network for computer assisted design and customization of devices based on personal information pertinent to an individual patient. The invention is designed to create and dispense customized medical devices in or near the clinical environment in which the medical devices are to be used.

The invention may be in a desktop form-factor suitable for use on an ordinary clinical work surface, it may be a device of size and weight to be easily hand carried to its point-of-use, or it may be a device of size and weight as to be operated while held in the operator's hand. The invention may be suitable for use in an operating theater, and similar controlled environments, however will not require such strictly controlled environments for safe operation. The invention has a mechanism in which medical device components and materials may be loaded into an inventory chamber. The produced medical devices may be for external use, may be implantable, may be wearable, may be injectable, and may be suitable for passage through the digestive tract. The materials from which devices are assembled may be introduced into the invention in pre-enclosed containers which contain microprocessors protecting the provenance and other aspects of the enclosed materials. These microprocessors interact with the invention (an in a preferred embodiment a centralized medical informatics system) before dispensing the medical device to ensure multiple safety aspects, such as that none of the constituents of the produced device have been recalled, are unexpired, are counterfeit, and have not been subjected to improper environmental conditions or forces. Inside our invention the device is produced in an aseptic environment for immediate use. This production (manufacture) consists of mechanical assembly and may include software preparation of the finished device. The invention internally fabricates some or all of the target medical device and may additionally provide custom assembly with pre-manufactured components and accessories. The fabrication process may include computer assisted manufacturing processes such as machining, laser cutting/etching, deposition, and the 2nd or 3rd printing of customized parts. Such printing is not restricted to printing of ink, but includes other printing technologies such as printing of circuitry, films of metal, plastics, biological materials, microchips, and similar substances. The manufacture and preparation of medical devices by the invention may include procedures customized for an individual patient.

The software preparation may include programming of the device, including programming customized for the individual patient. The invention is capable of stand-alone operation, however in a preferred embodiment the invention operates as part of a sophisticated medical informatics system enabling advanced telemedicine, and computer assisted diagnosis and treatment with corresponding design and programming personalized to the individual patient. The manufacture of medical devices may include custom compounding of substances including pharmaceuticals, adhesives, lubricants, pharmaceutical or hormone impregnated plastics, and so forth. These substances may be directly applied to the medical device inside the invention, or they may be combined after dispensing, or they may be used separately.

Advanced Safety Assurance in Medical Devices

Presented is the method of using advanced safety assurance in the field of medical devices.

As medical devices continue to grow in sophistication it is increasingly common for them to be connected to networks, to run common operating systems, and to have updatable firmware and programming. These and other factors make them more vulnerable than previous generations to malware, mis-programming, and memory corruption. Producers of medicine are motivated to ensure their medicines are used appropriately by devices with which they are designed to interoperate.

In our invention, smart medicine labels provide assurance that the medical device is in a safe state. Note that under FDA regulations the term "label" can include a wide variety of information such as the user manual of a medical device stored in a medium such as a CD-ROM. We use the term label in this sense to include printed information, and information contained within data storage media, whether or not this information is required by regulations.

In our invention a cryptographic protocol between the medicine container and the medical device detects devices that have malware, are corrupt, and in some cases that are programmed incorrectly. If any such errors are detected, the smart medicine container will refuse to authenticate itself to the device, and by that or other means make it impossible to use the medicine in a manner approved by the manufacturer. Thereby the safety of the patient is increased and the liability of the manufacturer is decreased. Our invention also ensures that operating system and other updates are approved by the relevant authorities, a distinct advantage when specific machine states are FDA approved. Our invention additionally ensures that the medicine can only be used as labeled by an approved device that is not counterfeit. Our scheme uses a combination of Device Tied Functions, Remote Attestation, and trusted hardware technology together with symmetric and asymmetric cryptologic methods.

Anonymous Disruption Tolerant Transmission of Patient Data

Presented is the method by which utility of protected patient data can be enjoyed in environments when access to central medical control is unavailable.

When a medicine is used, there are many important details of the context of this use. Smart medical labels as well as other intelligent medical devices and supplies can participate in emergency communications, while also aggregating data to permit release to responders without violating relevant regulations such as Health Insurance Portability and Accountability Act (HIPAA). Disrupted networks, in which centralized access to information resources is not always available, occur in many situations.

Our invention provides a method by which utility of protected patient data can be enjoyed in environments when access to central medical control is unavailable. In the United States and many other jurisdictions patient data is legally protected such that it may not be disclosed if the patient is identifiable. Data from multiple patients can be combined to provide de-identified information, however this is typically done by a central authority. Our invention allows some such utility to be derived in the field when the central authority is unreachable.

In our system, medical supplies containing smart medical labels move physically through areas in which they are transported and used. Such labels include highly constrained components such as RFID tags, devices that are less constrained such as medium-sized microcontrollers, and devices that are resource rich such as devices with direct connections to infrastructure such as electricity or network access. In our system these smart medicine labels achieve ad-hoc coordination in which according to their respective resource constraints they operate as a mesh network with domain specific consideration of prioritized aggregation of medical data. The various pieces of patient data are brought together in the locations where they are most needed, with priority to items that can be combined for de-identification conducive to specified utility.

Automated Provably Secure De-Identification of Medical and Clinic Logistical Information for the Purposes of Practice Analytics Presented is the method of using automated provably secure de-identification of medical and clinic logistical information for the purposes of practice analytics.

There are many benefits to analyzing information about patient data, supply usage, and logistical elements of clinical practice including hours of operation, number and qualifications of staff, etc. There is specifically great benefit for epidemiology. In many cases, however, it is either undesirable to share some data, or illegal. Our invention permits utility of analytics over this data not previously possible.

In one example, two practices want to work together to benefit the logistical aspects of each practice, such as the optimal number of staff at different levels of qualification at specific times, days of week, seasons. They also want to track requests for particular treatments over the course of advertising campaigns that pertain to drugs or practices of each clinic. Each clinic, however, does not want to reveal exact aspects of how they do business such as the exact number of certain procedures they execute.

Through the use of our invention they can together obtain previously unachievable utility over these data while complying with applicable laws and best business practices.

In another example, medical studies that previously could not be performed due to restrictions on data sharing are made possible by our invention. This enables, for example, research by a drug company together with a hospital and NIMH or a university research group. The data can be transformed in complex ways dictated by the researchers, but can only be extracted from the system when provably satisfying chosen constraints about identification of chosen aspects of individual records.

In our invention the data producing entities and the data consuming entities agree on the aspects of the data on which they want to maximize post-aggregation utility, and which aspects can be preferentially convolved to achieve mathematically bounded and provable de-identification requirements. In one aspect the data producing entities easily transmit the raw source data through a novel mechanism to a trusted third party computational entity. In another aspect the third part computational entity may be untrusted under a range of adversarial models such as honest-but-curious, global passive adversary, and global active adversary. In these latter cases secure multi-party computation techniques provably protect against the adversary. In either case we will call this third party the data aggregation entity. After receiving the raw source data, the data aggregation entity performs our novel transformations on the data, and provides to the data consuming entities unique statistical information maximizing chosen utility while meeting the previously agreed upon constraints.

Computer-Assisted Point-of-Use Customization and Programming of Medical Devices

Presented is an invention designed to dispense customized medical devices in or near the clinical environment in which the medical devices are to be used.

This invention consists of a machine for preparation and customization of medical devices including implantable medical devices. The invention is designed to dispense customized medical devices in or near the clinical environment in which the medical devices are to be used.

The invention may be in a desktop form-factor suitable for use on an ordinary clinical work surface, it may be a device of size and weight to be easily hand carried to its point-of-use, or it may be remotely operated using a robotic technology, or it may be a device of size and weight as to be operated while held in the operator's hand. The invention may be suitable for use in an operating theater, and similar controlled environments, however will not require such strictly controlled environments for safe operation. The invention has a mechanism in which medical devices may be loaded into an inventory chamber. The medical devices may be for external use, may be implantable, may be injectable, may be wearable, and may be suitable for passage through the digestive tract. These devices may be introduced into the invention pre-enclosed in a container which contains a microprocessor protecting the provenance and other aspects of the enclosed medical device. This microprocessor interacts with the invention before dispensing the medical device to ensure multiple safety aspects, such as that the dispensed device has not been recalled, is unexpired, is genuine, has not been subjected to improper environmental conditions or forces, and so forth. Inside our invention the device is prepared in an aseptic environment for immediate use. This preparation may consist of either or both of mechanical preparation and software preparation. The mechanical preparation may include attachment of wires or accessories, and the 2nd or 3rd printing of customized parts. Such printing is not restricted to printing of ink, but includes other printing technologies such as printing of circuitry, films of metal, plastics, biological materials, and similar substances. The aforementioned mechanical preparation may include procedures customized for an individual patient. The software preparation may include programming of the device, including programming customized for the individual patient. The invention is capable of stand-alone operation, however in a preferred embodiment the invention can operate together with a network to facilitate telemedicine, and machine assisted diagnosis and/or treatment. The preparation of medical devices may include custom compounding of substances including pharmaceuticals, adhesives, lubricants, pharmaceutical or hormone impregnated plastics, and so forth. These substances may be directly applied to the medical device inside the invention, or they may be combined after dispensing, or they may be used separately.

Automated Dispensing Devices

Provided herein is an automated system for compounding pharmaceutical agents for needleless injection treatment, or Aquagold (AQT) microneedle system, or intradermal delivery of a patient is provided herein.

The system comprises: a housing enclosing an interior space; an inventory structure having a plurality of chambers for individually holding one or more pharmaceutical agent-containing single use capsules, wherein each capsule has a volume capacity of from about 0.1 to about 10.0 mL liquid; means for selecting capsules in accordance with predetermined pharmaceutical agents contained in said capsules; means for moving the selected capsules to a processing area; means for sequentially transferring a controlled quantity of the predetermined pharmaceutical agent with direct fluid communication from each selected capsule to a product container such as a product vial or a syringe under positive or negative pressure; and means for automatically discarding spent capsules from which the pharmaceutical agents have been removed after a single use.

This technology provides a means for a personalized medicine platform where the personalized medicine opportunity can be implemented, it can be used to safely and efficiently expand physician services, improve treatment and improve outcomes. By providing specific dosage control, width and depth control, speed control, and composition control, this device is applicable for patients requiring effective doses of pharmaceutical compositions or formulations.

This system and method for personalized treatment is synchronized with a complementary health management system (a computerized and networkable via wireless or wired connection) and will automatically compound and record patient specific doses of injectable medicine for disease prevention and/or treatment and the patient's progress will be monitored on the Internet longitudinally.

AQT Technology

Provided herein are devices that encompasses reconstituting, compounding, mixing, preparing and disposing of treatment compounds and formulations for AQT technology. The technology is not injectable, not topical, but rather, is somewhere between. This new method for certain compositions will enhance topical effect by stimulating collagen creation, and by penetrating into the skin. AQT will provide a unique outcome when used with an injectable composition. For example, in the case of micro botulinum toxins, instead of relaxing/paralyzing muscles, it improves skin quality and skin health. Pore size will be reduced. In case of hyaluronic acid (HA), instead of filling deep lines as a "filler" when injected, with AQT, hyaluronic acid (HA) will work as a moisturizing agent and provide radiant look and hydration into the skin. The bioactive agents for use with AQT technology can be contained within a needleless injection device, a microneedle device. A roller device may be powered and combined with needless injection technology.

The device comprises a delivery method for combination of hyaluronic acids and/or botulinum toxins, and other bioactive agents, including but not limited to botulinum toxins, poly-L-lactic acid, calcium hydroxylapatite (CaHA) and one or more additional bioactive agents. The combination of all the above mentioned therapeutics have shown to enhance aesthetic and cosmetic features on the skin, with signs of visible skin rejuvenation and no reported cases of adverse effects. The device may optionally comprise 3D printing capability producing biodegradable injectable microchips (nano 7 technology or better).

In another aspect, provided herein is a needleless injection device, AQT, or a prefilled syringe combined with an automated compounding system comprising a bioactive formulation described herein for use in connection with laser assisted drug therapy or radio frequency or ultrasound. Laser assisted drug facilitates permeation of applied agents into the skin (the stratum corneum) in a controlled manner, resulting in increased penetration of the applied agents. The erbium:yttrim-alluminum-garnet (Er:YAG) laser and the carbon dioxide (CO2) laser are two types of lasers that may be used in connection with the bioactive formulations, systems, needless injection devices, microneedle injection devices, and automated compounding systems described herein.

In one aspect, provided herein is an aqueous solution formulated for delivery using an automated compounding system comprising from about 3000 to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg of selenium; from about 30 mg to about 50 mg of glutathione (GSH); from about 100 mg to about 150 mg of anthocyanidin; from about 1 mg to about 500 mg of omega-3; from about 200 mg to about 300 mg of EPA; from about 200 mg to about 300 mg of DHA; from about 1 mg to about 500 mg of lecithin; from about 30 mg to about 50 mg of coenzyme Q10 (CoQ10); from about 100 mcg to about 150 mcg of chrome; and from about 150 mg to about 200 mg of magnesium. In one embodiment, the aqueous solution further comprises a chemical stabilizer. In another embodiment, the aqueous solution further comprises a preservative. In one embodiment, the aqueous solution has a pH of about 7.2 to about 7.6. For example, the aqueous solution has a pH of 7.4.

In another aspect, provided herein is an automated compounding system comprising a container and a bioactive formation comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg of selenium; from about 30 mg to about 50 mg of glutathione (GSH); from about 100 mg to about 150 mg of anthocyanidin; from about 1 mg to about 500 mg of omega-3; from about 200 mg to about 300 mg of EPA; from about 200 mg to about 300 mg of DHA; from about 1 mg to about 500 mg of lecithin; from about 30 mg to about 50 mg of coenzyme Q10 (CoQ10); from about 100 mcg to about 150 mcg of chrome; and from about 150 mg to about 200 mg of magnesium. In another embodiment, the aqueous solution further comprises a preservative. In one embodiment, the aqueous solution has a pH of about 7.2 to about 7.6. For example, the aqueous solution has a pH of 7.4.

In another aspect, provided herein is a needleless injection device or a prefilled syringe combined with an automated compounding system comprising a bioactive formulation comprising from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg of selenium; from about 30 mg to about 50 mg of glutathione (GSH); from about 100 mg to about 150 mg of anthocyanidin; from about 1 mg to about 500 mg of omega-3; from about 200 mg to about 300 mg of EPA; from about 200 mg to about 300 mg of DHA; from about 1 mg to about 500 mg of lecithin; from about 30 mg to about 50 mg of coenzyme Q10 (CoQ10); from about 100 mcg to about 150 mcg of chrome; and from about 150 mg to about 200 mg of magnesium.

In another aspect, provided herein is a needleless injection device or a prefilled syringe combined with an automated compounding system comprising a bioactive formulation comprising hyaluronic acid, botulinum toxin, collagen, vitamins, minerals, minoxidil, platelet-rich plasma (PRP), and/or poly-L-lactic acid (PLLA) or a combination thereof.

Provided herein is a method of treating or ameliorating a disease or one or more symptoms of a condition in a subject in need thereof, comprising administering to the subject an aqueous solution comprising from about 3000 mcg to about 5000 mcg of cyanocobalamin, from about 3000 mcg to about 5000 mcg of methylcobalamin, or a combination thereof; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg of selenium; from about 30 mg to about 50 mg of glutathione (GSH); from about 100 mg to about 150 mg of anthocyanidin; from about 1 mg to about 500 mg of omega-3; from about 200 mg to about 300 mg of EPA; from about 200 mg to about 300 mg of DHA; from about 1 mg to about 500 mg of lecithin; from about 30 mg to about 50 mg of coenzyme Q10 (CoQ10); from about 100 mcg to about 150 mcg of chrome; and from about 150 mg to about 200 mg of magnesium; wherein the composition is administered to the patient through delivery using an automated system for compounding pharmaceutical agents for treatment of a patient. In one embodiment, the one or more symptoms are selected from depression, headaches, chronic fatigue syndrome, high stress levels, hyperthyroidism, low energy, hair loss, wound healing, scarring, aging, longevity, wellness purpose, and a combination thereof. In one embodiment, the disease is selected from beriberi, Wernicke's encephalopathy, ariboflavinosis, pellagra, acne, paresthesia, microcyrtic anemia, or macrocytic anemia. In one embodiment, administration of said composition improves skin elasticity, skin regeneration, metabolism, or a combination.

In another aspect, provided herein is a method of improving wound healing in a human patient in need thereof, comprising administering to the patient an aqueous solution comprising from about 3000 mcg to about 5000 mcg of cyanocobalamin, from about 3000 mcg to about 5000 mcg of cyanocobalamin methylcobalamin, or a combination thereof; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg of selenium; from about 30 mg to about 50 mg of glutathione (GSH); from about 100 mg to about 150 mg of anthocyanidin; from about 1 mg to about 500 mg of omega-3; from about 200 mg to about 300 mg of EPA; from about 200 mg to about 300 mg of DHA; from about 1 mg to about 500 mg of lecithin; from about 30 mg to about 50 mg of coenzyme Q10 (CoQ10); from about 100 mcg to about 150 mcg of chrome; and from about 150 mg to about 200 mg of magnesium; wherein the composition is administered to the patient through an automated system for compounding pharmaceutical agents for treatment of a patient. In one embodiment, the wound is a post-surgical wound. In one embodiment, the aqueous solution is administered to the patient prior to surgery. In one embodiment, the aqueous solution is administered to the patient after surgery.

Such methods may facilitate administration of patient-tailored treatment regimens. The methods may also enable the homogeneous application of combinatorial liquid formulations with bioactive therapeutics and nutraceuticals to layers of the skin including the dermis and subcutis.

Superior direct application technology allows for the enhanced delivery of treatment solutions for restorative kinetics above topical methods of administration. Furthermore, improvement of the overall patient experience with minimized dosage loss is achieved.

Non-limiting examples of such automated systems are described, for example, in PCT Publication WO 2012/109032, which is hereby incorporated by reference in its entirety.

Automated Subdermal Injection System

Injections in the dermal space are imprecise, often resulting in a loss of treatment efficacy and/or pain at the injection or treatment site. Injections may also carry other side effects, such as leakage, lumps, formation of granulomas and bleeding. Our invention injects therapeutic agents to a precise depth using a programmable, automated apparatus or needles of a certain length that cannot penetrate deeper than the dermis. These properties address the aforementioned complications that result from manual injections. Our improvements will decrease injection complications and increasing treatment efficacy. Our improvements also make the device easier and more practical to use.

The system described herein relates to the precise application of therapeutic agents to specific body compartments from a syringe generated by an automated device. It contains several non-obvious improvements of two previously patented devices: U.S. provisional application Ser. No. 60/437,152 and PCT/KR2011/004028.

The present inventors have discussed a "System and method for personalized injection treatment" in U.S. provisional application Ser. No. 61/437,152, which is hereby incorporated by reference in its entirety. This device produces a syringe filled with a therapeutic agent custom designed for each patient. PCT Application No. PCT/KR2011/004028 discusses a "drug injecting device for use in skin surgery." The present inventors have made several improvements to these devices to address complications resulting from syringe-needle dermal injections. We describe improvements to directly inject personalized therapeutic agents into patients to precisely target specific corporal compartments by altering: needle travel length, speed and frequency, injection depth and/or increasing or decreasing needle length. Additionally, the syringe contents may be transferred to a vial and applied by pore-creating microneedles. Microneedles can be produced which are short enough to not contact the nerve-rich subdermal compartments and therefore contain the added benefit of being pain free.

In one example, a doctor or automated machine will fill a syringe with content for a patient. The contents can be transferred to a device, such as our invention, that will inject the syringe contents into the patient. The device may transfer these contents through an array of needles, for example, five 31 gauge needles.

In another example, the syringe contents may be injected into the patient through more or less needles. The needles may be very small, such as microneedles (such as those in a head in FIG. 2). The needles may be of variable lengths, sizes or design, so as to facilitate delivery of the therapeutic compounds to different corporal compartments. The needles may or may not be hollow and may puncture the skin and facilitate the transfer of therapeutic agent across the skin. The device may have screw-like threading to facilitate transfer of therapeutic agents into the skin. The needle or needle head may be designed to be replaceable, reused, exchangeable or disposable.

Figure 2:
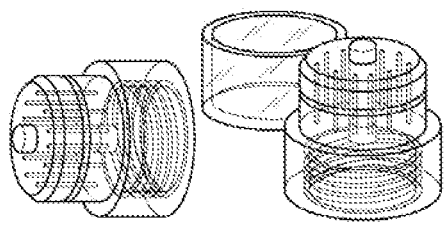
FIG. 2 is an image of a screw on a microneedle head.

In another example, the therapeutic agent may be administered by a vial connected to a microneedle head (such as in FIG. 2; PCT/KR2011/000625, U.S. Ser. No. 13/575,525). The microneedles may create pores in the epidermis to facilitate transfer of the therapeutic agents into the dermis. The amount of fluid injected into the patient per administration and the injection speed can be controlled by a slide crank mechanism, similar to the unit depicted in unit 330 in FIG. 1. U.S. provisional application Ser. No. 61/437,152 discusses custom therapies in syringes, vials or capsules. Any of those vessels may be attached to a device described herein, and may be directly connected to our unit, which can apply the contents to the treatment area. Our unit may contain several microneedles to create epidermal pores and facilitate treatment. The microneedle head may screw on to the vial or attach to the handheld automatic injector.

The contents of the syringe or components of the therapeutic agent may or may not be determined by a doctor or machine designed to personalize the contents. The injecting device may be modified such that, similar to U.S. provisional application Ser. No. 61/437,152, to use capsules or vials instead of a syringe. In such a circumstance, the needle injector will be dual-headed, so as to puncture the vial or capsule.

Figure 3:
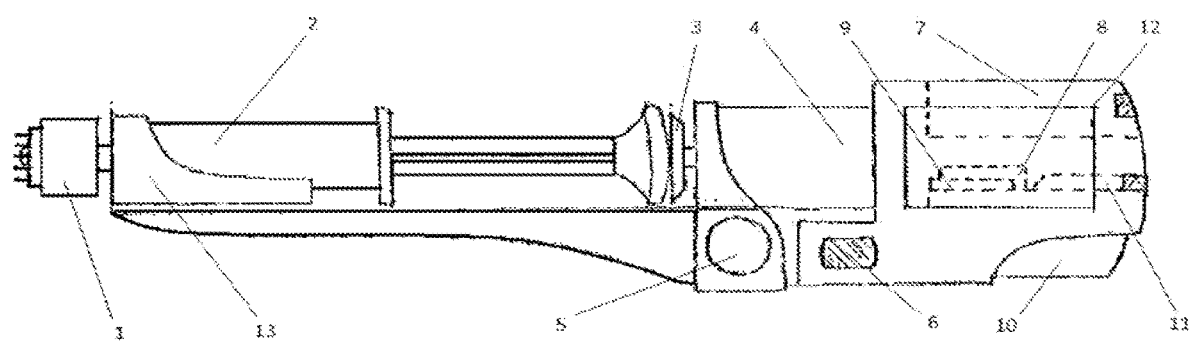
FIG. 3 is a schematic representation of a device in a syringe configuration. Alternative configurations include vial- and capsule-loaded configurations. The device holds a syringe (2) for automatic injection via a plurality of microneedles in the microneedle head. Ejection volume is controlled by an information processor (9). Other elements are noted: the motor or actuator (4) to control the piston (3), exchangeable and controllable needle head (1) and cam system and dial to adjust needle injection depth (5), and needle head ejector (10). Information is shown to the user in a display panel that may include a manual or touchscreen control panel (12) and data is stored in a storage unit (11) that may be removable. The needle head (1) may be controlled by an actuator (13).
Figure 4:
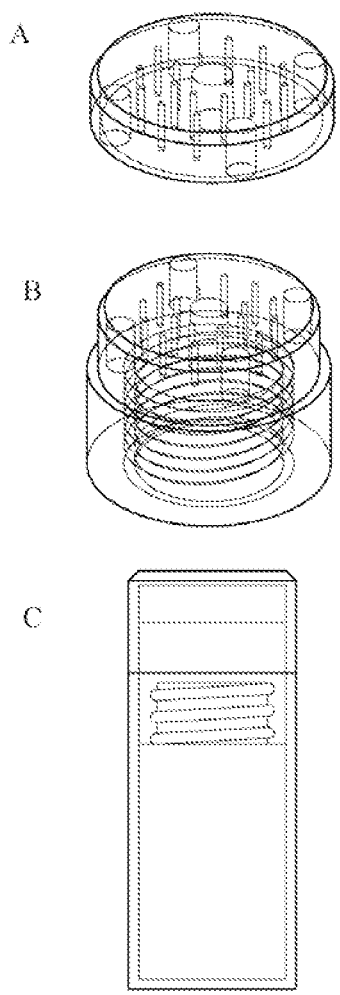
FIG. 4 provide three additional views of a microneedle device. AQT microneedle components: (A) microneedles, (B) housing of the needles and (C) a reservoir.
Figure 5:
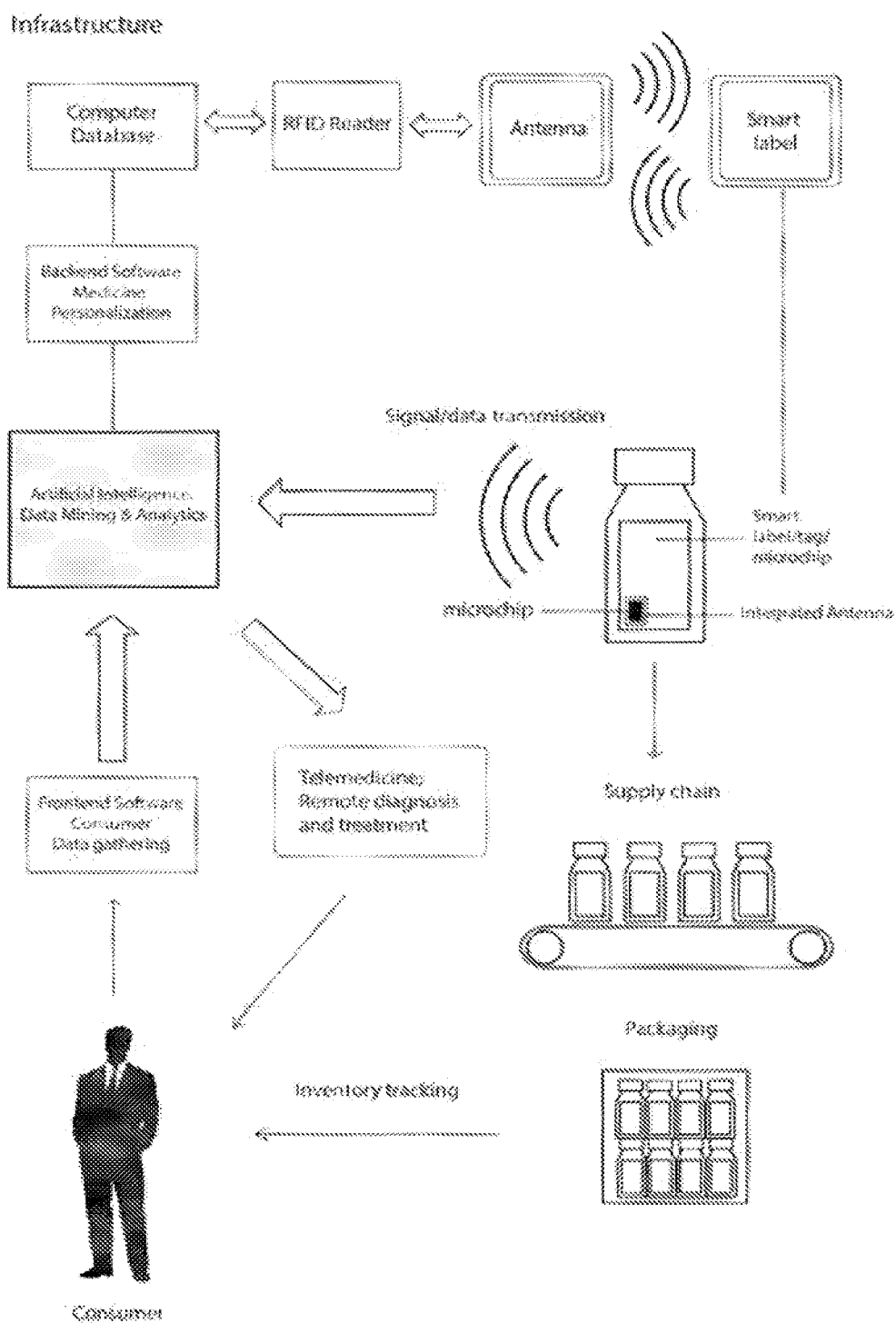
FIG. 5 is a flow chart illustrating modular smart label data transmission systems for applied user-end optimization. The chart herein addresses a scheme whereby the smart label cryptographic protocol detects and directs the efficient operation and prevention of supply chain subversion events further allowing for enhanced end user service optimization in customized medical devices.
Figure 6:
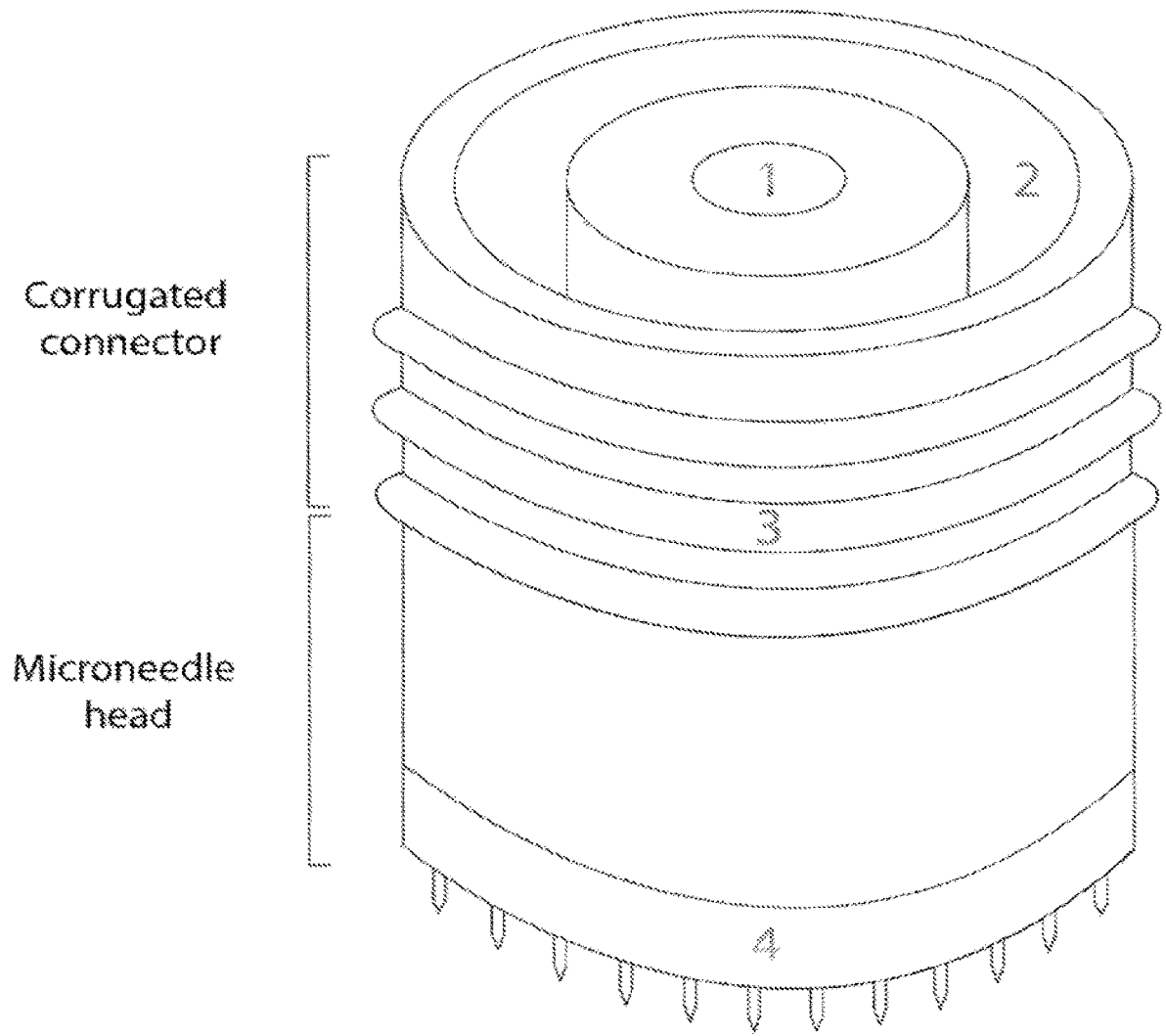
FIG. 6 is a diagram showing the connection of corrugated connector and microneedle head. The rubber based connector is such that its flexibility will allow connections with small openings (1) and large ones (2) to fit and seal the microneedle head. The corrugated connector, also made of rubber (3), will further allow larger embodiments to connect to this system with the spring plate microneedle head (4).

The device may be a portable unit with no external attached cable. It may also be operated remotely using robotic technology combined with AQT. Power may be provided by a replaceable or rechargeable battery. The device may also contain an information processor, a data storage unit and an electronic chip to enable wireless connectivity. These enhancements are observed in FIG. 3. This ensures dosage control, width and depth control, speed control, composition and formulation control and any safety measures.

Several changes may be made to the mechanism controlling the needle position. Specifically, the home position of the needle and the traveling length of the needle will be controlled by variable configurations in the slider crank mechanism. The speed and frequency of the needle punctures are able to be modulated by a variable speed motor. The cam-based system may be designed such that it can control how long the needle stays underneath the skin. The system may be attached to a stem cell device, PRP device, laser device, radio frequency device or ultrasound device.

The needle head may include sensors or an aspirating mechanism to collect biological samples or information from the patient. The sensors may detect: blood glucose level, body temperature, or perspiration rate among other measurements.

A Spring Plate Microneedle System Bearing a Universally Adoptable Corrugated Connector Herein, we detail a system which embodies a feature for the efficient delivery of treatment solutions to the skin, by using a micro needle transjection mechanism for the direct deployment of bioactive formulations and/or other drugs or solutions, such that the therapeutic outcome will be enhanced in contrast to traditional topical application treatment methods. The invention further embodies a universal corrugated connector designed to fit the system to any other system including but not limited to reservoirs, containers, vials, electronic appendages, etc.

The system embodies a cadre of micro needles housed in a plastic and or polymer composite cartridge which allows for the secure interface of the head with the reservoir; the said head may include a single or plurality of solid, screw-type micro needles, of single or varied length. Typically, the needles attach to a plate or are embedded within the plate thereby presenting an array of micro needles mounted onto a plate but housed as a microneedle cartridge. The plate can be made of any metal, metal alloy, ceramics, organics metalloid, polymer, or combination thereof, including composites, such as gold, steel, silicon and other biocompatible materials.

A further embodiment of the Spring Plate Delivery System is the manual direct application mechanism, whereby a micro needle cartridge can be directed to engage and or permeate the surface of the skin. Once in the skin the existence of a trans-epidermal osmotic gradient and hydration force facilitates the efficient delivery of treatment solutions to the transdermal space.

A further embodiment of the micro needle head, are the corrugated fittings which facilitate the secure adjunct positioning of the head to the reservoir. The head which contains a micro needle cartridge, may bear a corrugated rubber connector with a threaded single use, self-destruct locking feature; additional tamper proof efficiencies may be derived from the inclusion of a snap lock and or single use self-destruct locking feature. A further advantage conferring embodiment of the head is the presence of a butyl rubber or halo-butyl rubber connector, which bestows a universal applicability feature to vials, electronic appendages etc. The said feature may stand to include a corrugated rubber clasp which corresponds with the glass, plastic and or polymer flange of the respective vial or electronic appendage and may confer further flexibility as a naive fitted feature which allows for multiple refills, usage and or removals of the head.

A further embodiment of the plastic or polymer composite micro needle head is the advantage conferring features which stand to include but are not limited to the inclusion of naïve and or Radio Frequency ID labeled Butyl and or halo-butyl Rubber O-Rings. The integration of the stated advantage conferring features further address an embodiment for improved fluid handling and modular data management and interfacing capabilities. Conferring an altogether superior utility function.

A cadre of micro needles housed in a plastic or polymer composite head is used to deliver treatment solutions, vitamins and any combination thereof, directly to the dermis, the second layer of skin. The application of a mechanical load to the pin of the spring lock system enables the micro needles to puncture the epidermal barrier and deliver the desired substances directly to the dermis for faster, more efficient, and more effective absorption by the skin. The Spring Plate mechanism, housed in the plastic or polymer composite cartridge, is effectively the interface whereby the manual direct application mechanism calibrates the controlled delivery of the treatment solution to the transdermal space.

As stated above, the enhanced delivery of treatment solutions to the skin is dependent on the existence of a trans-epidermal osmotic gradient and hydration force which enables the efficient delivery of treatment solutions to the transdermal space. Advanced advantage conferring efficiencies may also be embodied by a micro needle head which contains a corrugated butyl rubber connector. The corrugated rubber connector is a unique advantage conferring feature which bestows the microneedle head with a universally adoptable feature for interfacing with multiple glass and or plastic vials, reservoirs and containers as well as electronic appendages for an altogether enhanced adjunct liquid handling, security and surveillance utility. The corrugated rubber connector allows for the accommodation of adjunct features such as a threaded single use, self-destruct locking features with or without RFID labels, as well as a snap lock mechanism or a naïve clasp and screw feature for multiple refills, usage and or removals of the head.

The device includes a single or plurality of solid, screw-type microneedles, of single or varied lengths housed in a plastic or polymer composite head which embodies a corrugated rubber connector. Typically the needles attach to a substrate or are embedded within the substrate. The substrate can be made of any metal, metal alloy, ceramics, organics metalloid, polymer, or combination thereof, including composites, such as gold, steel, silicon, PVP (polyvinylpyrrlidone) etc. The screw-shape dimensions may be variable. For example, in one embodiment the screw-shape may be a tight coiled screw shape, whereas in another embodiment the screw-shape might be a loose coiled screw shape. The corrugated rubber connector is a unique advantage conferring feature which bestows the microneedle head with a universally adoptable feature for interfacing the micro needle cartridges with multiple glass and or plastic vials, reservoirs and containers as well as electronic appendages for an altogether enhanced adjunct liquid handling, security and surveillance utility.

A further embodiment of the micro needle head, are the corrugated ridges which facilitate the secure adjunct positioning of the head to the reservoir. The head containing the micro needle mounted array plate may bear a threaded single use, self destruct locking feature with or without a snap lock mechanism or a naïve threaded screw feature for multiple refills, usage and or removals of the head. The universal applicability of the corrugated connector enhances the utility of the drug delivery platform. The utility of the spring plate microneedle system can be controlled by altering one or more of several design variables. For example, the applicability of the micro needle cartridge for the uniform hydrodynamic conductivity of a single device array to the dermis is enhanced by fitting a corrugated rubber connector which embodies a universal applicability feature to vials, electronic appendages etc., which in turn expands the applicability of control features such as the diffusion rate, mass transfer and hydrodynamic conductivity to a diversity of manual and automated devices.

A further embodiment of the Spring Plate Delivery System is the manual pin-adjusted mechanism for the release and or inhibition of fluid flow from the reservoir to the transdermal space in the skin via naïve or screw thread micro needles. During intervals of mechanical load the translational force contributes to the elevation of the micro needle mounted plate which enables the otherwise unhindered flow of treatment solutions through the micro needles and into the transdermal space. In the absence of a mechanical load the converse is true and the treatment solution is contained securely in the reservoir. The presence of a corrugated rubber connector may vary in length and as such confers additional utility features which encompass the flexibility of the spring plate delivery system, thereby enabling the delivery of treatment solutions to hard to reach areas of the body.

Advanced advantage conferring efficiencies may be embodied by a micro needle cartridge which contains the micro needle mounted array plate together with adjunct liquid handling and device security and surveillance bearing features such as a corrugated rubber single use, self-destruct locking feature with or without RFID or corrugated rubber fittings with or without RFID. RFID labeled heads or plastic and or polymer composite heads bearing appendages with RFID labels, ensure improved surveillance measures, thereby assuring the safety of the patient once the operating system and other updates are approved by the relevant marketing authorities and or the FDA; a further advantage of the RFID label is that the medicine can only be used as labeled by an approved device that is not counterfeit thereby further diminishing the liability of the manufactures.

The purpose of the head which embodies a spring plated micro needle delivery system that is made up of a cadre of micro needles housed in the plastic or polymer composite head, is to introduce an efficiency for delivering small volumes of the treatment solution to the transdermal region of the skin. The head of the device bearing a corrugated rubber connector will complement the drug delivery and or control element of the device so as to improve the health and vitality of the skin, as detailed in the summary of the invention. This will be achieved both by the delivery of bioactive formulations directly to the dermis and by the mechanical stimulation of the nerve endings in the skin from the tapping of the micro needle device onto the surface of skin.

Combinatorial Performance Materials for Enhanced Medical Device End-User Utility Materials for Improved Medical Device End-User Experience The invention addresses a feature for optimizing the enhanced medical device end-user utility and or experience. Said feature(s) confers pivotal non obvious advantages for the delivery of therapeutic treatment solutions to the tissue bed. The fundamental advantage conferring feature constitutes the use of a flat or circular O-Ring with or without affixed modular smart label data transmission device labels or microchips, which serve as a seal for containers and further facilitates system efficiencies characterized by an airtight mechanism for applying uniform volumes of treatment solutions transdermally.

The enhanced performance of a medical device remains a direct function of the advantage conferring features and materials which make for an obvious and or non-obvious improvement to the overall end-user utility and or experience. By employing butyl rubber or halogenated butyl rubber as the material of choice for improving combinatorial performance objectives, this invention supports our interest in conferring an enhanced medical transjection device end-user utility and or experiences. The invention described provides direct commercial advantages associated with environmental impact and a spectrum of shelf and functional qualities.

Our invention embodies a system for administering therapeutic treatment solutions to the intradermal tissue bed. Enhanced system efficiencies may be conferred by integrating a flat or circular butyl rubber or halogenated butyl rubber O-Ring seal at the interface between the treatment solution reservoir and the functional transjection cap. We propose the positioning of a butyl rubber or halogenated butyl rubber O-Ring concentric to the inner wall containing ratchet design of the reservoir cap which enables a unidirectional locking mechanism; such an orientation must be embedded and of such that the O-Ring be positioned apically to the cusp of the threaded channel, thereby effectively conferring an airtight seal upon closure of the system. Non-obvious advantages of the airtight feature articulated by the inclusion of the biodegradable butyl rubber or halogenated butyl rubber O-Ring as described is the efficient, uniform delivery of the treatment solution to the transdermal region. Other performance enhancing attributes may be derived from the low environmental impact, non-reactive chemical makeup of the butyl rubber or halogenated butyl rubber as a sealant, which in turn renders it suitable for myriad applications and to a diversity of chemical, pH and temperature related constraints.

Our invention presents both obvious and non-obvious improvements which together account for the overall differences in performance and utility between the underlying medical device and other single use transjection systems.

Improved end user utility and or experience via the application of combinatorial performance material butyl rubber or halogenated butyl rubber may be conferred by excellent weather and ozone resistance which further addresses the stability of the material in the context of medical device utility.

A further advantageous embodiment for the enhanced utility of the flat or circular O-Ring in Improving medical device end user experiences may be attributed to good adhesion of the butyl rubber or halogenated butyl rubber in comparison to other types of rubber, hence the suitability of the material in the context of medical device performance.

A further advantageous embodiment for the enhanced utility of the flat or circular O-Ring in improving medical device end user experiences may be attributed to the high impermeability of the butyl rubber or halogenated butyl rubber to gases as well as its good heat resistance property in comparison to other types of rubber, hence the suitability of the material in the context of medical device efficiency.

A further embodiment for the enhanced utility of the modular smart label data transmission device label or microchip affixed flat or circular O-Ring is the improvement in equipment reliability, end user surveillance and reduced environmental impact in comparison to other types of non RFID labeled butyl rubber or halogenated butyl rubber; hence the suitability of the RFID labeled Butyl Rubber or halogenated butyl rubber in the context of medical device utility.

The butyl rubber and halogenated butyl rubber O-Rings exhibit high performance durability with time. Other Industrial rubber O-Rings degrade while exhibiting poor durability with time.

Figure 7:
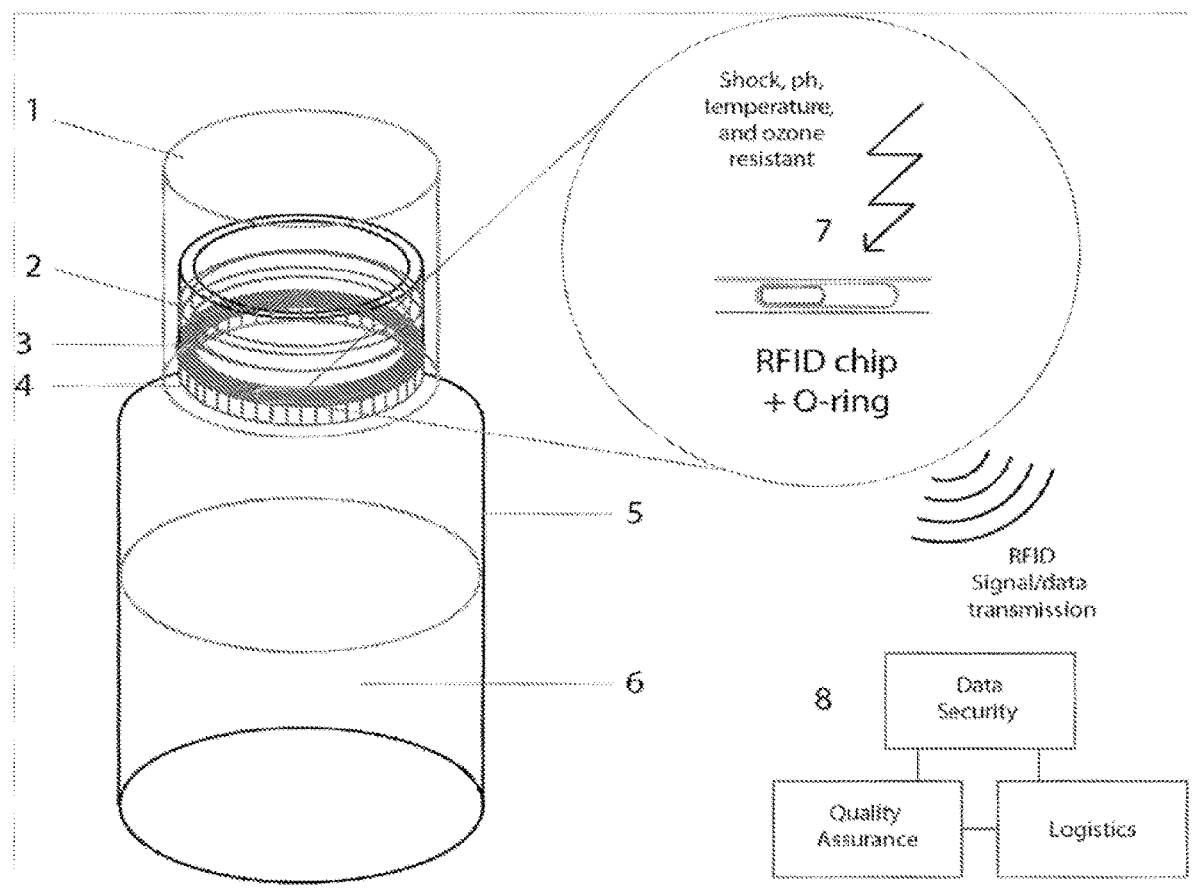
FIG. 7 provides a depiction of the utility feature conferred by the circular or flat O-Rings. Said features enable enhanced liquid handling capabilities as evidenced by an airtight mechanism which facilitates the efficient and uniform delivery of treatment solutions to the skin. Said features are positioned at the interface of the cap and the reservoir channel so as to effectively prevent the leakage of treatment solution dosages. The RFID chip+O-ring depiction has been expanded. The cap/cover (1) will interface with the vial or container (5) containing a certain compound (6). The connection of both the cap/cover and the container may be sealed with a threaded opening (2). While pressure is applied vertically through the twisting motion of the thread, the rubber O-ring (3) seals the two interfaces (1) and (5) together. A ratchet mechanism (4) at the end will lock the cap in place. Embedded inside the rubber O-ring is a RFID chip (7) which material is shock, pH, temperature, and ozone resistant. The RFID chip will be stable enough under different environments to be able to effectively transmit data for applications such as data security, quality assurance/control, and logistics (8).
Figure 8:
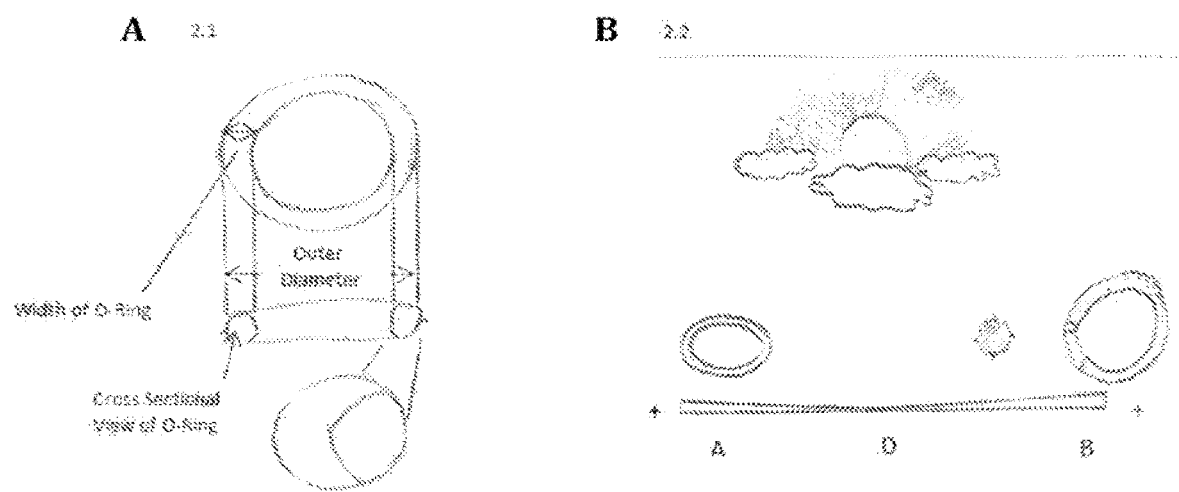
FIG. 8A-8B depict a utility feature conferred by the circular or flat O-Rings (FIG. 8A). Said features enable obvious and non-obvious advantages conferred by excellent weather and ozone resistance, temperature resistance (FIG. 8B) and the resistance to pH induced degradation of the butyl rubber or halogenated butyl rubber in comparison to other industrial rubbers and further addresses the stability of the material in the context of medical device utility, end user performance and pharmacological agent turbidity. Said features effectively enable enhanced material durability while preventing the leakage and inefficient delivery of treatment solution dosages with time.
Figure 9:
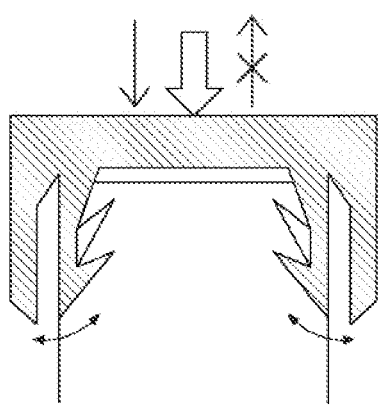
FIG. 9 illustrates anti-unlock safety features of an O ring in a microneedle device.
Figure 10:
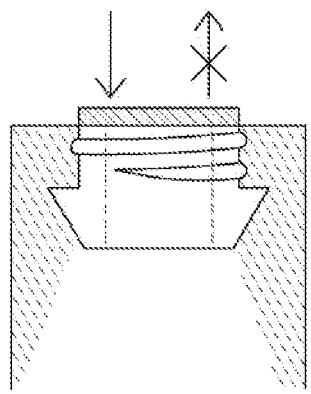
FIG. 10 illustrates anti-unlock safety features of an O ring in a microneedle device.
Figure 11:
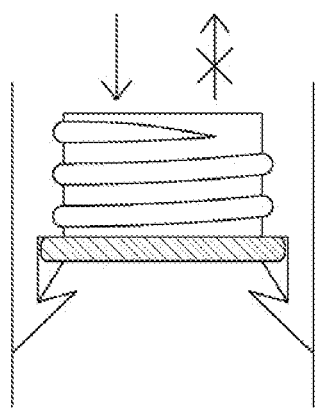
FIG. 11 illustrates anti-unlock safety features of an O ring in a microneedle device.
Figure 12:
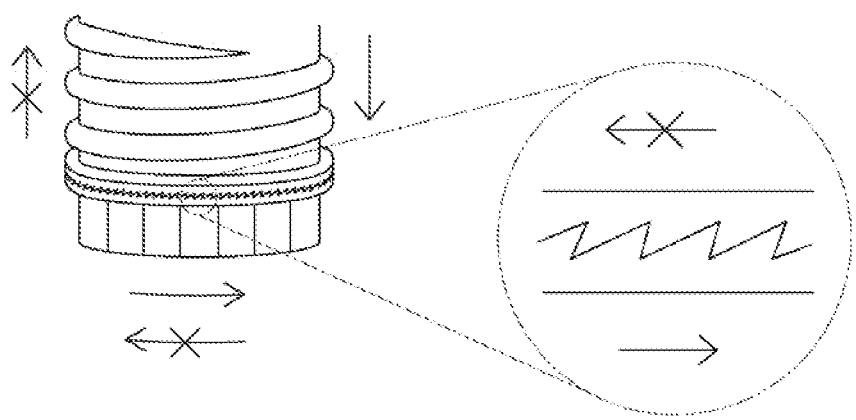
FIG. 12 illustrates anti-unlock safety features of an O ring in a microneedle device.

FIG. 7 provides an illustration of an entire system depicting how the O-ring and RFID chip are to be applied in medical application settings, in this example, to store compound in a sealed and locked container.

Our invention embodies obvious and non-obvious improvements in the Butyl Rubber O-Ring, for optimizing the end-user utility and or experience. The underlying feature(s) confers pivotal obvious and non-obvious advantages for the delivery of therapeutic treatment solutions to the tissue bed. The features encompassing the invention enables the overall improvement in performance and or utility of the underlying medical device. The use of a flat or circular Butyl Rubber O-Ring serves as a liquid handling and leakage prevention seal, which also improves the system efficiency characterized by an airtight mechanism for applying uniform volumes of treatment solutions transdermally. These properties further substantiates the overall suitability of the material in the context of medical device performance.

One advantage embodied by the application of butyl rubber as a combinatorial performance material, is its chemical and biological inertness due largely in part to the chemical make-up of the material which renders it nonpolar with low absorption of drugs and water. For optimal liquid handling applicability our invention purports the positioning of the butyl rubber or halogenated rubber O-Ring concentric to the inner wall. The ratchet design of the reservoir cap facilitates a unidirectional locking mechanism; any such arrangement where the embedded butyl rubber or halogenated butyl rubber seal enhances the combinatorial performance of the self-secure cap with the O-Ring positioned apically to the cusp of the threaded channel, will effectively confer an airtight seal upon closure of the system.

An advantage further embodied by the application of butyl rubber or halogenated butyl rubber as a combinatorial performance material, is the utility conferred by affixing modular smart label data transmission device labels or microchips to flat or circular O-Rings. Each butyl rubber or halogenated butyl rubber O-Ring, positioned concentrically to the inner wall containing ratchet design of the reservoir cap, facilitates quality assurance, patient security and bio therapeutic dosage data transmission features, which amount to improvements in equipment reliability, end user utility and clinical environment surveillance thereby perpetuating the overall suitability of the RFID labeled butyl rubber or halogenated butyl rubber in the context of medical transjection device utility and performance.

EXAMPLES

The application may be better understood by reference to the following non-limiting examples, which are provided as exemplary embodiments of the application. The following examples are presented in order to more fully illustrate exemplary embodiments and should in no way be construed, however, as limiting the broad scope of the application.

Example 1

An exemplary aqueous solution containing the following ingredients: from about 3000 to 5000 mcg cyanocobalamin, from about 3000 to 5000 mcg methylcobalamin, or a combination thereof; from about 700 to about 1000 mg ascorbic acid (vitamin C); from about 11 to about 15 mg zinc; from about 4 to about 6 mg ahseutasanchin; from about 100 to about 200 IU vitamin E; from about 150 to about 300 IU vitamin D; from about 100 to about 150 mcg selenium; from about 30 to about 50 mg glutathione (GSH); from about 100 to about 150 mg anthocyanidin; from about 1 to about 500 mg omega-3; from about 200 to about 300 mg EPA; from about 200 to about 300 mg DHA; from about 1 to about 500 mg lecithin; from about 30 to about 50 mg CoQ10; from about 100 to about 150 mcg chrome; and from about 150 to about 200 mg magnesium.

An exemplary aqueous solution containing the following ingredients: from about 3000 mcg to 5000 mcg of cyanocobalamin, from about 3000 mcg to 5000 mcg of methylcobalamin, or a combination thereof; from about 700 mg to about 1000 mg of ascorbic acid (vitamin C); from about 11 mg to about 15 mg of zinc; from about 4 mg to about 6 mg of ahseutasanchin; from about 100 IU to about 200 IU of vitamin E; from about 150 IU to about 300 IU of vitamin D; from about 100 mcg to about 150 mcg of selenium; from about 30 mg to about 50 mg of glutathione (GSH); from about 100 mg to about 150 mg of anthocyanidin; from about 1 mg to about 500 mg of omega-3; from about 200 mg to about 300 mg of EPA; from about 200 mg to about 300 mg of DHA; from about 1 mg to about 500 mg of lecithin; from about 30 mg to about 50 mg of coenzyme Q10 (CoQ10); from about 100 mcg to about 150 mcg of chrome; and from about 150 mg to about 200 mg of magnesium.

Example 2

This example provides a representative example of an aqueous solution to be used in a method described herein. The composition may contain the following ingredients: About 5000 mcg of cyanocobalamin or/and methylcobalamin; About 1000 mg of ascorbic acid (vitamin C); About 15 mg of zinc; About 6 mg of ahseutasanchin; About 200 IU of vitamin E; About 300 IU of vitamin D; 150 mcg of selenium; About 50 mg of glutathione (GSH); About 150 mg of anthocyanidin; About 500 mg of omega-3; About 300 mg of EPA; About 300 mg of DHA; About 500 mg of lecithin; About 50 mg of coenzyme Q10 (CoQ10); About 150 mcg of chrome; About 200 mg of magnesium; and About 1 ml q.s., sterile water for injection.

The aqueous solution is formulated in physiological saline and adjusted to about pH 7.4, thereby minimizing any injecting pain beyond the needle prick. In addition, the aqueous solution may be optionally supplemented with a preservative (e.g., benzyl alcohol) and/or a chemical stabilizer (e.g., gentisic acid), depending on anticipated shelf-life.

Example 3

The purpose of this example is to evaluate the efficacy of a composition described herein in treating the signs of aging present on facial skin. A composition is prepared as in Example 2.

Two groups of human subjects (8-10 subjects per group) are administered with the composition or physiological saline (control) twice a day for a period of 29 days. At the end of the 29 day test period, the subjects are polled regarding various aspects of the effectiveness of the composition described herein in treating and/or minimizing signs of aging related health problems.

Example 4

The purpose of this example is to evaluate the efficacy of a composition described herein in treating the signs of aging present on facial skin. A composition is prepared as in Example 2.

Two groups of human subjects (8-10 subjects per group) are administered via a microneedle injection system with the composition or physiological saline (control) on days 1, 3, 7, 10, 14, 21, 30, 60, and 90 of treatment. At the end of the 90-day test period, the subjects are polled regarding various aspects of the effectiveness of the composition described herein in treating and/or minimizing aging related health problems. The following aspects of the composition described herein are evaluated:

(1) effectiveness of the composition described herein in combating fatigue and/or boosting the energy production (i.e., making the individual feel more energetic and full of vitality);

(2) effectiveness of the composition described herein in improving the overall function of the immune system;

(3) effectiveness of the composition described herein in boosting the mood;

(4) effectiveness of the composition described herein in promoting calcium intake;

(5) effectiveness of the composition described herein in maintaining blood pressure; and (6) effectiveness of the composition described herein in reliving cardiovascular conditions.

Patients treated with the composition exhibit improvement in one or more of the symptoms described herein.

What is claimed is:

1. A method for delivery of a bioactive composition to a subject's skin with a microneedle delivery device without a plunger, the method comprising:
    selecting an exchangeable needle head having a plurality of microneedles each having one or multiple grooves inset along an outer wall of the microneedles;
    attaching the exchangeable needle head to a reservoir of the microneedle delivery device, the reservoir holding a predetermined dosage of the bioactive composition to be delivered, the reservoir being attached to or containing a spring and plate coupled to the exchangeable needle head and configured, at the time the exchangeable needle head is attached to the reservoir, to inhibit flow of the bioactive composition from the reservoir, the bioactive composition including at least one compound selected from the group consisting of a vitamin, a mineral, retinoic acid, stem cells, hyaluronic acid, collagen, a neurotoxin, platelet-rich plasma, poly-L-lactic acid, a vaccine, adalimumab, etanercept, bimatoprost, minoxidil, and lidocaine and being inhibited, at the time the exchangeable needle head is attached to the reservoir, from flowing out of the reservoir by the spring and plate; and
    administering the predetermined dosage of the bioactive composition in the subject's skin in a single administration using the microneedle delivery device, the single administration comprising
        repeatedly tapping a distal end of the microneedle device on the subject's skin, wherein each single tap causes the plurality of microneedles to penetrate the subject's skin, and each single tap further causes the spring and plate to release the bioactive composition from the reservoir so that the bioactive composition flows through the one or multiple grooves and into the subject's skin without the use of a plunger, and
        releasing pressure on the subject's skin from each single tap when the single tap is completed, causing the spring and plate to resume inhibiting flow of the bioactive composition from the reservoir.

2. The method of claim 1, wherein the microneedles are non-hollow.

3. The method of claim 1, further comprising
    driving flow of the bioactive composition contained in the reservoir to the microneedles with a pump or suction mechanism.

4. The method of claim 3, further comprising
    driving flow of the bioactive composition contained in the reservoir to the microneedles with a mechanical spring loaded pump.

5. The method of claim 2, wherein the microneedles each have a screw thread shaped groove around the microneedle, so that the flow of the bioactive composition is along the screw thread shaped groove on each microneedle.

6. The method of claim 5, wherein the microneedles are from 0.1 mm to about 2.5 mm in length and from 0.01 mm to about 0.5 mm in diameter.

7. The method of claim 6, wherein the microneedles further comprise gold outer surfaces.

8. The method of claim 7, wherein the plurality of microneedles comprises an array of microneedles in the shape of a circle.

9. The method of claim 8, wherein the microneedles are made of 24-carat gold plated stainless steel and comprise an array of 20 microneedles.

10. The method of claim 1, wherein the bioactive composition comprises a neurotoxin.

11. The method of claim 1, wherein the bioactive composition comprises hyaluronic acid.

12. The method of claim 10, wherein the bioactive composition further comprises a second composition selected from the group consisting of a vitamin, and a mineral.

13. The method of claim 1, wherein the bioactive composition comprises retinoic acid.

14. The method of claim 1, wherein the bioactive composition comprises retinol.

15. The method of claim 10, wherein the bioactive composition further comprises hyaluronic acid.

16. The method of claim 10, wherein the neurotoxin is botulinum toxin.

17. The method of claim 16, wherein botulinum toxin is botulinum toxin type A or botulinum toxin type B.

18. The method of claim 1, wherein the bioactive composition is delivered within a dermal layer of the subject's skin.

19. The method of claim 1, wherein the bioactive composition comprises a vaccine.

20. The method of claim 1, wherein the bioactive composition comprises adalimumab.

21. The method of claim 1, wherein the bioactive composition comprises etanercept.

22. The method of claim 1, wherein the bioactive composition comprises bimatoprost.

23. The method of claim 1, wherein the bioactive composition comprises minoxidil.

24. The method of claim 1, wherein the bioactive composition is delivered at a dermal and epidermal junction of the subject's skin.

25. The method of claim 1, wherein the repeated tapping is made in a circular motion on the subject's skin.

26. The method of claim 1, wherein the repeated tapping is made on the subject's skin in a linear motion, a patterned motion, a free-style motion, or a cross-hatched motion.

27. The method of claim 1, wherein the microneedle device further includes a pin configured, when the distal end of the microneedle device is tapped against the subject's skin, to convert mechanical load on the pin to translational force on the plate, elevating the plate and allowing flow of the bioactive composition from the reservoir.

28. The method of claim 1, wherein flow of the bioactive composition contained in the reservoir to the microneedles is gravity driven.

29. A method for delivery of a bioactive composition to a subject's skin with a microneedle delivery device without a plunger, the method comprising:
- selecting an exchangeable needle head having a plurality of microneedles each having one or multiple grooves inset along an outer wall of the microneedles;
- attaching the exchangeable needle head to a reservoir of the microneedle delivery device, the reservoir holding a predetermined dosage of the bioactive composition to be delivered, the reservoir being attached to or containing a spring and plate coupled to the exchangeable needle head and configured, at the time the exchangeable needle head is attached to the reservoir, to inhibit flow of the bioactive composition from the reservoir, the bioactive composition including at least one compound selected from the group consisting of a vitamin, a mineral, retinoic acid, stem cells, hyaluronic acid, collagen, a neurotoxin, platelet-rich plasma, poly-L-lactic acid, a vaccine, adalimumab, etanercept, bimatoprost, minoxidil, and lidocaine and being inhibited, at the time the exchangeable needle head is attached to the reservoir, from flowing out of the reservoir by the spring and plate; and
- administering the predetermined dosage of the bioactive composition in the subject's skin in a single administration using the microneedle delivery device, the single administration comprising
  - repeatedly tapping a distal end of the microneedle device on different locations on the subject's skin, wherein each single tap causes the plurality of microneedles to penetrate the subject's skin, and each single tap further causes the spring and plate to release the bioactive composition from the reservoir so that the bioactive composition flows through the one or multiple grooves and into the subject's skin without the use of a plunger, and
  - releasing pressure on the subject's skin from each single tap when the single tap is completed, causing the spring and plate to resume inhibiting flow of the bioactive composition from the reservoir.

30. A method for delivery of an anesthetic composition to a subject's skin with a microneedle delivery device without a plunger, the method comprising:
- selecting an exchangeable needle head having a plurality of microneedles each having one or multiple grooves inset along an outer wall of the microneedles;
- attaching the exchangeable needle head to a reservoir of the microneedle delivery device, the reservoir holding a predetermined dosage of the anesthetic composition to be delivered, the reservoir being attached to or containing a spring and plate coupled to the exchangeable needle head and configured, at the time the exchangeable needle head is attached to the reservoir, to inhibit flow of the anesthetic composition from the reservoir; and
- administering the predetermined dosage of the anesthetic composition in the subject's skin in a single administration using the microneedle delivery device, the single administration comprising
  - repeatedly tapping a distal end of the microneedle device on different locations on the subject's skin, wherein each single tap causes the plurality of microneedles to penetrate the subject's skin, and each single tap further causes the spring and plate to release the anesthetic composition from the reservoir so that the anesthetic composition flows through the one or multiple grooves and into the subject's skin without the use of a plunger, and
  - releasing pressure on the subject's skin from each single tap when the single tap is completed, causing the spring and plate to resume inhibiting flow of the anesthetic composition from the reservoir.

* * * * *